(12) United States Patent
Zhang et al.

(10) Patent No.: US 11,339,177 B2
(45) Date of Patent: May 24, 2022

(54) HETEROARYL COMPOUNDS AS INHIBITORS OF NECROSIS, COMPOSITION AND METHOD USING THE SAME

(71) Applicant: ACCRO BIOSCIENCE INC., Grand Cayman (KY)

(72) Inventors: Xiaohu Zhang, Suzhou (CN); Haikuo Ma, Suzhou (CN); Jiyue Zheng, Suzhou (CN); Sudan He, Suzhou (CN)

(73) Assignee: Accro Bioscience (HK) Limited, Wan Chai (HK)

( * ) Notice: Subject to any disclaimer, the term of this patent is extended or adjusted under 35 U.S.C. 154(b) by 71 days.

(21) Appl. No.: 16/625,703

(22) PCT Filed: Jun. 23, 2018

(86) PCT No.: PCT/US2018/039180
§ 371 (c)(1),
(2) Date: Dec. 21, 2019

(87) PCT Pub. No.: WO2018/237370
PCT Pub. Date: Dec. 27, 2018

(65) Prior Publication Data
US 2021/0155635 A1  May 27, 2021

(30) Foreign Application Priority Data

Jun. 23, 2017 (CN) .......................... 201710483983.2
Jun. 6, 2018 (CN) .......................... 201810575869.7

(51) Int. Cl.

| | | |
|---|---|---|
| C07D 498/04 | (2006.01) |
| C07D 471/04 | (2006.01) |
| C07D 519/00 | (2006.01) |
| A61P 35/00 | (2006.01) |
| A61P 3/00 | (2006.01) |
| A61P 25/00 | (2006.01) |
| A61P 29/00 | (2006.01) |
| A61K 31/437 | (2006.01) |
| A61K 31/4375 | (2006.01) |
| A61K 31/4985 | (2006.01) |
| A61K 31/5383 | (2006.01) |

(52) U.S. Cl.
CPC ............ *C07D 498/04* (2013.01); *A61P 35/00* (2018.01); *C07D 471/04* (2013.01); *C07D 519/00* (2013.01)

(58) Field of Classification Search
CPC .. C07D 498/04; C07D 519/00; C07D 471/04; A61P 35/00; A61P 3/00; A61P 25/00; A61P 29/00; A61K 31/437; A61K 31/4375; A61K 31/4985; A61K 31/5383
See application file for complete search history.

(56) References Cited

U.S. PATENT DOCUMENTS

| | | |
|---|---|---|
| 2011/0028467 A1 | 2/2011 | Ahn |
| 2011/0172217 A1 | 7/2011 | Fujioka et al. |
| 2016/0256458 A1 | 9/2016 | Bair et al. |
| 2019/0284180 A1 | 9/2019 | Zhang |

FOREIGN PATENT DOCUMENTS

WO  WO-2018183964 A1 * 10/2018 ........... A61K 31/472

OTHER PUBLICATIONS

Hou, J., "Discovery of potent necroptosis inhibitors targeting RIPK1 kinase activity for the treatment of inflammatory disorder and cancer metastasis." Cell death & disease 10.7 (2019): 1-13.*
Donnez, J., "Uterine fibroid management: from the present to the future." Human Reproduction Update 22.6 (2016): 665-686.*
Skin Cancer Prevention—The Skin Cancer Foundation, 2015 p. 1-3; https://www.skincancer.org/skin-cancer-prevention.*
Verweij, M. F., Preventive medicine between obligation and aspiration. vol. 4. Springer Science & Business Media, 2000; Chapter 3 p. 25-43.*
New Oxford American Dictionary: Therapy (Eds. Stevenson, A., and Christine A. L. : Oxford University Press, 2011. Oxford Reference. Date Accessed Apr. 30, 2021.*

* cited by examiner

*Primary Examiner* — John M Mauro
(74) *Attorney, Agent, or Firm* — Feng Tian

(57) ABSTRACT

The present disclosure provides heteroaryl compounds of Formula (I), processes for their preparation, pharmaceutical compositions containing them, and their use in the treatment of diseases and disorders, arising from or related to necrosis. Formula (I) is shown below:

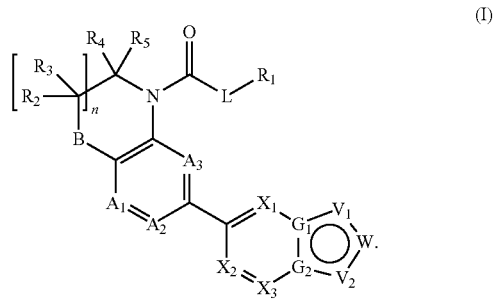

(I)

19 Claims, 1 Drawing Sheet

HETEROARYL COMPOUNDS AS INHIBITORS OF NECROSIS, COMPOSITION AND METHOD USING THE SAME

CROSS REFERENCE TO RELATED APPLICATIONS

This application claims the benefit of Chinese Patent Applications 201710483983.2, filed on Jun. 23, 2017; and 201810575869.7, filed on Jun. 6, 2018; all of which are hereby incorporated by reference.

FIELD OF INVENTION

The present invention generally relates to heteroaryl compounds and, more particularly, relates to novel heteroaryl compounds that are useful in the therapies targeting necrosis mediated diseases, including inflammatory diseases, tumors, metabolic diseases, and neurodegenerative diseases such as cerebral ischemia and stroke, in mammals.

BACKGROUND OF THE INVENTION

Different types of cell death are often defined by morphological criteria, and are classified as apoptosis and necrosis, two of the basic types. Apoptosis is characterized by cell shrinkage, chromatin condensation, the increased activities of cysteinyl aspartate-specific proteases or caspases, and the controlled breakdown of the cell into apoptotic bodies. Because apoptosis is usually physiological aberrations, it is not inflammatory. Necrosis is thought to begin with an impairment of the cell's ability to maintain homeostasis, continue to cause damage of the plasma membrane integrity, and lead to cytoplasmic and organelle swelling and the eventual lysis of the cell. Due to the release of cytoplasmic contents into the surrounding extracellular space, necrosis usually results in inflammatory response.

Early studies considered necrosis as an accidental and uncontrolled form of cell death lacking underlying signaling events. But later studies has shown that when stimulated by pro-inflammatory cytokines such as tumor necrosis factor-α (TNF-α), some cells choose the necrotic pathway instead of the apoptotic pathway. Such cell types include L929 murine fibroblasts and the NIH 3T3N murine fibroblasts. Recent research on the function of RIP1/RIP3 in TNF-α promoted necrosis pathway laid the foundation to elucidate the mechanism of necrosis. See Cho Y. S. et al., Cell 2009; 137(6): 1112-23; Zhang D. W. et al., Science 2009, 325(5938): 332-6; He, S. et al., Nat. Immunolo. Cell 2009; 137(6): 1100-11.

For example, some lethal stimuli can induce either apoptosis or necrosis, depending on the cell type and/or experimental setting. Regarding the molecular bases of this phenomenon, two members of the receptor-interacting protein kinase (RIP) family, RIP1 and RIP3, have been demonstrated to control the switch between apoptotic and necrotic cell death. When the apoptosis pathway is malfunctioned or inhibited, the necrosis pathway can be activated. This regulated necrotic cell death, or necroptosis, can be mediated by the interaction of activated RIP3 and mixed lineage kinase like (MLKL). RIP1 can induce the function of RIP3 to promote necroptosis while the proteolytic activity of a ripotosome complex formed by RIP1, fas-associating death domain (FADD) and caspase-8 can antagonize the necroptosis promotion activities of RIP3. Upon RIP3 phosphorylation of Thr357 and Ser358 in MLKL, human MLKL shifts from its monomeric state to an active oligomeric state. The oligomeric MLKL can bind to phosphoinositol and myocardial phospholipid so that the necrosome complex can move from cytoplasm to cell membrane or organelle membrane, and form permeable channels in the membrane structure, destroy the membrane integrity, and induce cell death.

In addition, phosphorylated RIP3 can interact with downstream bioenergetics enzymes including glycogen phosphorylase (PYGL), glutamate-ammonia ligase (GLUL) and glutamate dehydrogenase 1 (GLUD1), thereby enhancing their catalytic activity. Enhanced glycogenolysis and glutaminolysis can provide additional respiratory substrates, such as phosphorylated glucose and ketoglutarate, accelerate mitochondrial citric acid cycle, and ultimately result in the overgeneration of reactive oxygen species (ROS). Excess ROS, in turn, can trigger mitochondrial membrane permeabilization (MMP), thereby mediating TNF-induced programmed necrosis. Therefore, inhibition of necrosis may become a potential target for the treatment of metabolic diseases, such as diabetes.

Programmed necrosis may be involved in cell death associated with lesions of neurons and glial cells—the most essential components of the central nervous system. Many research projects indicate that inhibition of programmed necrosis may protect the nervous system. Some research programs seek to reduce harms to nervous system by reversing the necrosis and mitigating tissue damage. Accordingly, inhibition of necrosis often becomes the target of treatment for injuries to the nervous system. For example, in ischemic stroke, loss of cerebral circulation may lead to local or total cerebral ischemia and hypoxia. The ensuing death of large number of neurons may affect their corresponding nerve motor function. Consequently reducing the death of neurons may become the objective for the treatment of ischemic stroke.

Accordingly, in order to improve the afore-mentioned diseases caused by necrosis, there is a need for effective inhibitors of necrosis.

SUMMARY OF THE INVENTION

The present disclosure provides heteroaryl compounds as inhibitors of necrosis, and compositions and applications thereof. These disclosed heteroaryl compounds, and compositions and applications thereof, may effectively inhibit necrosis, thereby finding application in treatments of necrotic pathway-related diseases and disorders, including, for example, inflammation, tumors, metabolic diseases and neurodegenerative diseases such as cerebral ischemia and stroke.

An aspect of the present disclosure provides a compound of formula (I):

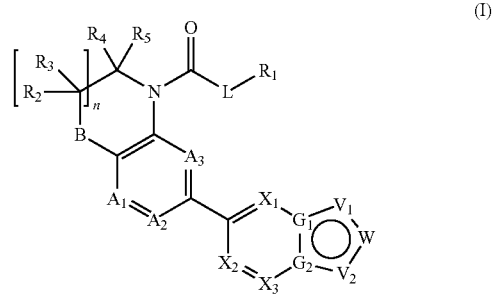

or a pharmaceutically acceptable salt, metabolite, hydrate, solvate, stereoisomer or a tautomer thereof, wherein n is 0, 1 or 2;

$A_1$, $A_2$ and $A_3$ are independently N or $CR_6$;

B is O, S, S=O, $S(=O)_2$, $NR_7$ or $CR_7R_8$;

$X_1$, $X_2$ and $X_3$ are independently N or $CR_9$;

$G_1$ and $G_2$ are independently N or C;

$V_1$ and $V_2$ are independently N, O, S, $NR_{10}$ or $CR_{10}$;

W is $V_3$, $V_4$—$V_5$, or $V_4$=$V_5$, wherein when W is $V_4$—$V_5$ or $V_4$=$V_5$, $V_4$ bonds with $V_1$, $V_5$ bonds with $V_2$;

$V_3$, $V_4$ and $V_5$ are independently N, O, S, or $CR_{11}$,

L is a bond, O, S, $NR_{16}$ or $CR_{16}R_{17}$;

$R_1$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_{14}$, wherein each hetero atom is independently N, O or S;

each of $R_2$, $R_3$, $R_4$, $R_5$, $R_7$, and $R_8$ is independently selected from the group consisting of H, deuterium, halide, —CN, —OH, amino, $C_{1-6}$ alkyl, $C_{1-6}$ alkoxy, $C_{1-6}$ alkylamino, $C_{3-6}$ cycloalkyl, —C(=O)$C_{1-6}$ alkyl, —C(=O)O$C_{1-6}$ alkyl, phenyl, 5-6 membered heteroaryl comprising 1-3 hetero atoms, and 3-8 membered heterocycle comprising 1-3 hetero atoms, wherein each hetero atom is independently N, O or S, and wherein each of $C_{1-6}$ alkyl, $C_{1-6}$ alkoxy, $C_{1-6}$ alkylamino, $C_{3-6}$ cycloalkyl, —C(=O)$C_{1-6}$ alkyl, —C(=O)O$C_{1-6}$ alkyl, phenyl, 5-6 membered heteroaryl, and 3-8 membered heterocycle are unsubstituted or substituted with 1-3 groups independently selected from the group consisting of deuterium, halide, $C_{1-3}$ alkyl and $C_{1-3}$ alkoxy;

or $R_2$ and $R_3$ together form a carbonyl bond (=O);

or $R_2$ and $R_3$ together, with atom(s) they attached to, form $C_{3-6}$ cycloalkyl or 3-6 membered heterocycle comprising 1-2 hetero atoms, wherein each hetero atom is independently N, O or S;

or $R_4$ and $R_5$ together form a carbonyl bond (=O);

or $R_4$ and $R_5$ together, with atom(s) they attached to, form $C_{3-6}$ cycloalkyl or 3-6 membered heterocycle comprising 1-2 hetero atoms, wherein each hetero atom is independently N, O or S;

or $R_7$ and $R_8$ together form a carbonyl bond (=O);

or $R_7$ and $R_8$ together, with atom(s) they attached to, form $C_{3-6}$ cycloalkyl or 3-6 membered heterocycle comprising 1-2 hetero atoms, wherein each hetero atom is independently N, O or S;

each of $R_6$, $R_9$, and $R_{10}$ is independently selected from the group consisting of H, deuterium, halide, —CN, —OH, amino, $C_{1-6}$ alkoxy, $C_{1-6}$ alkylamino, $C_{1-6}$ alkylthio, $C_{3-6}$ cycloalkyl, $C_{1-6}$ alkyl, 3-8 membered heterocycle comprising 1-3 hetero atoms, phenyl, and 5-6 membered heteroaryl comprising 1-3 hetero atoms, wherein each hetero atom is independently N, O or S, and wherein each of $C_{1-6}$ alkoxy, $C_{1-6}$ alkylamino, $C_{1-6}$ alkylthio, $C_{3-6}$ cycloalkyl, $C_{1-6}$ alkyl, 3-8 membered heterocycle, phenyl, and 5-6 membered heteroaryl are unsubstituted or substituted with 1-3 groups independently selected from the group consisting of deuterium, halide, $C_{1-3}$ alkyl and $C_{1-3}$ alkoxy; $R_{11}$ is H, deuterium, halide, —CN, —OH, $C_{1-6}$ alkoxy, $C_{1-6}$ alkylthio, $C_{1-6}$ alkyl, $C_{3-6}$ cycloalkyl or —$NR_{12}R_{13}$;

$R_{12}$ is H, $C_{1-6}$ alkyl or $C_{3-6}$ cycloalkyl;

$R_{13}$ is H, C(=O)$R_{15}$, C(=O)$NR_{15}R_{18}$, C(=O)O$R_{15}$, $S(=O)_2R_{15}$, $S(=O)_2NR_{15}R_{18}$, $C_{1-6}$ alkyl, $C_{3-6}$ cycloalkyl, $C_{2-6}$ alkenyl, phenyl, 3-6 membered heterocycle comprising 1-3 hetero atoms, or 5-6 membered heteroaryl comprising 1-3 hetero atoms, wherein each hetero atom is independently N, O or S, and wherein each of $C_{1-6}$ alkyl, $C_{3-6}$ cycloalkyl, phenyl, 3-6 membered heterocycle and 5-6 membered heteroaryl is unsubstituted or substituted with 1-3 groups independently selected from the group consisting of deuterium, halide, —CN, $C_{1-6}$ alkyl, $C_{1-6}$ alkoxy, $C_{3-6}$ cycloalkyl, and 3-6 membered heterocycle comprising 1-3 hetero atoms, each hetero atom is independently N, O or S;

$R_{14}$ is H, deuterium, halide, —OH, oxy, —CN, -amino, $C_{1-6}$ alkylamino, $C_{1-6}$ alkyl, $C_{3-6}$ cycloalkyl, or $C_{1-6}$ alkoxy, wherein each of $C_{1-6}$ alkylamino, $C_{1-6}$ alkyl, $C_{3-6}$ cycloalkyl, and $C_{1-6}$ alkoxy is unsubstituted or substituted with 1-3 groups independently selected from the group consisting of deuterium, halide, and $C_{1-3}$ alkyl;

each of $R_{15}$ and $R_{18}$ is independently selected from the group consisting of H, $C_{1-6}$ alkyl, $C_{2-6}$ alkenyl, $C_{2-6}$ alkynyl, $C_{3-6}$ cycloalkyl, phenyl, 3-6 membered heterocycle comprising 1-3 hetero atoms, and 5-6 membered heteroaryl comprising 1-3 hetero atoms, wherein each hetero atom is independently N, O or S, and wherein each of $C_{1-6}$ alkyl, $C_{2-6}$ alkenyl, $C_{2-6}$ alkynyl, $C_{3-6}$ cycloalkyl, phenyl, 3-6 membered heterocycle and 5-6 membered heteroaryl is unsubstituted or substituted with 1-3 groups independently selected from the group consisting of deuterium, halide, —CN, —OH, —$CF_3$, $C_{1-6}$ alkyl, $C_{1-6}$ alkoxy, $C_{3-6}$ cycloalkyl, and 5-6 membered heterocycle comprising 1-3 hetero atoms, each hetero atom is independently N, O or S;

or $R_{15}$ and $R_{18}$ together, with nitrogen atom they attached to, form a 4-6 membered ring;

or $R_{15}$ and $R_{10}$ together, with adjacent atoms they attached to, form a 5-6 membered ring;

and $R_{16}$ and $R_{17}$ are independently H, deuterium, halide, —OH, $C_{1-3}$ alkyl or $C_{1-6}$ alkoxy.

In some embodiments of aspects provided herein, each of $V_1$ and $V_2$ is independently O, S, $NR_{10}$ or $CR_{10}$. In some embodiments, each of $V_3$ and $V_5$ are independently C—$NR_{12}R_{13}$, $R_{12}$ and $R_{13}$ as defined above. In some embodiments, n is 0 or 1, and B is O, $NR_7$ or $CR_7R_8$, $R_7$ and $R_8$ as defined above. In some embodiments, $R_{14}$ is H, deuterium, halide, —OH, oxy, —CN, -amino, $C_{1-6}$ alkyl, $C_{3-6}$ cycloalkyl, or $C_{1-6}$ alkoxy, wherein each of $C_{1-6}$ alkyl, $C_{3-6}$ cycloalkyl, and $C_{1-6}$ alkoxy is unsubstituted or substituted with 1-3 groups independently selected from the group consisting of deuterium, halide, and $C_{1-3}$ alkyl.

In some embodiments, subgroup

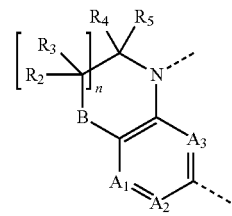

is selected from the group consisting of:
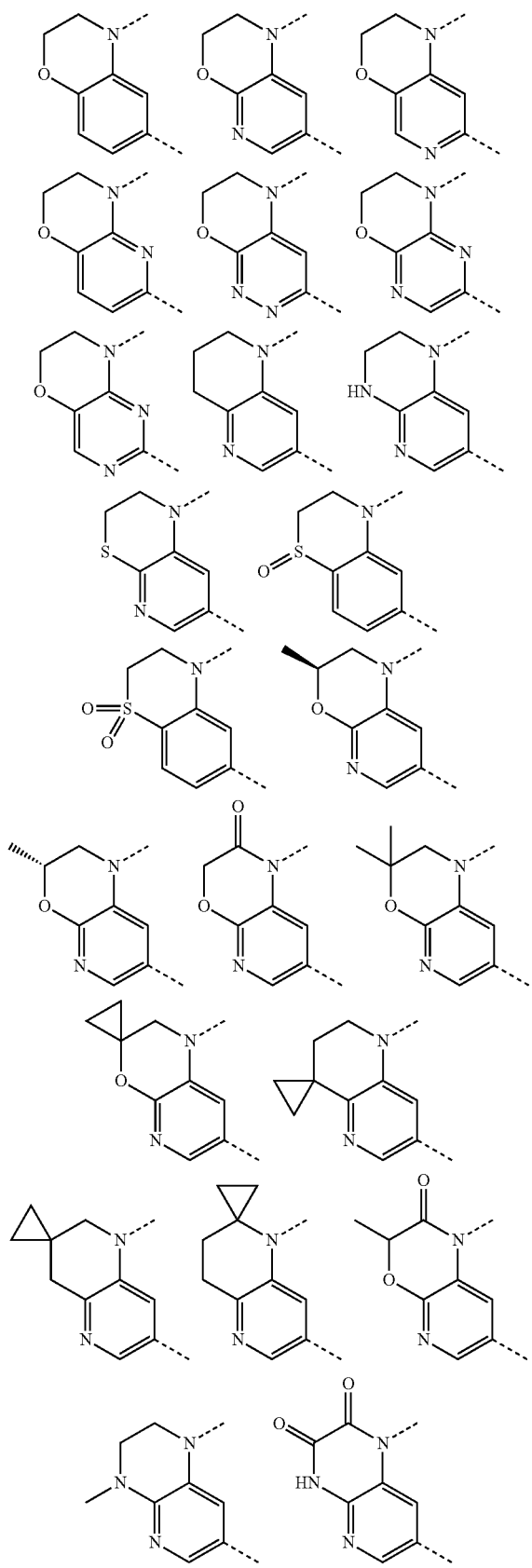
-continued
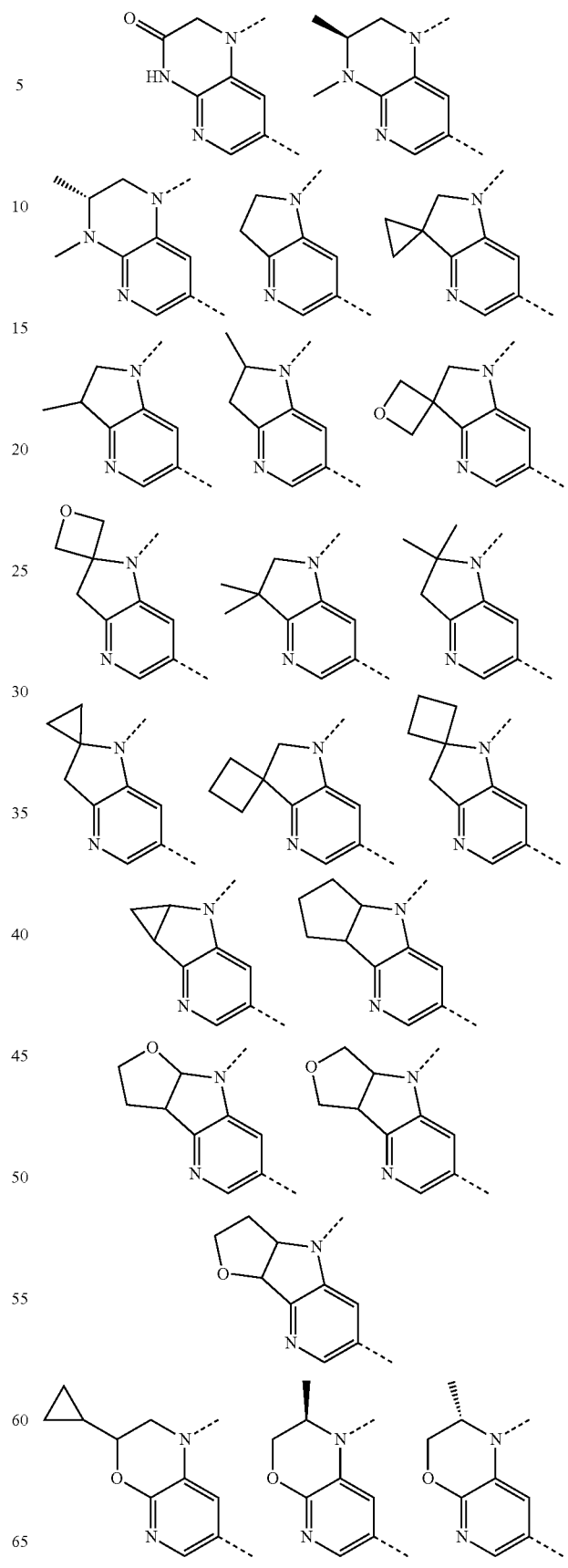

-continued
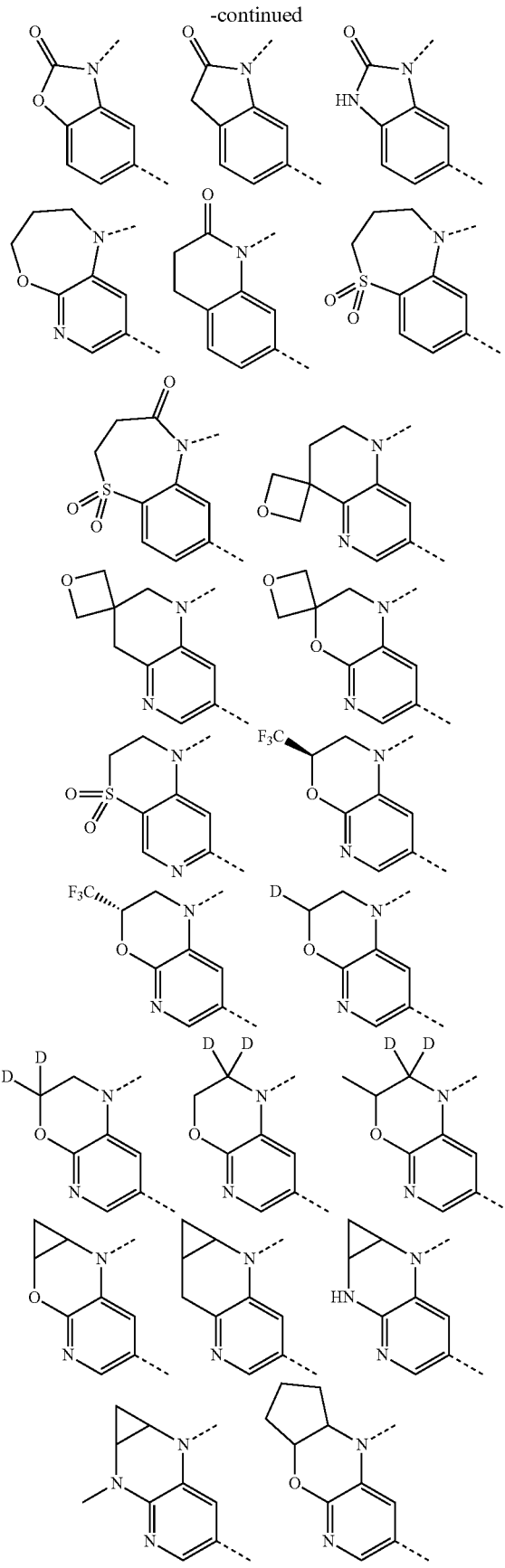
In some embodiments, subgroup
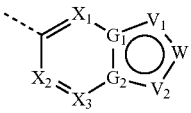
is selected from the group consisting of:
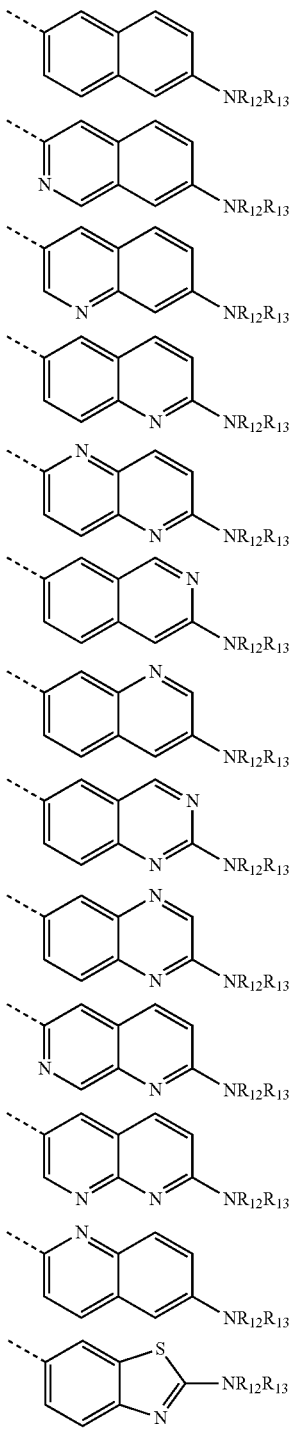

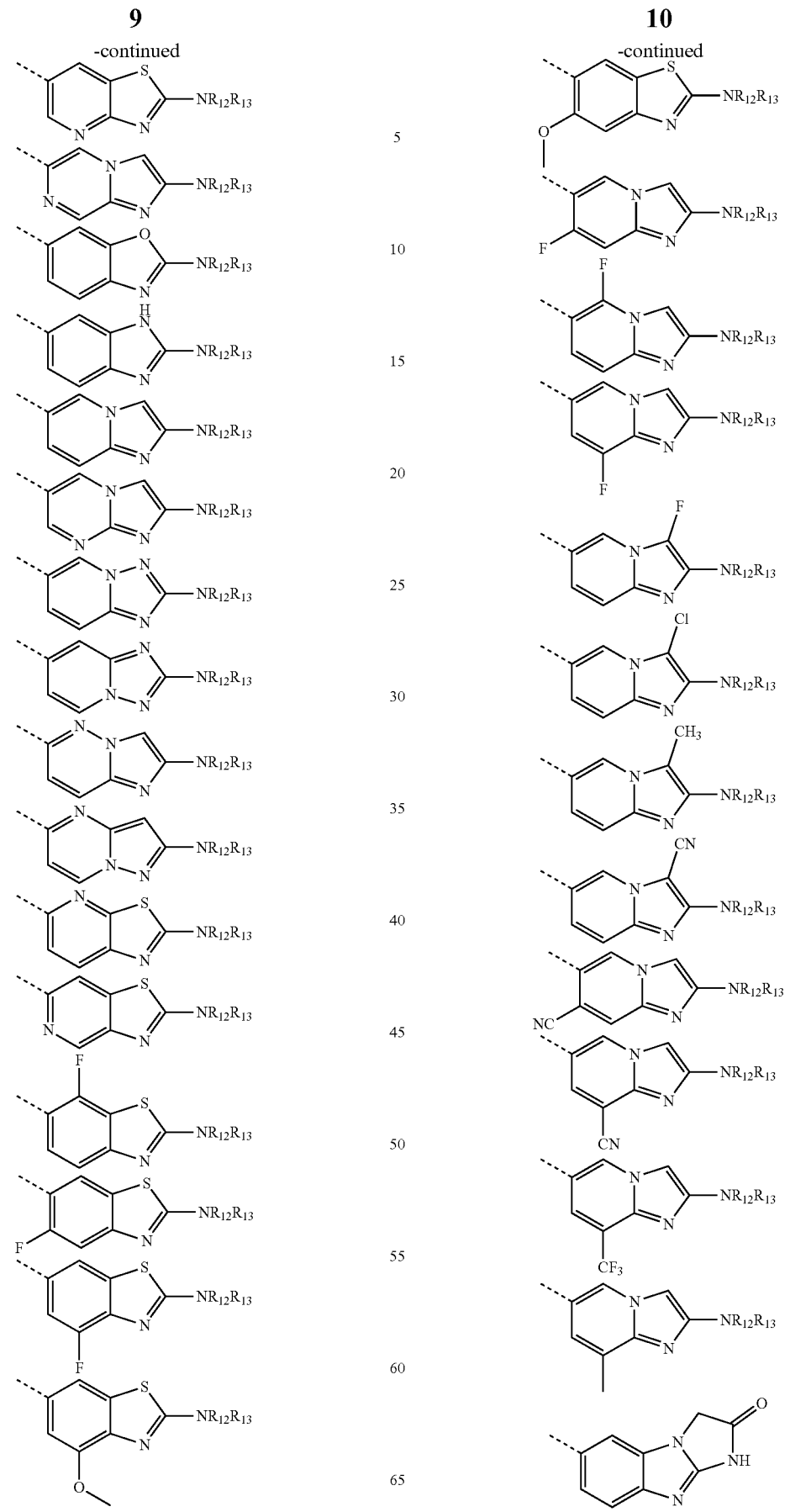

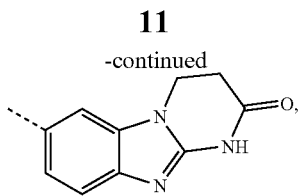
unsubstituted or substituted by 1-3 groups independently selected from the group consisting of H, deuterium, halide, —CN, —OH, amino, $C_{1-6}$ alkoxy, $C_{1-6}$ alkylthio, $C_{3-6}$ cycloalkyl or $C_{1-6}$ alkyl.
In some embodiment, $R_1$ is selected from the group consisting of:
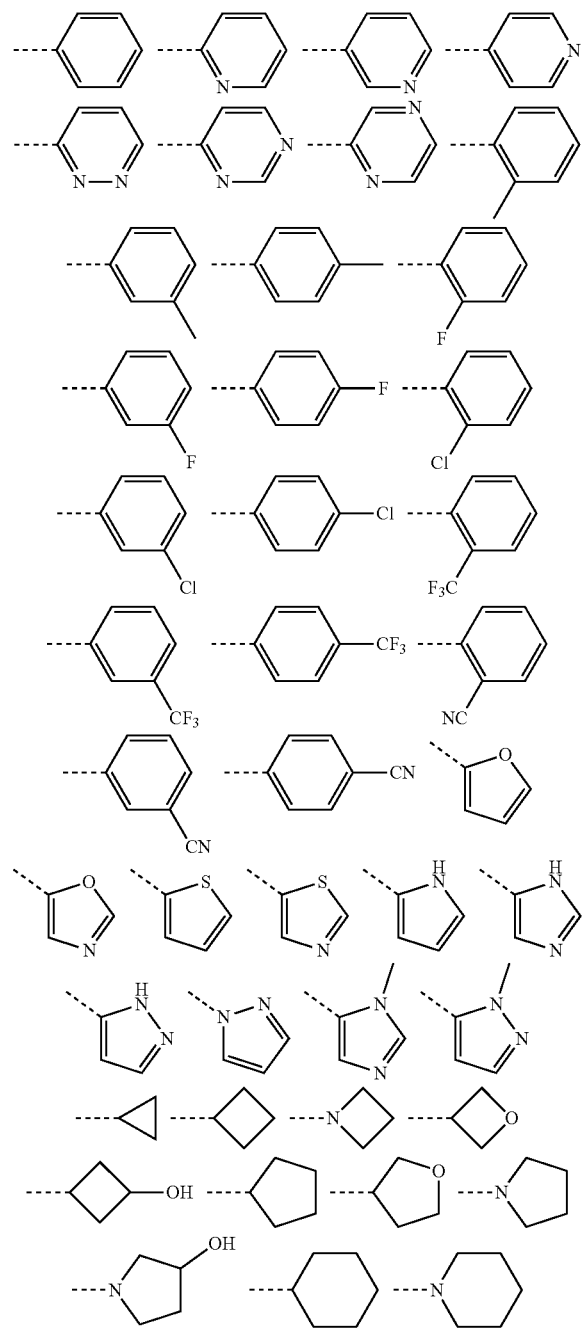
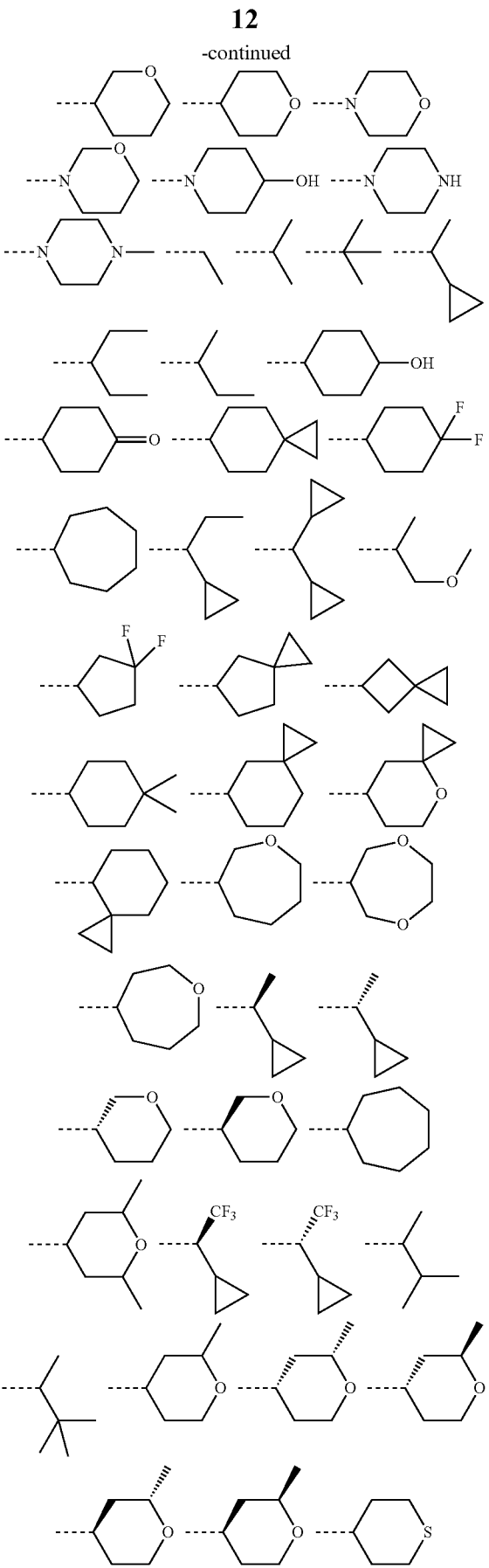

-continued
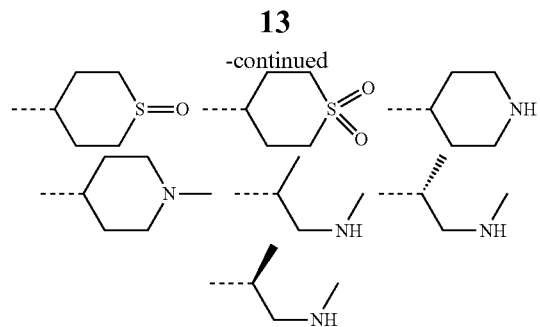
In some embodiments, $R_{13}$ is selected from the group consisting of:
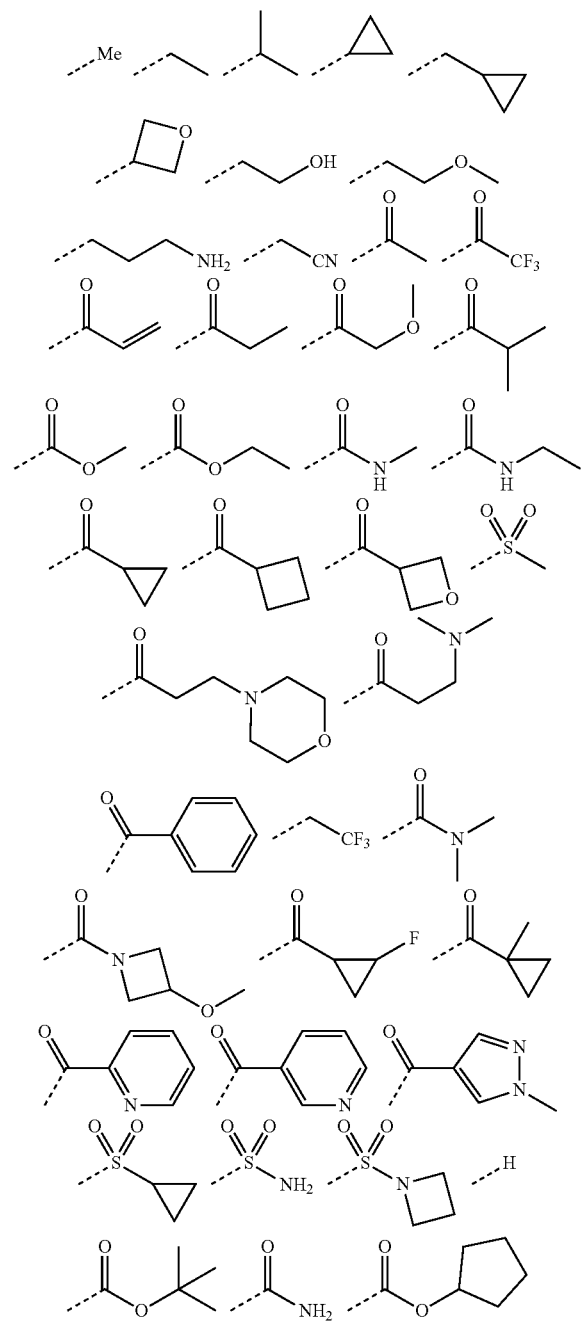
-continued
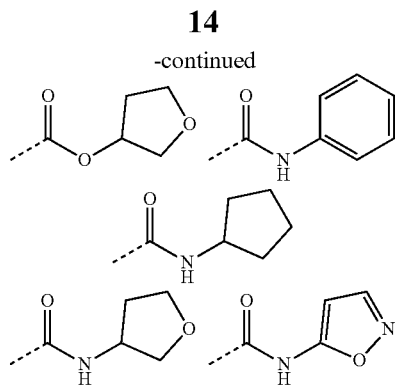
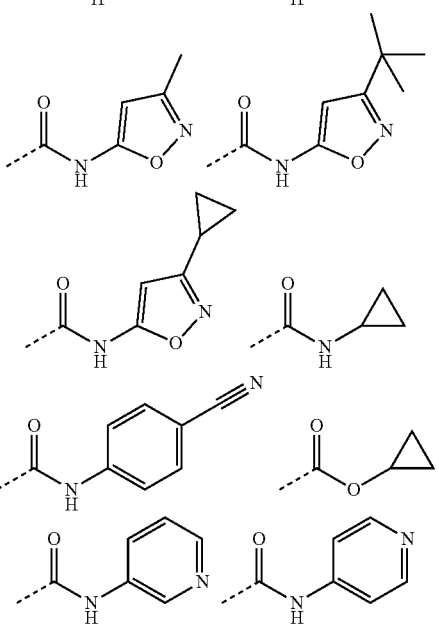
In some embodiments, L is $CH_2$, O or NH.
In some embodiments, the compound is selected from the group consisting of:
B1
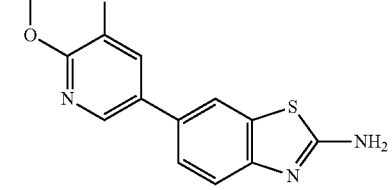
B2

B3
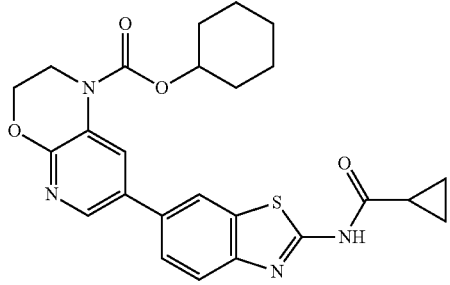
B4
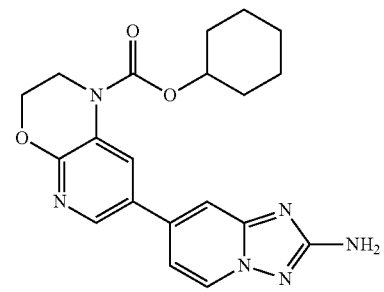
B5
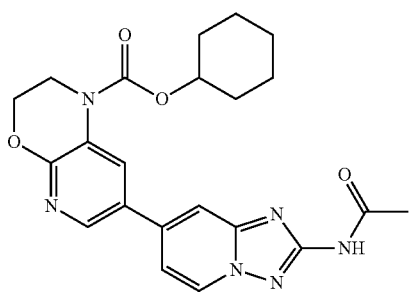
B6
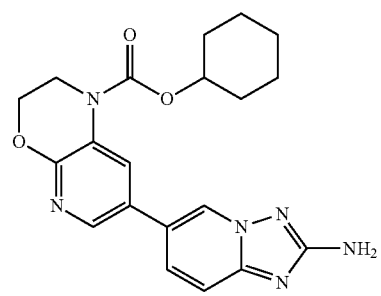
B7
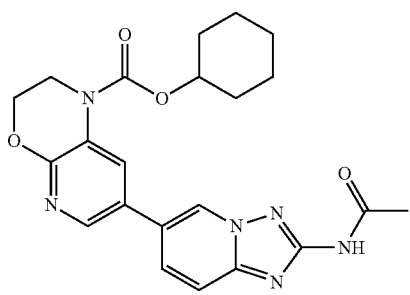
B8
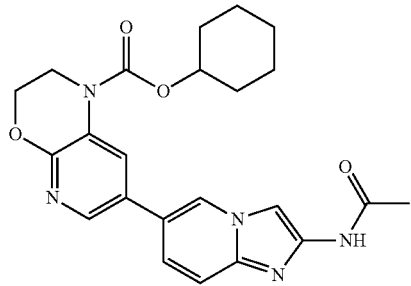
B9
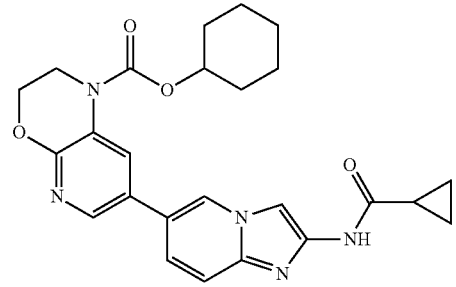
B10
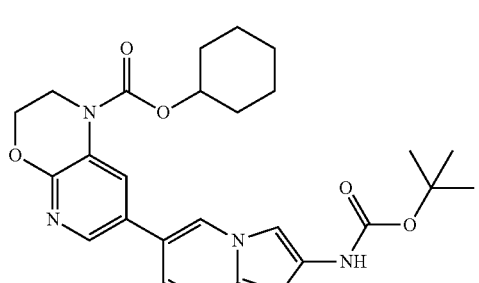
B11
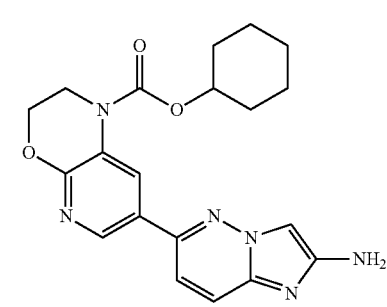
B12

B13 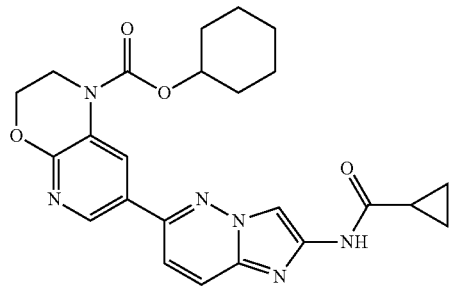
B14 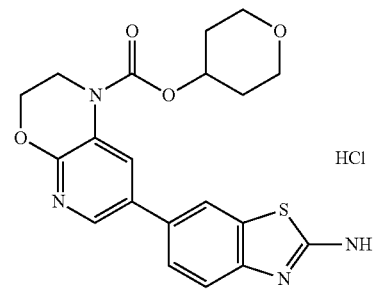
HCl
B15 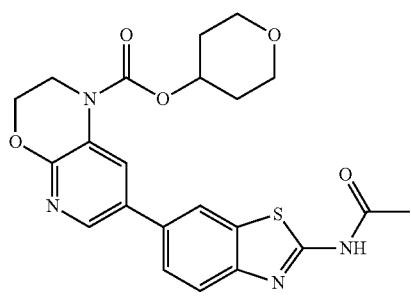
B16 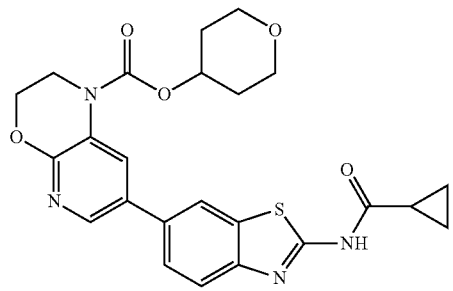
B17 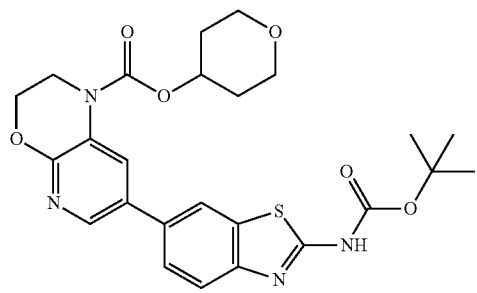
B18 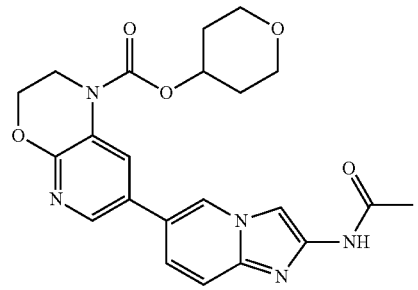
B19 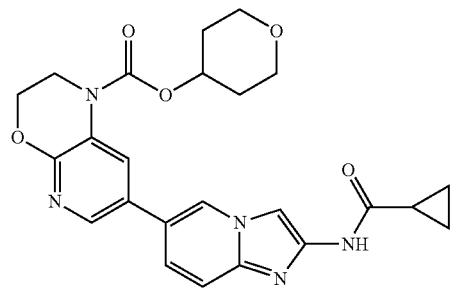
B20 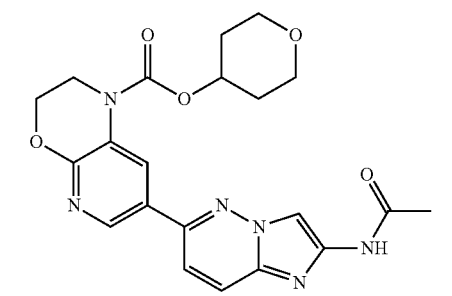
B21 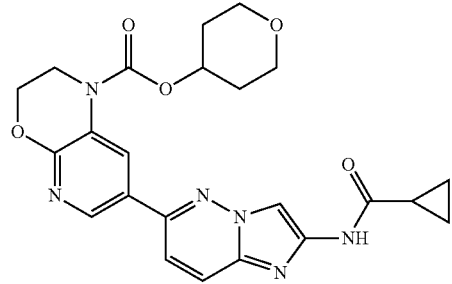
B22 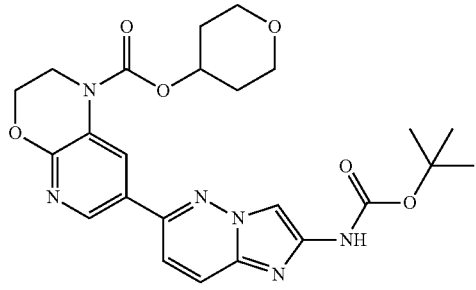

B23
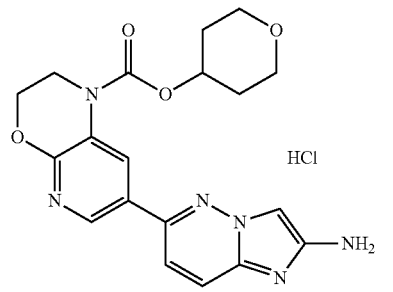
B24
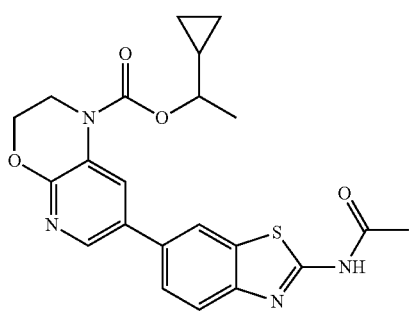
B25
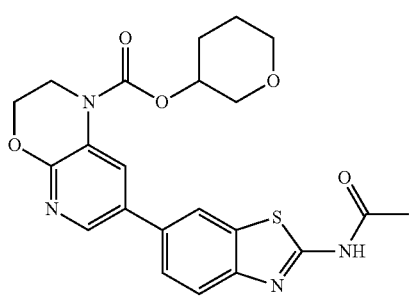
B26
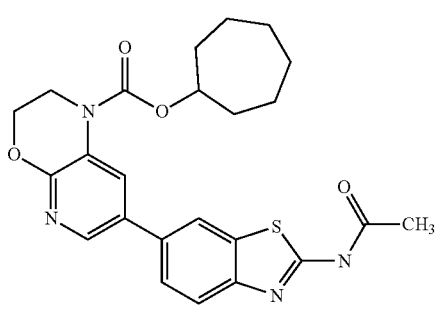
B27
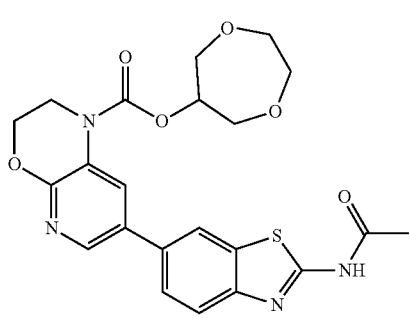
B28
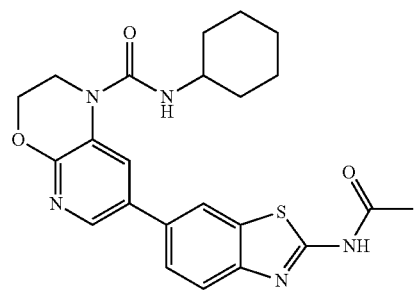
B29
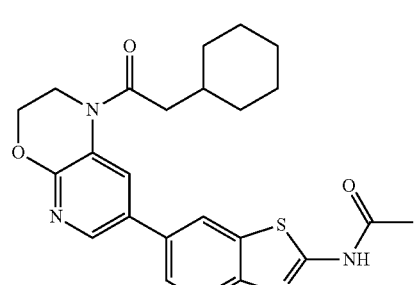
B30
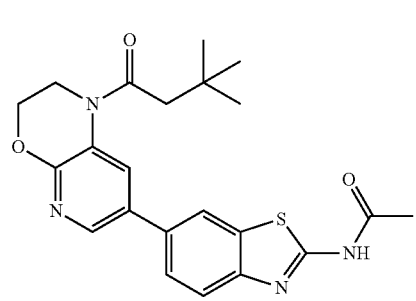
B31
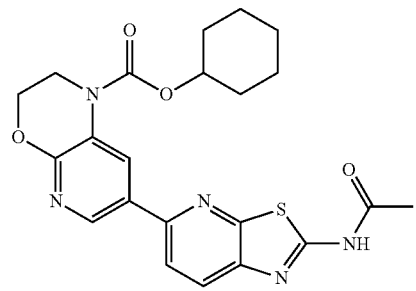
B32
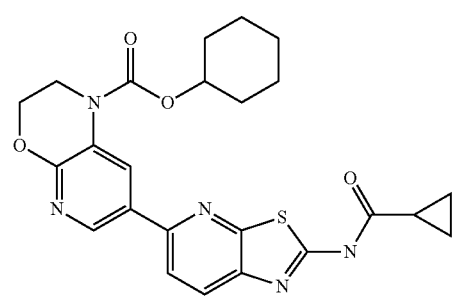

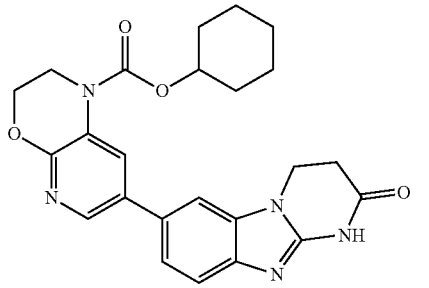
B33
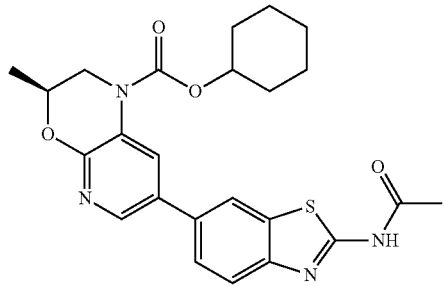
B38
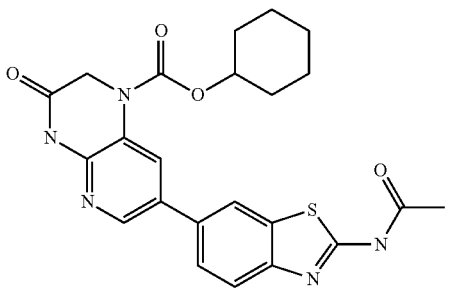
B39
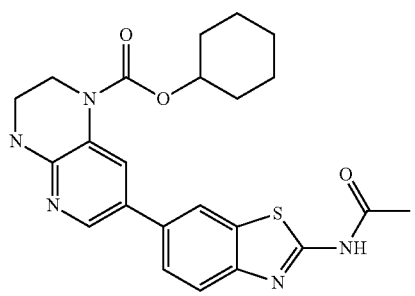
B40
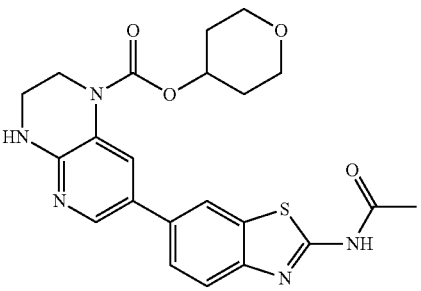
B41
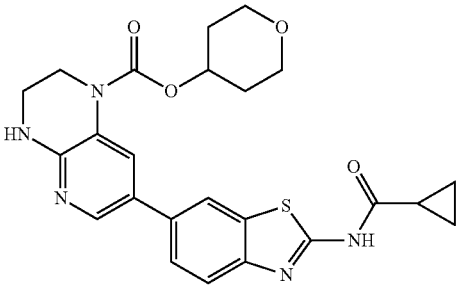
B42

B43
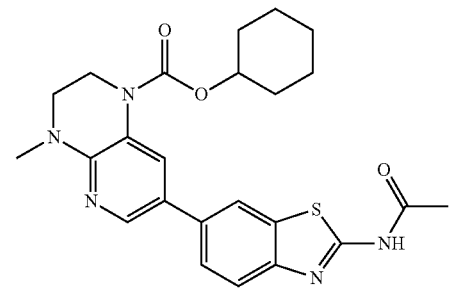
B44
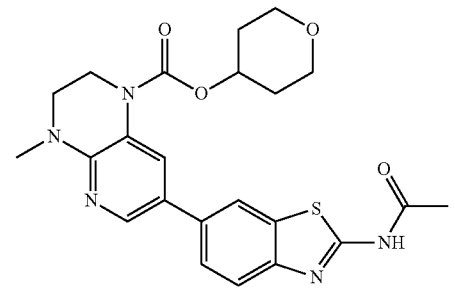
B45
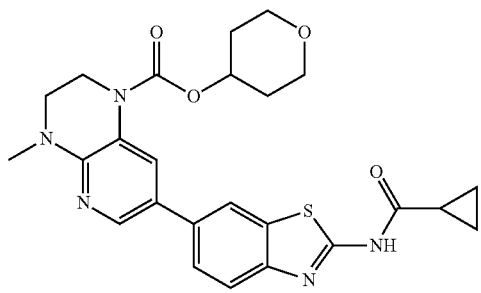
B46
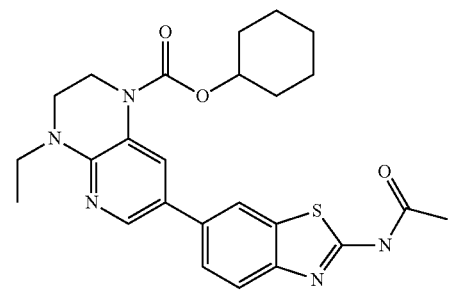
B47
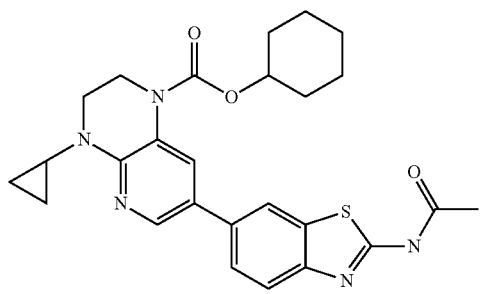
B48
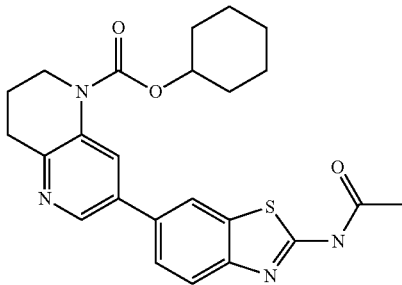
B49
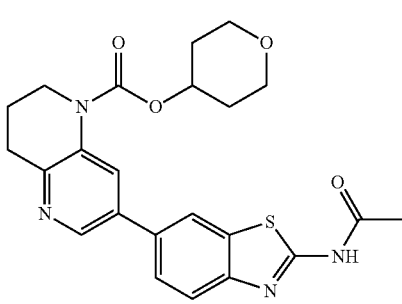
B50
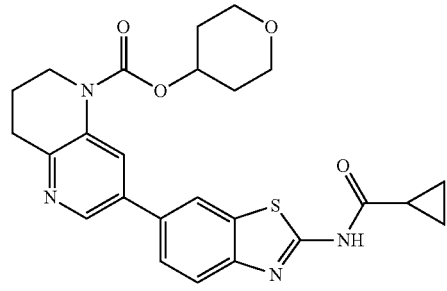
B51
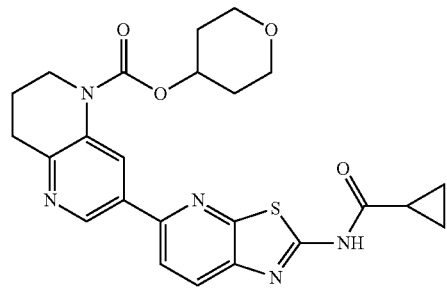
B52
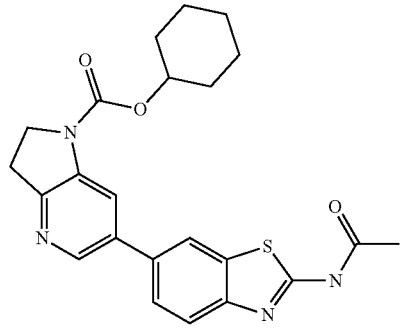

25
-continued
B53
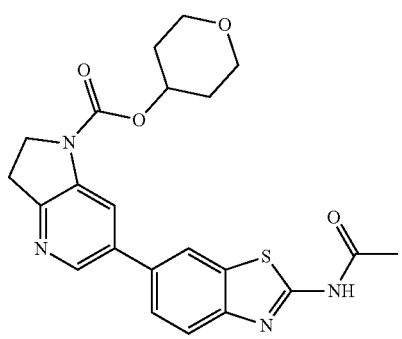
B54
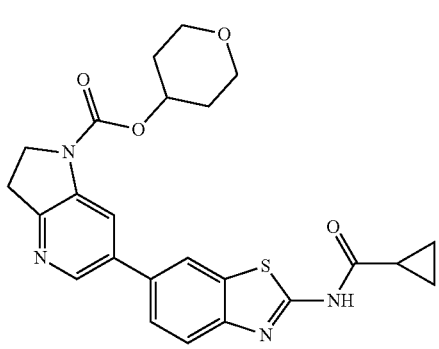
B55
B56
26
-continued
B57
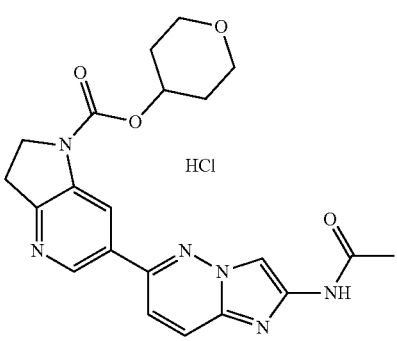
HCl
B58
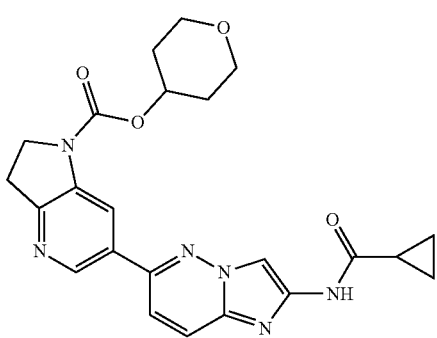
B59
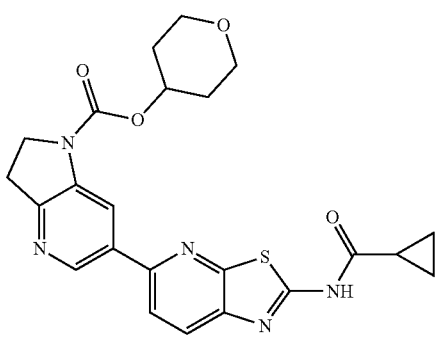
B60
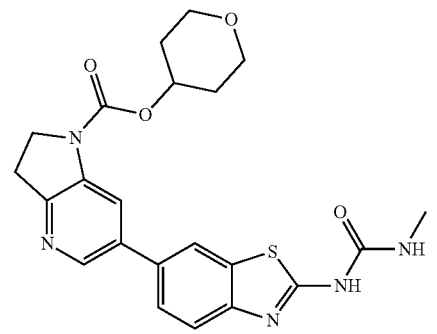

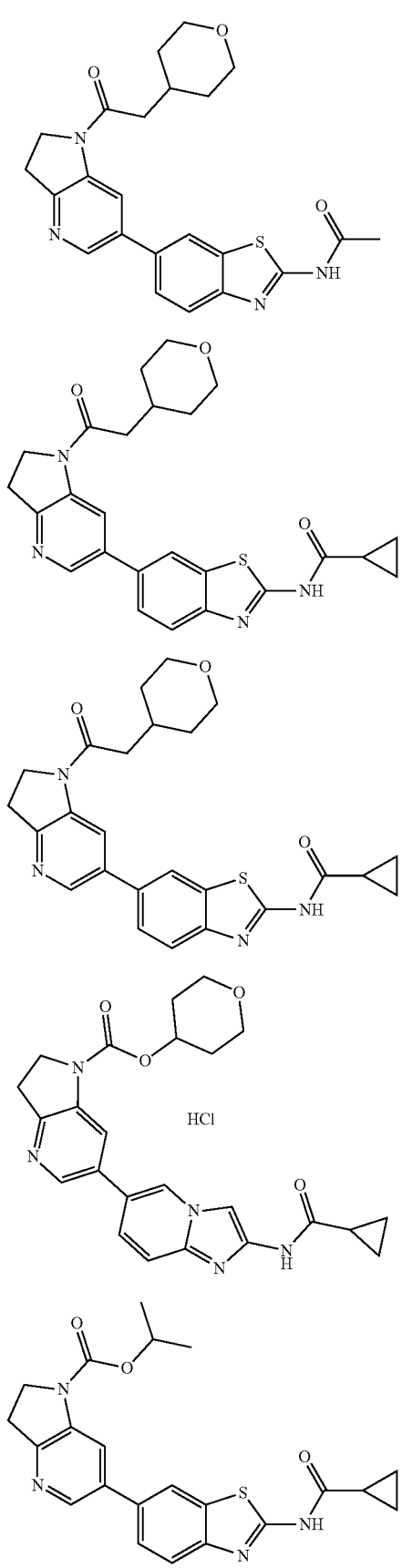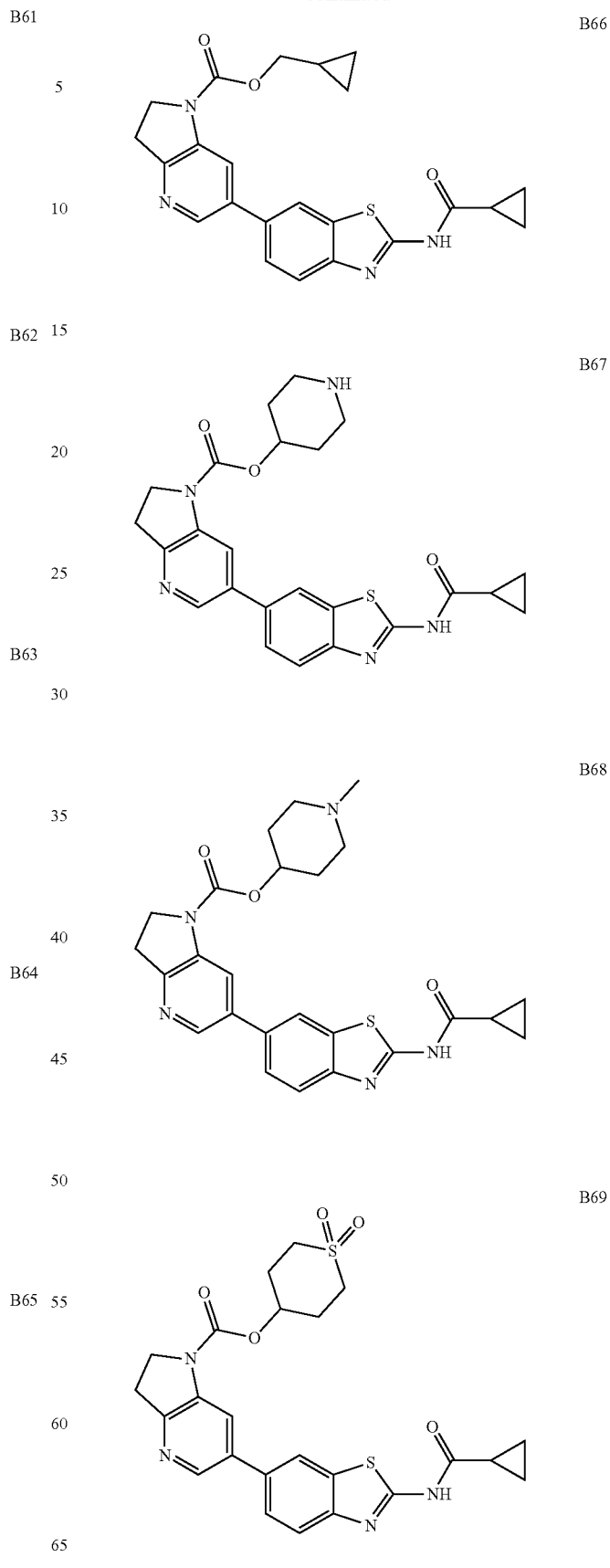

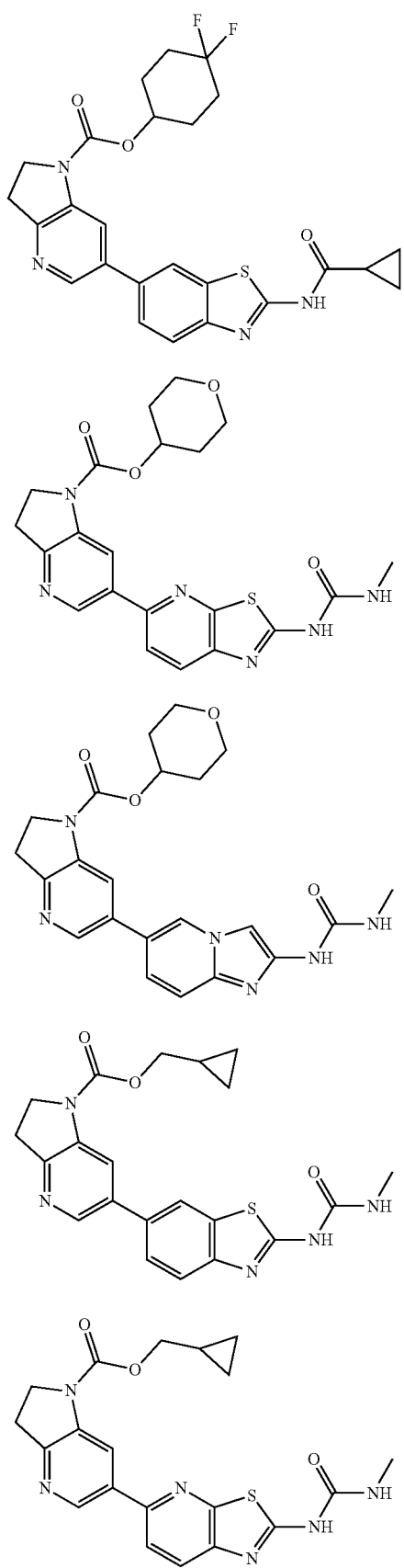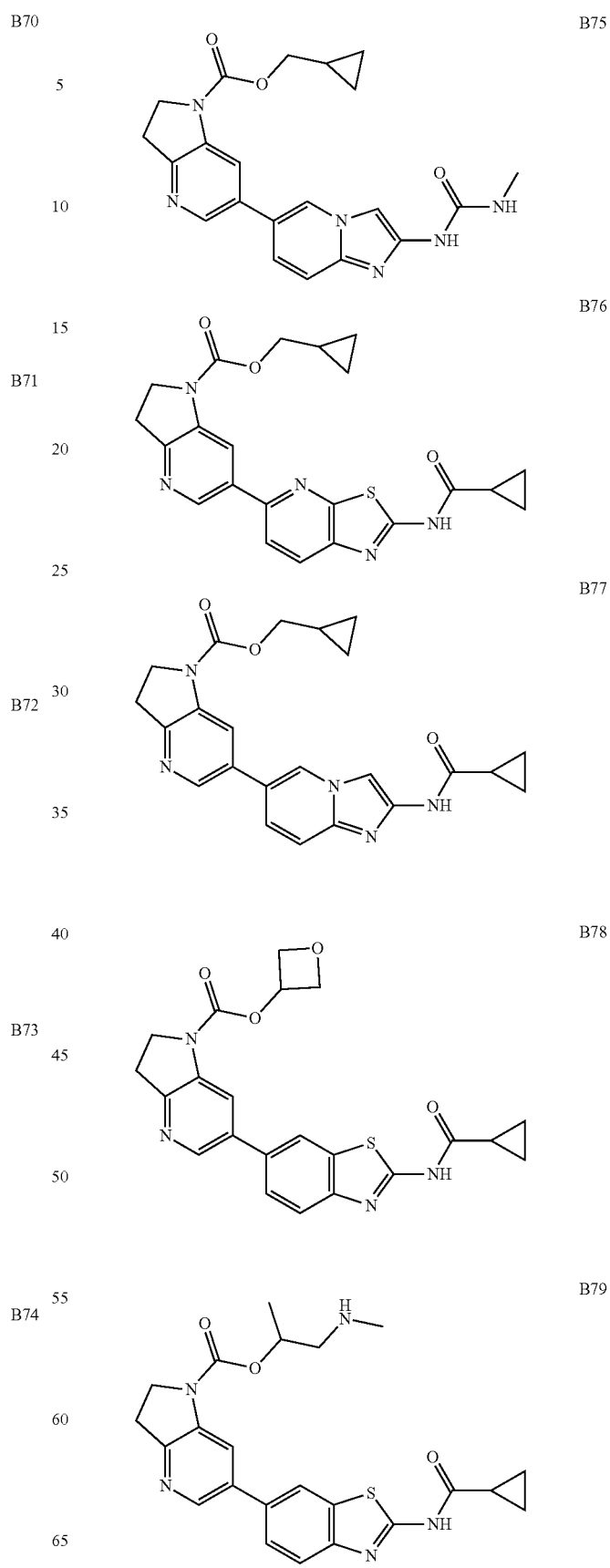

-continued

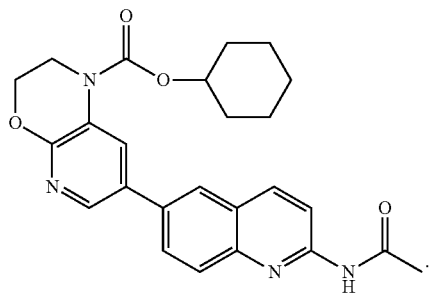

B80

Another aspect of the present disclosure provides a composition comprising a therapeutically effective amount of a compound of Formula (I) or any compound disclosed herein, and a pharmaceutically acceptable carrier, diluent, adjuvant or excipient.

Still another aspect of the present disclosure provides a method for treating a necrosis-related disorder in a mammal suffering therefrom, comprising administering to the mammal a therapeutically effective amount of at least one compound of Formula (I) or any compounds described herein, or the pharmaceutical composition described above, wherein the necrosis-related disorder is systematic inflammatory response, tumor, cancer, metabolic diseases or neurodegenerative diseases.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

Figure 1:
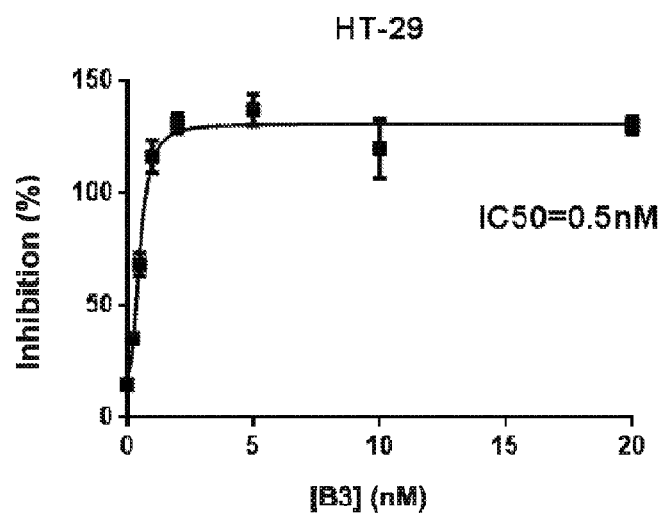
FIG. 1 depicts the inhibition of TNF-α induced-necrosis in HT29 cells by compound B3 in Example 19.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the singular forms "a," "an" and "the" include plural referents unless the context clearly dictates otherwise. Thus, for example, reference to "a molecule" includes a plurality of such molecules, and the like.

The term "about" or "nearly" as used herein generally refers to within +/−15%, 10%, 9%, 8%, 7%, 6%, 5%, 4%, 3%, 2%, or 1% of the designated amount.

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

The term "alkyl" as used herein generally refers to a straight or branched chain saturated aliphatic hydrocarbon. Alkyl groups include groups having from 1 to 8 carbon atoms ($C_1$-$C_8$ alkyl), from 1 to 6 carbon atoms ($C_1$-$C_6$ alkyl) and from 1 to 4 carbon atoms ($C_1$-$C_4$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

The term "alkenyl" as used herein generally refers to straight or branched chain alkene groups, which comprise at least one unsaturated carbon-carbon double bond. Alkenyl groups include $C_2$-$C_8$ alkenyl, $C_2$-$C_6$ alkenyl and $C_2$-$C_4$ alkenyl groups, which have from 2 to 8, 2 to 6 or 2 to 4 carbon atoms, respectively, including, for example, ethenyl, allyl or isopropenyl. The term "alkynyl" as used herein generally refers to straight or branched chain alkyne groups, which have one or more unsaturated carbon-carbon bonds, at least one of which is a triple bond. Alkynyl groups include $C_2$-$C_8$ alkynyl, $C_2$-$C_6$ alkynyl and $C_2$-$C_4$ alkynyl groups, which have from 2 to 8, 2 to 6 or 2 to 4 carbon atoms, respectively.

The term "cycloalkyl" as used herein generally refers to a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. For example, certain cycloalkyl groups are $C_3$-$C_7$ cycloalkyl, in which the cycloalkyl group contains a single ring having from 3 to 7 ring members, all of which are carbon. The term "cycloalkenyl" as used herein generally refers to a group that comprises one or more unsaturated rings in which all ring members are carbon.

The term "alkoxy" as used herein generally refers to an alkyl group as described above attached via an oxygen bridge. Alkoxy groups include $C_1$-$C_6$ alkoxy and $C_1$-$C_4$ alkoxy groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

The term "alkylamino" as used herein generally refers to a secondary or tertiary amine that has the general structure —NH—R1 or —N(R1)(R2), wherein R1 and R2 are selected independently from alkyl, cycloalkyl and (cycloalkyl)alkyl groups. Such groups include, but are not limited to, for example, mono- and di-($C_1$-$C_6$ alkyl)amino groups, in which each $C_1$-$C_6$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

The term "alkylthio" as used herein generally refers to an alkyl-substituted thio group, wherein the term alkyl is as defined above.

The term "halogen" or "halide" as used herein generally refers to fluorine, chlorine, bromine, and iodine. The term "haloalkyl" as used herein generally refers to an alkyl group that is substituted with one or more independently chosen halogens (e.g., "$C_1$-$C_6$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

The term "heteroaryl" as used herein generally refers to an aromatic group in which at least one aromatic ring comprises at least one heteroatom selected from N, O and S. Heteroaryls include, for example, 5-12 membered heteroaryls. Examples included but are not limited to imidazole, furan, furazan, isothiazole, isoxazole, oxadiazole, oxazole, pyrazine, pyrazole, pyridazine, pyridine, pyrimidine, tetrazole, thiazole and thiophene.

The term "heterocyclic" as used herein generally refers to a ring structure containing 3-12 ring atoms, in which at least one ring atom is carbon and at least one ring atom is heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

The terms "substituent" and "substituted," as used herein, generally denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom.

A straight chain substituent may be a moiety such as a halogen, alkyl group, haloalkyl group or other group that is covalently bonded to an atom (preferably a carbon or nitrogen atom) that is a member of a straight chain.

The term "bicycloheteroalkyl" as used herein generally refers to a double ring structure which shares one or two atoms and which comprise at least one hetero atom independently selected from the group consisting of N, O, and S in the ring. The term "bicycloheteroalkylene" as used herein generally refers to a di-radical of bicycloheteroalkyl group, which may bind to two other groups.

The term "cycloalkylamine" as used herein generally refers to either a ring structure with an amino group attached to a carbon atom in the ring or a ring structure with a nitrogen atom as member of the ring.

The term "cycloalkylamide" as used herein generally refers to either a ring structure with an amid group attached to a carbon atom in the ring via the amide carbon or a ring structure with both the amide nitrogen and amide carbon atoms becoming members of the ring.

The term "cyclourea" as used herein generally refers to a ring structure with the urea carbon and both urea nitrogen atoms becoming members of the ring. One example of cyclourea is oxoimidazolidine.

The term "pharmaceutically acceptable" as used herein generally refers to a form of the compound that is safe for administration to a subject. For example, a free base, a salt form, a solvate, a hydrate, a prodrug or derivative form of a compound of formula I, which has been approved for mammalian use, via oral ingestion or any other route of administration, by a governing authority or regulatory agency, such as the Food and Drug Administration (FDA) of the United States, is pharmaceutically acceptable.

Included in the compounds of Formula (I) are the pharmaceutically acceptable salt forms of the free-base compounds. The term "pharmaceutically-acceptable salts" as used herein generally refers to salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of Formula (I) is used to treat a subject by administering the compound(s) as a pharmaceutical composition. To this end, the compound (s), in one embodiment, is combined with one or more pharmaceutically acceptable excipients, including carriers, diluents or adjuvants, to form a suitable composition, which is described in more detail herein.

The term "excipient" as used herein generally refers to any pharmaceutically acceptable additive, carrier, adjuvant, or other suitable ingredient, other than the active pharmaceutical ingredient (API), which is typically included for formulation and/or administration purposes.

The term "diluent" as used herein generally refers to an agent used as filler in order to achieve the desired composition volume or weight. The diluent may be present in the pharmaceutical composition within granules in the form of a single compound or in the form of a mixture of compounds. Non-limiting examples of diluent include lactose, starch, pregelatinized starch, microcrystalline cellulose, silicified microcrystalline cellulose, cellulose acetate, dextrose, mannitol, sodium phosphate, potassium phosphate, calcium phosphate, fructose, maltose, sorbitol, or sucrose.

The term "adjuvant," as used herein generally refers to any substance or mixture of substances that increases the efficacy or potency of a compound disclosed herein on a target where the adjuvant is used together with the compound disclosed herein. However, when the adjuvant is used alone, no pharmacological effect is observed on the same target.

The terms "treat", "treating," "treatment," and "therapy" as used herein generally refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" as used herein generally refers to quantifying the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Pharmaceutical Compositions/Formulations

One embodiment provides a pharmaceutical composition comprising a compound of formula I, or a stereoisomer, tautomer, hydrate, solvate or pharmaceutically acceptable salt thereof, and at least one pharmaceutically acceptable excipient.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: *The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of formula I with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Synthetic Methods

Methods of the present invention may include the use of at least one compound of Formula (I), which inhibits necrosis in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of necrosis may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

All reagents and solvents were obtained commercially unless stated otherwise. All commercial reagents and solvent were used without purification unless stated otherwise. When required, some reagents and solvents were purified by standard techniques. For example, tetrahydrofuran may be purified by distillation from sodium. All thin-layer chromatography (TLC, GF254) analyses and column purification (100-200 mesh) were performed on silica gel (Qingdao Haiyang Chemical Co. Ltd. or Yantai Chemical Co. Ltd.), using petroleum ether (b.p. 60-90° C.)/ethyl acetate (v/v) as eluent; and spots revealed by UV visualization at 254 nm and $I_2$ vapor or phosphomolybdic acid. All organic layers after extraction were dried over anhydrous $Na_2SO_4$ unless stated otherwise. All nuclear magnetic resonance spectra were recorded using a Bruck-400 spectrometer at 400 MHz using TMS as an internal standard. LC-MS was run using an Agilent 1100 system with LC-MSDTrap recorder, diode array detector (DAD) with detecting wavelength at 214 nm and 254 nm, and ESI source. The HPCL column is an Agela Durashell C18 3.5 µm 4.6×50 mm column. Gradients were run using 0.1 $NH_4HCO_3$ aqueous solution and acetonitrile with gradient 5/95 to 95/5 in the run time indicated (for example, 5 min), flow rate at 1.8 m/min.

The size and scale of the synthetic methods will vary depending on the desired amount of end product. It is understood that while specific reactants and amounts are provided in the Examples, one of skill in the art knows other alternative and equally feasible sets of reactants that will also yield the same compounds. Thus, where general oxidizers, reducers, solvents of various nature (aprotic, apolar, polar, etc.) are utilized, equivalents will be known in the art and are herein contemplated for use in the present methods.

Many of the steps below indicate various work-ups following termination of the reaction. A work-up involves generally quenching of a reaction to terminate any remaining catalytic activity and starting reagents. This is generally followed by addition of an organic solvent and separation of the aqueous layer from the organic layer. The product is typically obtained from the organic layer and unused reactants and other spurious side products and unwanted chemicals are generally trapped in the aqueous layer and discarded. The work-up in standard organic synthetic procedures found throughout the literature is generally followed by drying the product by exposure to a drying agent, such as anhydrous $Na_2SO_4$, to remove any excess water or aqueous byproducts remaining partially dissolved in the organic layer and concentration of the remaining organic layer. Concentration of product dissolved in solvent may be achieved by any known means, such as evaporation under pressure, evaporation under increased temperature and pressure, and the like. Such concentrating may be achieved by use of standard laboratory equipment such as rotary-evaporator distillation, and the like. This is optionally followed by one or more purification steps which may include, but is not limited to, flash column chromatography, filtration through various media and/or other preparative methods known in the art and/or crystallization/recrystallization. (See, for instance, Addison Ault, "Techniques and Experiments for Organic Chemistry," 6th Ed., University Science Books, Sausalito, Calif., 1998, Ann B. McGuire, Ed., pp. 45-59).

General Synthetic Routes

The following Methods A-F are embodiments for some general synthetic routes leading to compounds of Formula (I). Detailed reaction conditions for each Method can be found in the examples shown vide infra.

Method A:

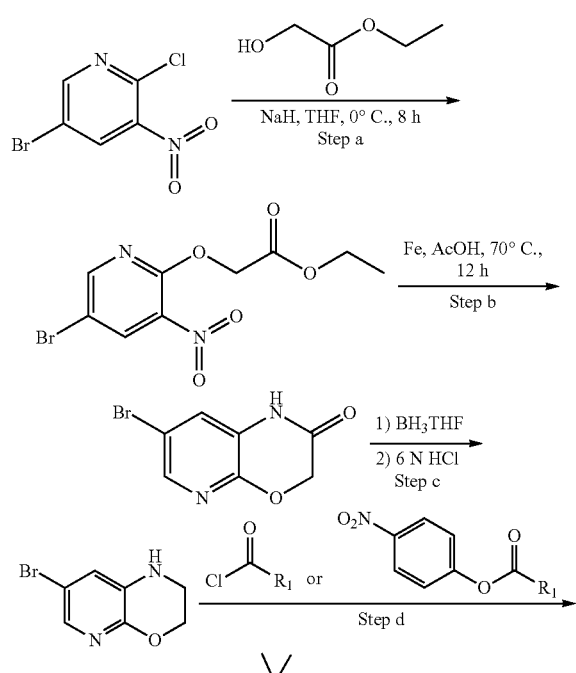

The starting material 5-bromo-2-chloro-3-nitro-pyridine can undergo a displacement reaction in Step a to introduce the 2-ethoxy-2-oxo-ethoxy side chain for the ensuing ring closure in Step b. Subsequently the amide group is reduced to afford an amino group in Step c. The secondary amine is then acylated using various acylation reagents in Step d to form a protected 7-bromo-2,3-dihydropyrido[2,3-b][1,4]oxazin for Suzuki coupling reaction in Step e to afford a compound of Formula (I). Following the general chemistry depicted in Method A, compounds B1, B2, B3, B15, B16, B24, B25, B26, B28, B29, B30, and B36 in Table 1 have been synthesized.

Method B:

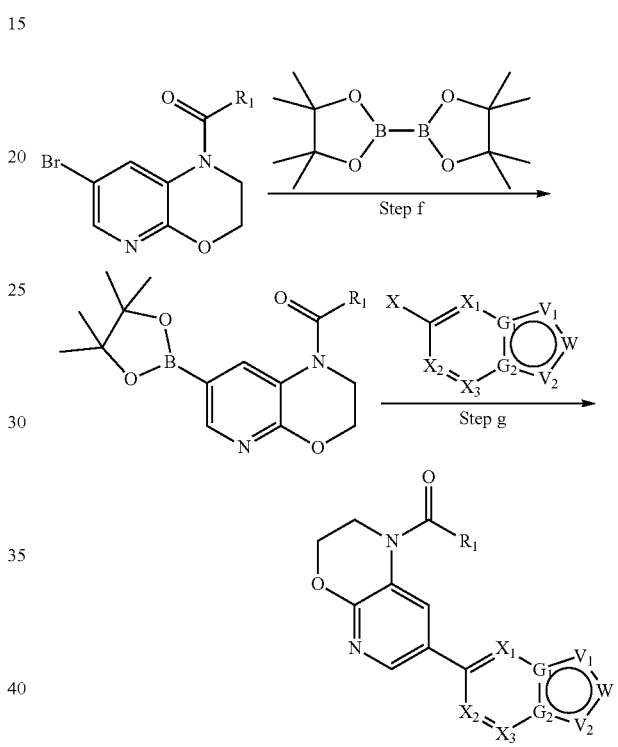

A protected 7-bromo-2,3-dihydropyrido[2,3-b][1,4]oxazin can undergo a Miyaura borylation reaction to give a boronated product in Step f. The boronate product can react with a heteroaryl halide or sulfonate in a Suzuki coupling reaction to afford a compound of Formula (I). Following the general chemistry depicted in Method B, compounds B4, B5, B6, B7, B8, B9, B10, B11, B12, B13, B17, B18, B19, B20, B21, B22, B27, B31, B32, and B35 in Table 1 have been synthesized.

Method B':

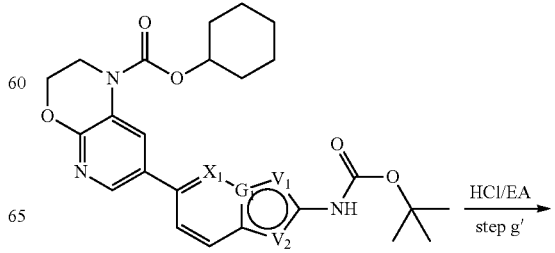

-continued

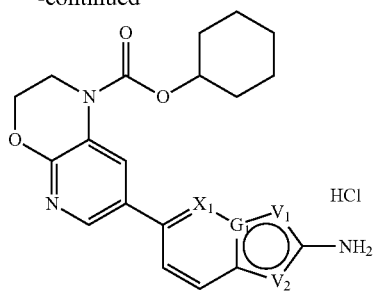

Method B' is used to remove the tert-butyloxycarbonyl protecting group (t-Boc) from an amine under a selective deprotection conditions to afford a compound of Formula (I) bearing a free amine. Notably, another carbamate moiety on another amino group is intact during the deprotection. Following the general chemistry depicted in Method B', compound B14 in Table 1 has been synthesized.

Method C:

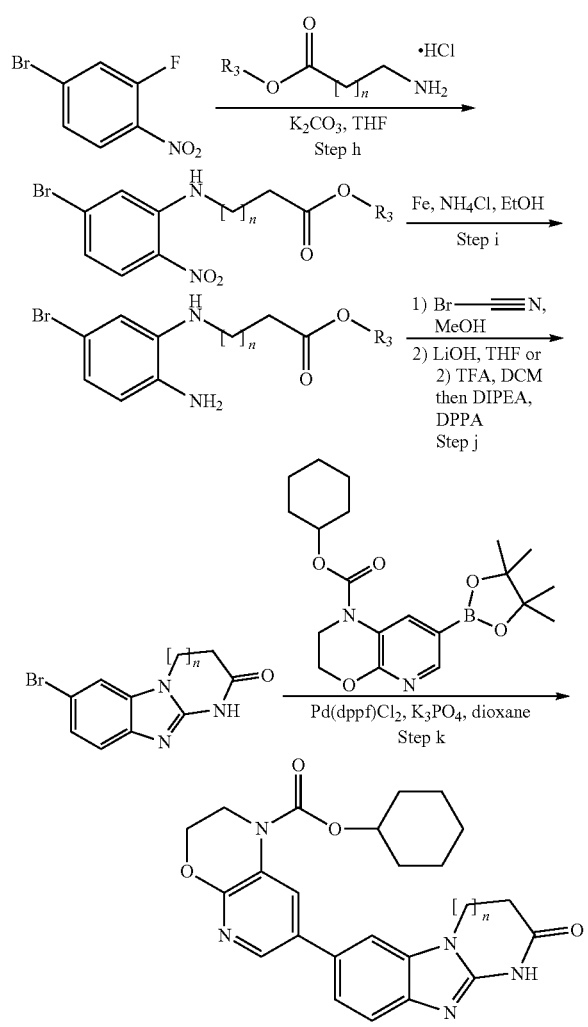

n = 0, 1

A nucleophilic aromatic substitution on 4-bromo-2-fluoro-1-nitro-benzene in Step h can afford an aniline molecule. The nitro group can then be reduced in Step i to provide another primary amine adjacent to the other amino group. The diamine can react with cyanogen bromide to form 2-aminobenzimidazole derivative followed by an intramolecular amide formation in Step j. Then the bromide undergoes Suzuki coupling to afford a compound of Formula (I). Following the general chemistry depicted in Method C, compounds B33 and B34 in Table 1 have been synthesized.

Method D:

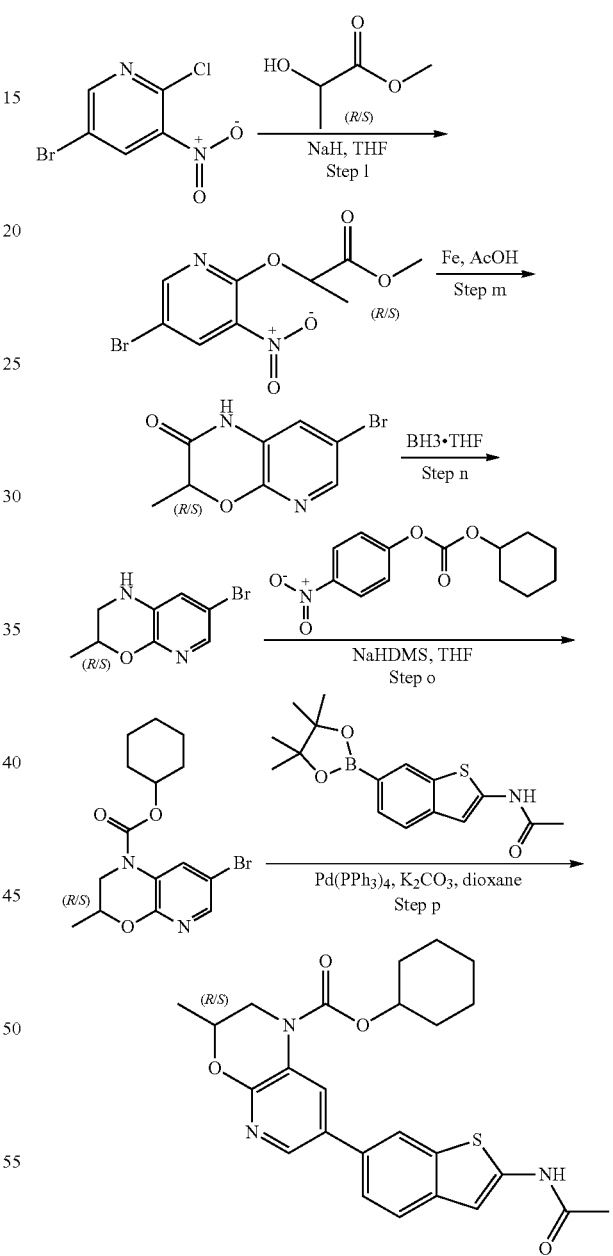

A nucleophilic aromatic substitution on 5-bromo-2-chloro-3-nitro-pyridine in Step 1 can afford an intermediate, whose nitro group can then be reduced in Step m to provide 7-bromo-3-methyl-3,4-dihydro-1H-1,5-naphthyridin-2-one after an intramolecular acylation step. The secondary amine is then acylated in Step o. The bromide undergoes Suzuki coupling to afford a compound of Formula (I). Following the general chemistry depicted in Method D, compounds B37 and B38 in Table 1 have been synthesized.

Method E:

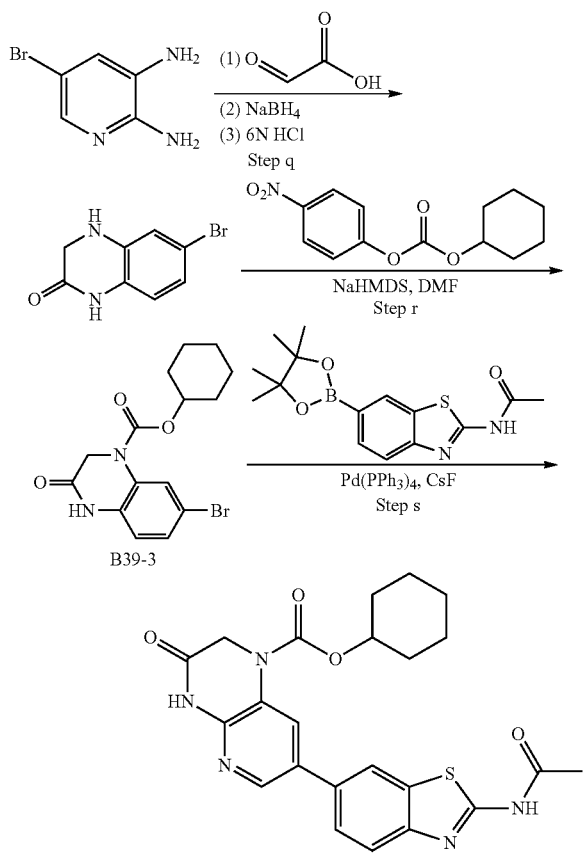

6-Bromo-3,4-dihydro-1H-quinoxalin-2-one can be made from a diamine in Step q via a reductive amination and intramolecular amide formation. Further acylation of the secondary amine in Step r can form the carbamate compound B39-3. The bromide undergoes Suzuki coupling in Step s to afford a compound of Formula (I). Following the general chemistry depicted in Method E, compound B39 in Table 1 has been synthesized.

Method F:

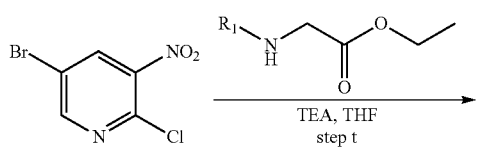

-continued

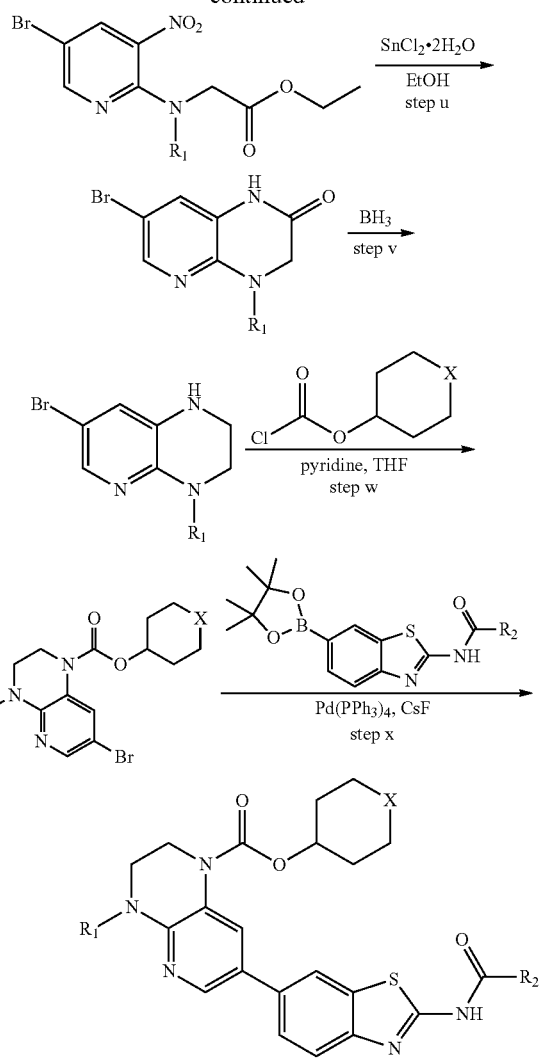

A nucleophilic aromatic substitution in Step t can afford an intermediate, whose nitro group can then be reduced in Step u to provide 7-bromo-3,4-dihydro-1H-pyrido[2,3-b]pyrazin-2-one derivative after an intramolecular acylation step. The amide group is reduced in Step v to provide a 7-bromo-1,2,3,4-tetrahydropyrido[2,3-b]pyrazine derivative. The secondary free amine is then acylated in Step w. The bromide undergoes Suzuki coupling to afford a compound of Formula (I). Following the general chemistry depicted in Method F, compounds B40, B41, B42, and B47 in Table 1 have been synthesized.

Method G:

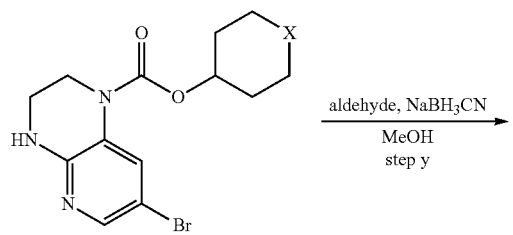

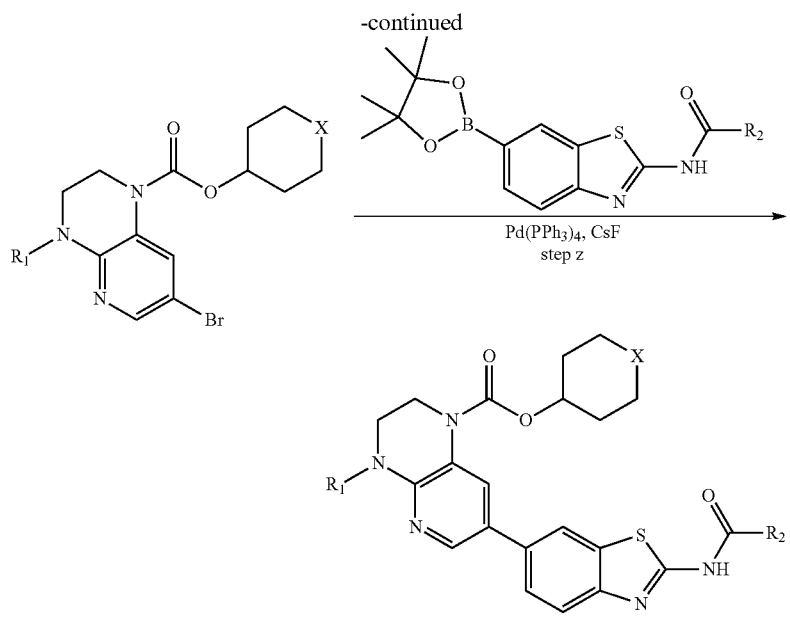

A reductive amination in Step y affords a bromide intermediate, which undergoes Suzuki coupling to afford a compound of Formula (I). Following the general chemistry depicted in Method G, compounds B43, B44, B45, and B46 in Table 1 have been synthesized.

Method H:

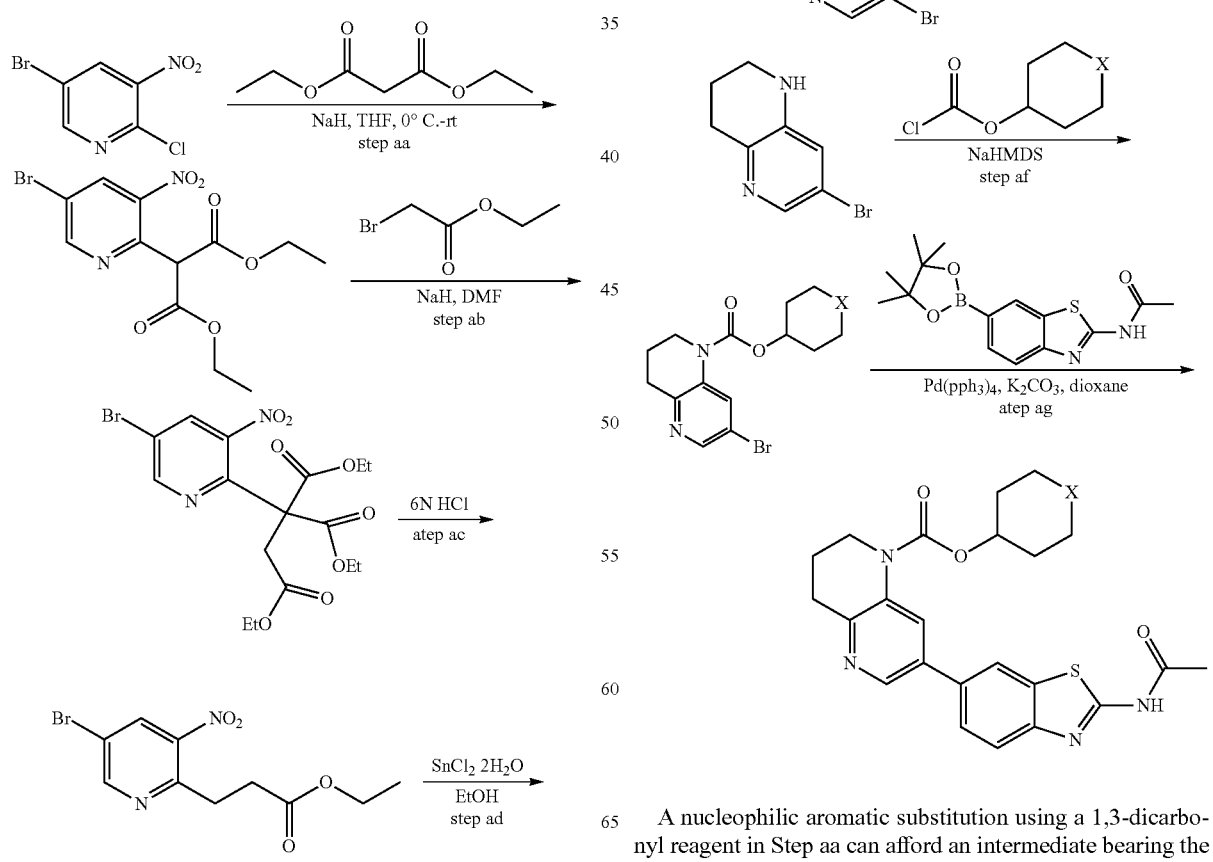

A nucleophilic aromatic substitution using a 1,3-dicarbonyl reagent in Step aa can afford an intermediate bearing the 1,3-dicarbonyl moiety to undergo another alkylation after deprotonate the acidic proton in step ab. Following decarboxylation in Step ac and reduction/amide formation in Step ad, the amide is reduced in Step ae. The secondary amine is then acylated in Step af. The bromide undergoes Suzuki coupling reaction in Step ag to afford a compound of Formula (I). Following the general chemistry depicted in Method H, compounds B48 and B49 in Table 1 have been synthesized.

Method I:

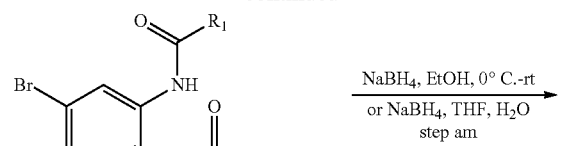

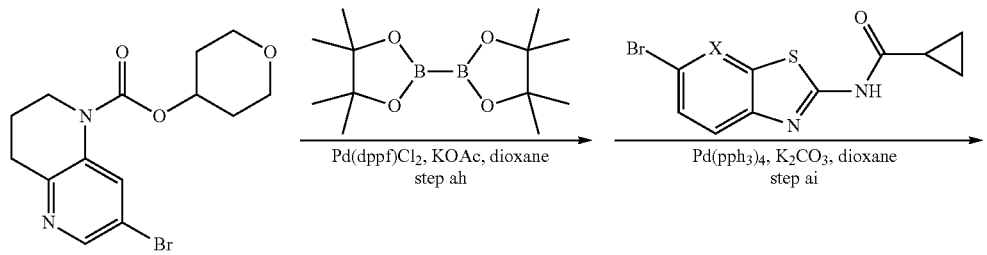

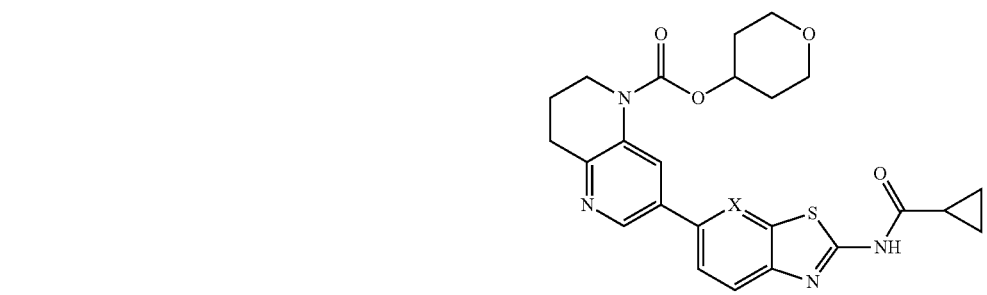

A protected bromide can undergo a Miyaura borylation reaction to give a boronated product in Step ah. The boronate product can react with a heteroaryl halide or sulfonate in a Suzuki coupling reaction at Step ai to afford a compound of Formula (I). Following the general chemistry depicted in Method I, compounds B50 and B51 in Table 1 have been synthesized.

Method J:

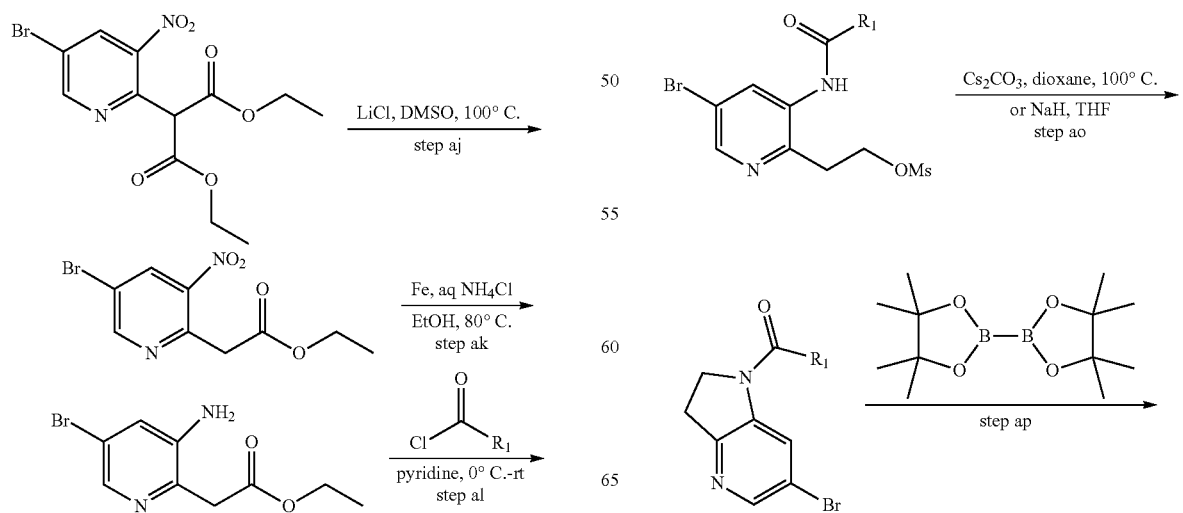

-continued

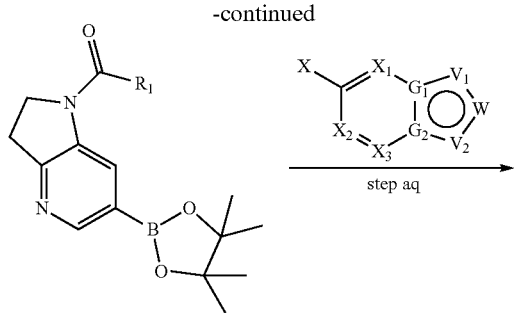

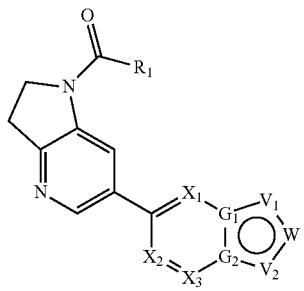

A 1,3-dicarbonyl moiety can undergo decarboxylation in Step aj. Then the nitro group can be reduce to an aniline in Step ak. The aniline group can be acylated in Step al. The ester group is reduced to an alcohol in Step am followed by a conversion of (the alcohol group to a mesylate group in Step an. A basic treatment in Step ao facilitates an intramolecular displacement of the mesylate group to afford a 6-bromo-2,3-dihydro-1H-pyrrolo[3,2-b]pyridine derivative, which undergoes a Miyaura borylation reaction to give a boronated product in Step ah. The boronate product can react with a heteroaryl halide or sulfonate in a Suzuki coupling reaction at Step aq to afford a compound of Formula (I). Following the general chemistry depicted in Method J, compounds B55, B56, B57, B58, B59, B63, B64, B71, B72, B73, B74, B75, B76, and B77 in Table 1 have been synthesized.

Method K:

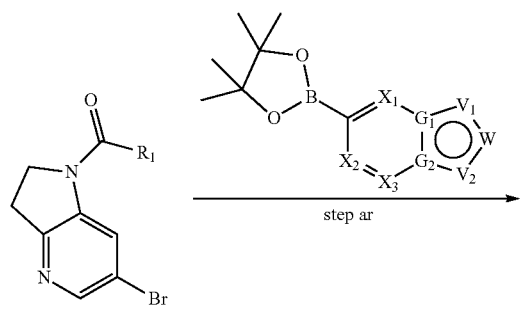

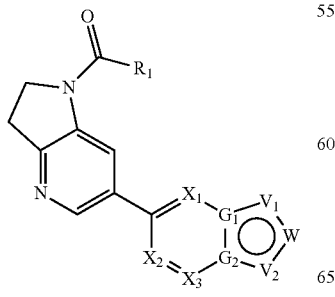

A protected bromide can undergo a Suzuki coupling reaction at Step ar to afford a compound of Formula (I). Following the general chemistry depicted in Method K, compounds B52, B53, B54, B61, B62, B65, B66, 69, B70, and B78 in Table 1 have been synthesized.

Method L:

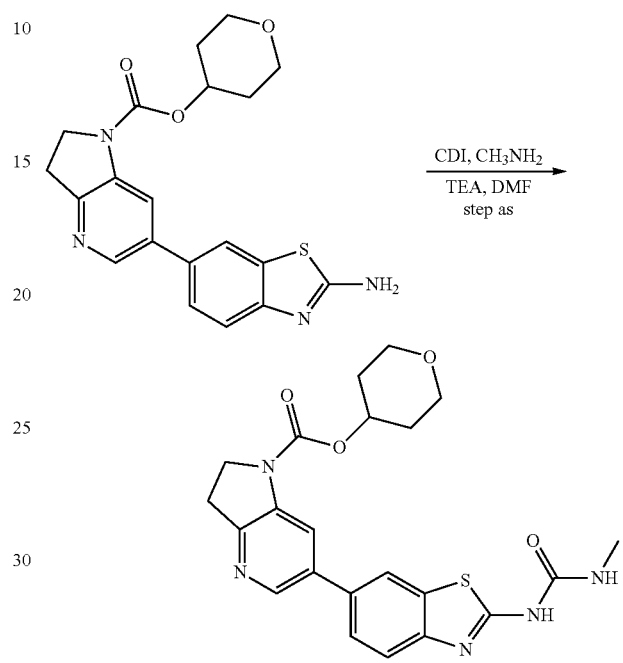

A free primary amine can undergo an acylation reaction at Step as to afford a compound of Formula (I). Following the general chemistry depicted in Method L, compound B60 in Table 1 has been synthesized.

Method M:

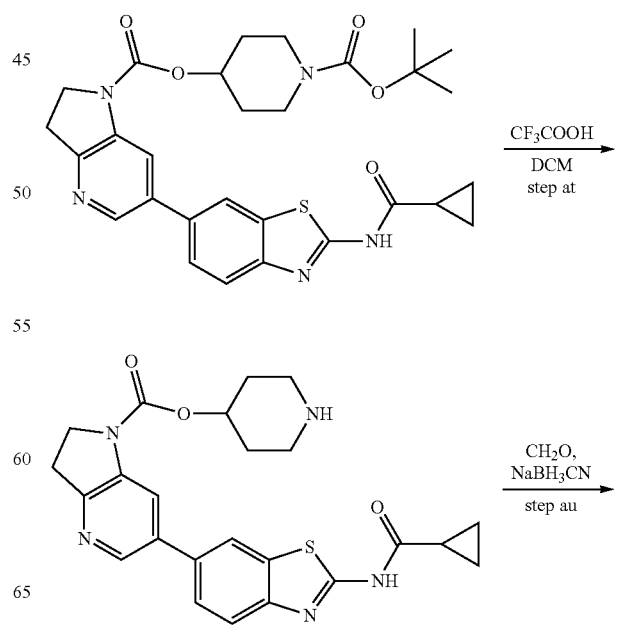

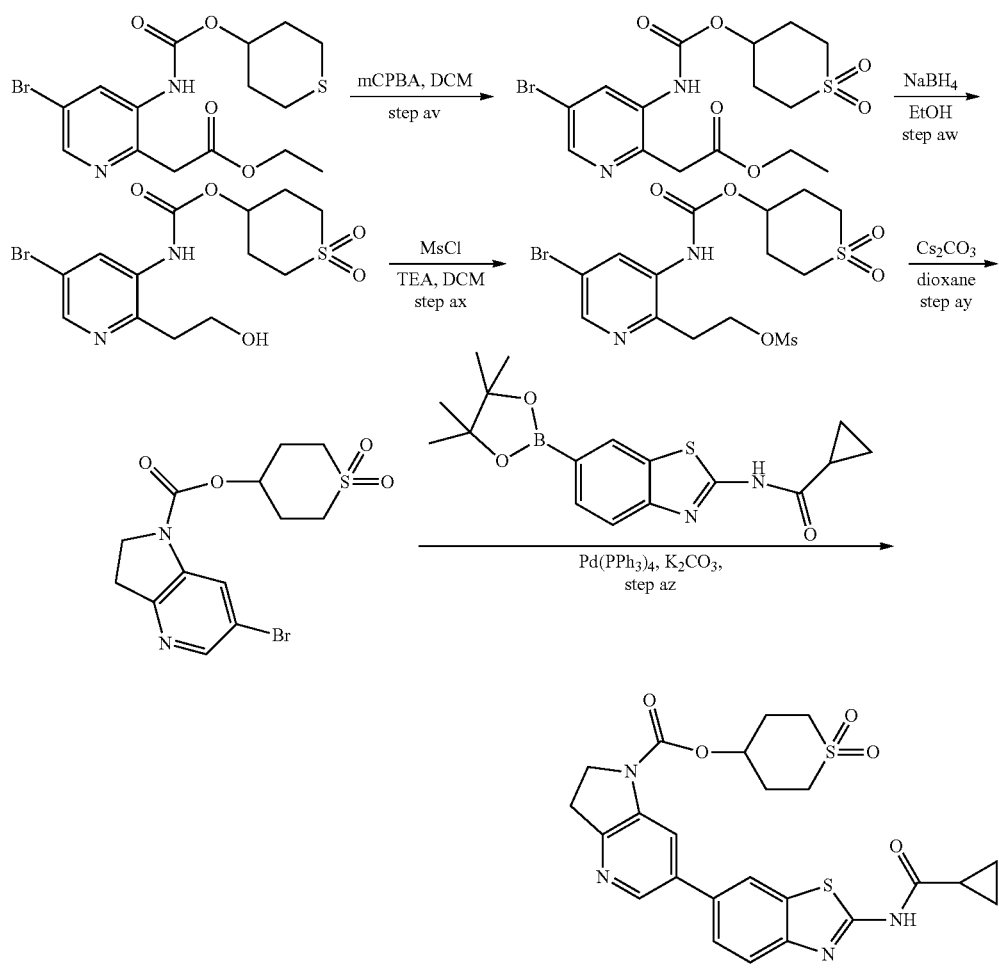

A t-Boc protecting group is removed in Step at under acidic conditions to give a free secondary amine, which is alkylated under reductive amination in Step au to afford a compound of Formula (I). Following the general chemistry depicted in Method M, compounds B67 and B68 in Table 1 have been synthesized.

Method N:

A tetrahydrothiopyran group is oxidized to the corresponding sulfone in Step av. The ester group is reduced to an alcohol in Step aw and the free alcohol is converted to a mesylate in Step ax. Intramolecular displacement by the amino group forms the 6-bromo-2,3-dihydro-1H-pyrrolo[3,2-b]pyridine derivative in Step ay. A Suzuki coupling reaction in Step az can afford a compound of Formula (I).

Following the general chemistry depicted in Method N, compound B69 in Table 1 has been synthesized.

Method O:

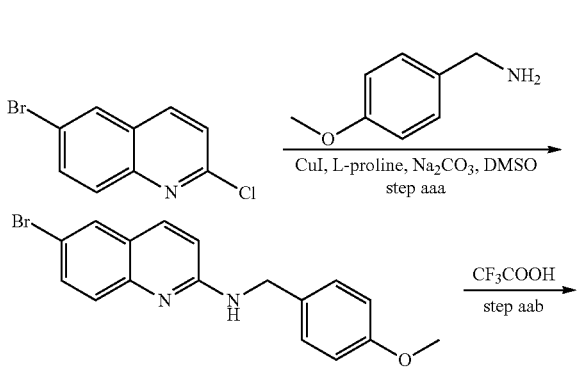

-continued

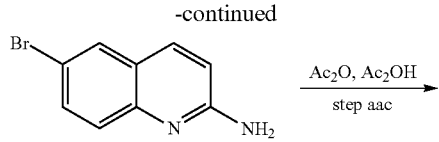

-continued

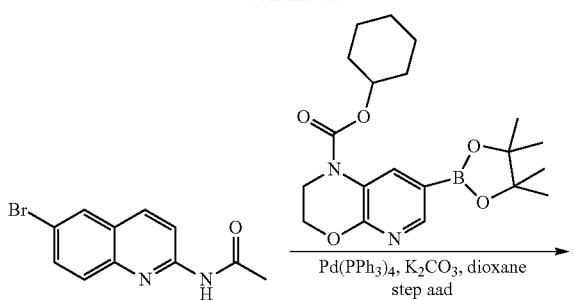

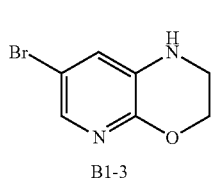

B1-3

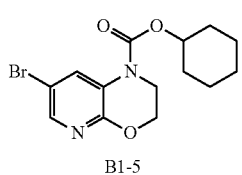

B1-5

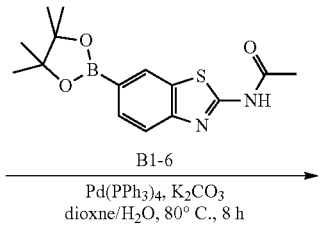

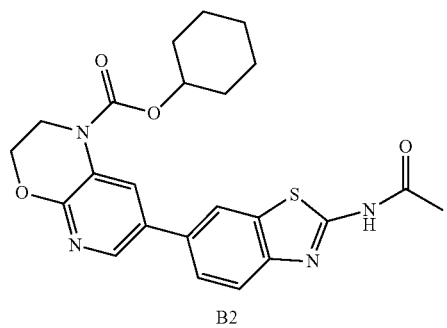

B2

A copper-catalyzed nucleophilic aromatic substitution or Ullmann-type reaction in Step aaa can form a 6-bromoquinolin-2-amine derivative, which can be deprotected in Step aab to afford 6-bromoquinolin-2-amine. Acylation in Step aac and Suzuki coupling reaction in Step aad forms a compound of Formula (I). Following the general chemistry depicted in Method O, compound B80 in Table 1 has been synthesized.

Example 1: Compound B2 Made by Method A

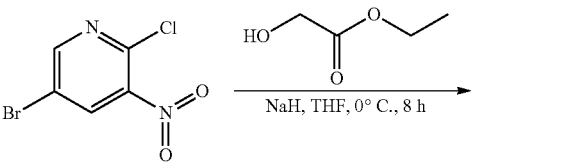

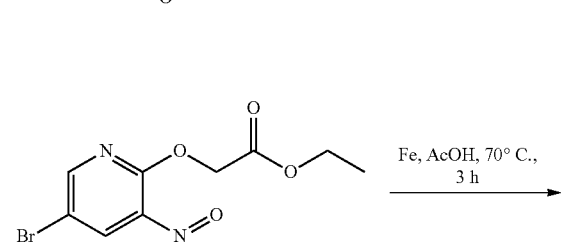

B1-1

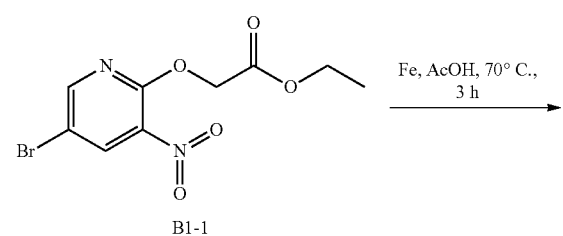

B1-2

Step 1: 1) Ethyl-2-((5-bromo-3-nitropyridin-2-yl)oxy)acetate (B1-1)

To a solution of 5-bromo-2-chloro-3-nitropyridine (6.0 g, 25.4 mmol) and ethyl 2-hydroxyacetate (2.9 g, 28.0 mmol) in THF (150 mL) was added slowly 60% NaH (1.3 g, 1.8 mmol) at 0° C. The mixture was stirred at room temperature for 8 h. After water (20 mL) was added to quench the reaction, the mixture was treated with brine (100 mL) and extracted with ethyl acetate (50 mL*2). The combined organic layers were dried over $Na_2SO_4$, filtered and concentrated. Then the solid was filtered to give the title compound as a yellow solid (5.5 g 71%). $^1H$ NMR (400 MHz, $CDCl_3$) δ 8.46 (d, J=2.0 Hz, 1H), 8.39 (d, J=1.6 Hz, 1H), 5.05 (s, 2H), 4.26-4.17 (m, 2H), 1.28 (t, J=7.2 Hz, 3H).

Step 2: 7-bromo-1H-pyrido[2,3-b][1,4]oxazin-2(3H)-one (B1-2)

To a solution of B1-1 (5.0 g, 16 mmol) in acetic acid (80 mL) was added slowly Fe (5.5 g, 98 mmol) at 70° C. The mixture was stirred at 70° C. for 3 h. After cooling to room temperature, the mixture was filtered and evaporated to remove most of acetic acid. The residue was poured into 1N HCl (100 mL). The resulting suspension was filtered, the filter-cake was dried to give the title compound as a white solid (3.3 g, 91%). $^1H$ NMR (400 MHz, DMSO-$d_6$) δ 10.94 (s, 1H), 7.88 (s, 1H), 7.33 (s, 1H), 4.81 (s, 2H).

Step 3: 7-bromo-2,3-dihydro-1H-pyrido[2,3-b][1,4]oxazine (B1-3)

To a solution of a B1-2 (3.3 g, 14 mmol) in $BH_3$.THF (42 mL, 42 mmol) was stirred at 80° C. for 3 h. After cooling to room temperature, the solvent of the mixture was removed and the residue was dissolved in 3N HCl (25 mL). The mixture was stirred continued at 110° C. for 5 h. It was adjusted pH to 8 by 3N NaOH and extracted with ethyl acetate (50 mL*3). The organic layers were dried over Na$_2$SO$_4$, filtered and concentrated. It was obtained the title compound as a white solid (2.5 g, 83%). $^1$H NMR (400 MHz, DMSO-d$_6$) δ 7.38 (s, 1H), 7.02 (s, 1H), 6.36 (s, 1H), 4.24 (s, 2H), 3.27 (s, 2H).

Step 4: cyclohexyl-7-bromo-2,3-dihydro-1H-pyrido[2,3-b][1,4]oxazine-1-carboxylate (B1-5)

A mixture of B1-3 (2.0 g, 9.3 mmol), DIPEA (5.6 g, 36 mmol) and B1-4 (3.0 g, 18.3 mmol) in toluene (50 mL) was stirred at 80° C. for 1 h. After cooling to room temperature, the mixture was treated with brine (50 mL) and extracted with ethyl acetate (50 mL*2). The combined organic layers were dried over Na$_2$SO$_4$, filtered and concentrated. The residue was purified by silica gel column chromatography (petroleum ether/ethyl acetate=10/1) to give the title compound as a brown oil (2.8 g, 93%). $^1$H NMR (400 MHz, CDCl$_3$) δ 8.53 (s, 1H), 7.97 (s, 1H), 4.85 (s, 1H), 4.38 (d, J=3.8 Hz, 3H), 3.91 (d, J=3.8 Hz, 2H), 2.0 (m, 10H).

Step 5: Cyclohexyl-7-(2-acetamidobenzo[d]thiazol-6-yl)-2,3-dihydro-1H-pyrido[2,3-b][1,4]oxazine-1-carboxylate (B2)

A mixture of B1-5 (53 mg, 0.16 mmol), B1-6 (330 mg, 1.0 mmol), Pd(PPh$_3$)$_4$ (18 mg, 0.016 mmol), K$_2$CO$_3$ (75 mg, 0.5 mmol) and H$_2$O (1 mL) in dioxane (7 mL) was stirred at 80° C. under N$_2$ overnight. The mixture was evaporated and the residue was purified by silica gel column chromatography (dichloromethane/methanol=100/1) to give the title compound as a white solid (15 mg, 23%). $^1$H NMR (400 MHz, DMSO-d$_6$) δ 12.40 (s, 1H), 8.62 (s, 1H), 8.24 (d, J=5.9 Hz, 2H), 7.81 (d, J=8.4 Hz, 1H), 7.65 (d, J=8.3 Hz, 1H), 4.79 (s, 1H), 4.41 (s, 2H), 3.92 (s, 2H), 2.21 (s, 3H), 1.87 (s, 2H), 1.67 (s, 2H), 1.60-1.44 (m, 3H), 1.36 (dd, J=22.1, 9.8 Hz, 3H.

Example 2: Compound B17 Made by Methods A and B

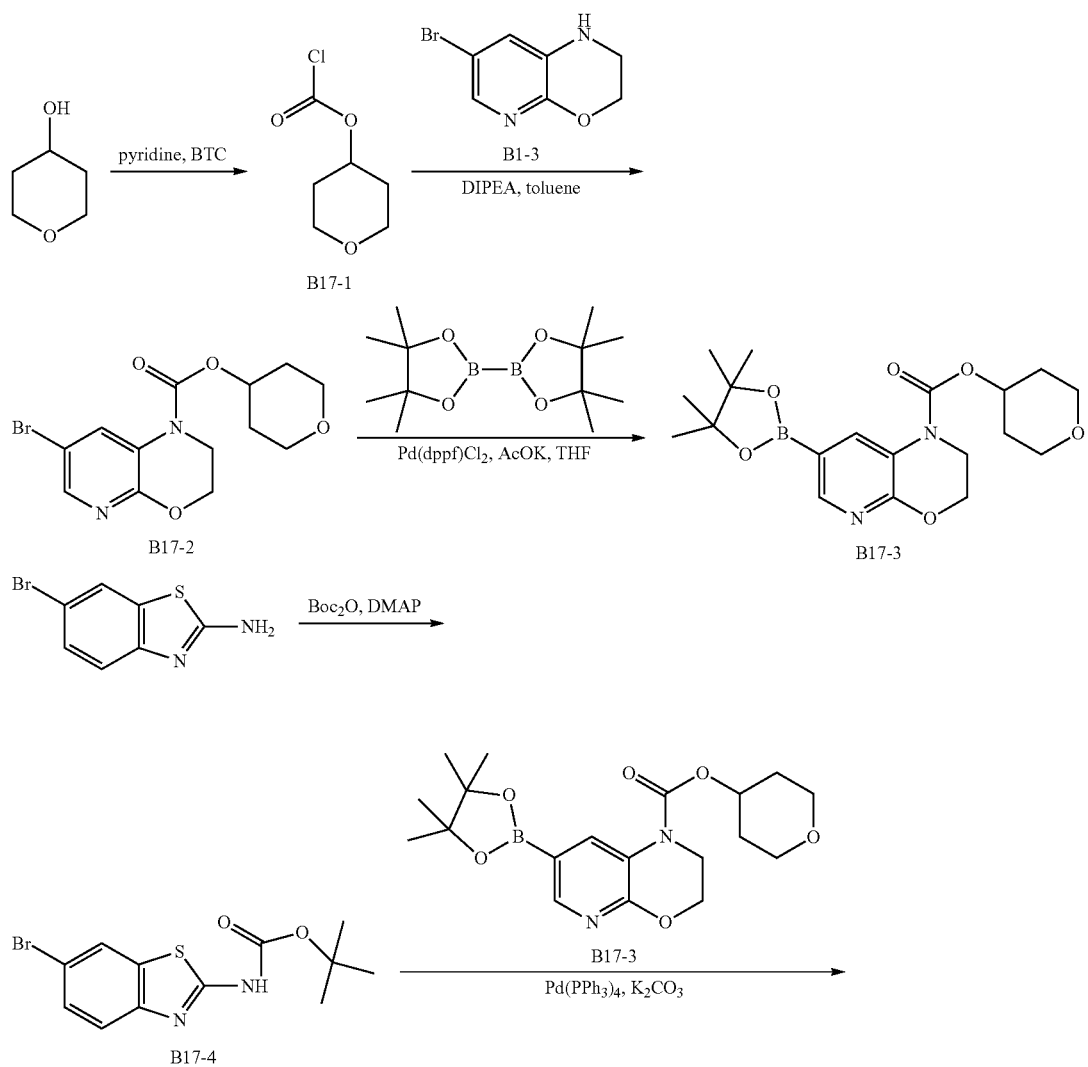

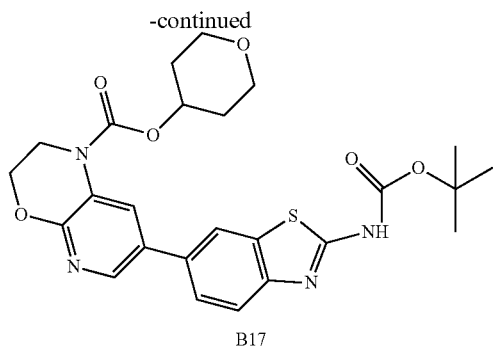

B17

Step 1: tetrahydro-2H-pyran-4-yl carbonochloridate (B17-1)

To a solution of bis(trichloromethyl)carbonate (23.7 g, 80 mmol) in 200 mL of dichloromethane was added dropwise pyridine (13.4 g, 220 mmol) at 0° C. After stirring for 10 min, a solution of tetrahydro-2H-pyran-4-ol (20.4 g, 200 mmol) in dichloromethane (50 mL) was added slowly. After the mixture was stirred for 1 h, the resulting solution was filtered. The filtrate was evaporated to give the crude title compound as a colorless oil (35 g).

Step 2: tetrahydro-2H-pyran-4-yl-7-bromo-2,3-dihydro-1H-pyrido[2,3-b][1,4]oxazine-1-carboxylate (B17-2)

A mixture of B1-3 (2.2 g, 10 mmol), DIPEA (12.9 g, 100 mmol) and B17-1 (4.9 g, 30 mmol) in toluene (70 mL) was stirred at 80° C. for 1 h. After cooling to room temperature, the mixture was treated with brine (50 mL) and extracted with ethyl acetate (50 mL*2). The combined organic layers were dried over $Na_2SO_4$, filtered and concentrated. The residue was purified by silica gel column chromatography (petroleum ether/ethyl acetate=2/1) to give the title compound as a brown oil (3.1 g, 91%).

Step 3: tetrahydro-2H-pyran-4-yl-7-(4,4,5,5-tetramethyl-1,3,2-dioxaborolan-2-yl)-2,3-dihydro-1H-pyrido[2,3-b][1,4]oxazine-1-carboxylate (B17-3)

A mixture of B17-2 (3.0 g, 8.8 mmol), 4,4,4',4',5,5,5',5'-octamethyl-2,2'-bi(1,3,2-dioxaborolane) (2.5 g, 9.7 mmol), KOAc (1.7 g, 17.6 mmol) and Pd(dppf)$Cl_2$ (482 mg, 0.6 mmol) in THF (100 mL) was stirred at 80° C. under $N_2$ overnight. After cooling to room temperature, the mixture was filtered and evaporated to give the crude title compound as a black oil (5 g).

Step 4: tert-butyl(6-bromobenzo[d]thiazol-2-yl)carbamate (B17-4)

A mixture of 6-bromobenzo[d]thiazol-2-amine (500 mg, 2.8 mmol), di-tert-butyl pyrocarbonate (571 mg, 2.6 mmol) and DMAP (27 mg, 0.2 mmol) in dichloromethane (20 mL) was stirred at room temperature for 12 h. The mixture was evaporated and the residue was purified by silica gel column chromatography (petroleum ether/ethyl acetate=2/1) to give the title compound as a white solid (675 mg, 95%).

Step 5: tetrahydro-2H-pyran-4-yl-7-(2-((tert-butoxycarbonyl)amino)benzo[d]thiazol-6-yl)-2,3-dihydro-1H-pyrido[2,3-b][1,4]oxazine-1-carboxylate (B17)

A mixture of B17-4 (51 mg, 0.16 mmol), B17-3 (61 mg, 0.16 mmol), Pd(PPh$_3$)$_4$ (18 mg, 0.016 mmol), $K_2CO_3$ (75 mg, 0.5 mmol) and $H_2O$ (1 mL) in dioxane (10 mL) was stirred at 80° C. under $N_2$ overnight. The mixture was evaporated and the residue was purified by silica gel column chromatography (dichloromethane/methanol=100/1) to give the title compound as a white solid (55 mg, 50%). $^1$H NMR (400 MHz, CDCl$_3$) δ 10.10 (s, 1H), 8.65 (s, 1H), 8.24 (s, 1H), 8.00 (m, 2H), 7.58 (d, J=7.6 Hz, 1H), 5.06 (s, 1H), 4.46 (s, 2H), 3.97 (d, J=22.6 Hz, 4H), 3.59 (m, 2H), 2.04 (s, 3H), 1.79 (d, J=9.0 Hz, 2H), 1.61 (s, 9H).

Example 3: Compound B14 Made by Method B

Step 1: tetrahydro-2H-pyran-4-yl7-(2-aminobenzo[d]thiazol-6-yl)-2,3-dihydro-1H-pyrido[2,3-b][1,4]oxazine-1-carboxylate hydrochloride (B14)

To a solution of B17 (50 mg, 0.1 mmol) in ethyl acetate (2 mL) was added 3N HCl/EA (5 mL) at room temperature. After stirred at room temperature for 12 h, the mixture was filtered to give the title compound as a white solid (36 mg, 92%). $^1$H NMR (400 MHz, DMSO-d6) δ 9.30 (s, 2H), 8.61 (s, 1H), 8.19 (s, 1H), 8.12 (s, 1H), 7.63 (d, J=7.8 Hz, 1H), 7.55 (d, J=8.3 Hz, 1H), 4.95 (s, 2H), 4.41 (s, 2H), 3.94 (s, 2H), 3.85-3.70 (m, 2H), 3.51 (t, J=8.5 Hz, 2H), 1.96 (d, J=12.2 Hz, 2H), 1.66 (d, J=8.6 Hz, 2H).

Example 4: Compound B33 Made by Method C

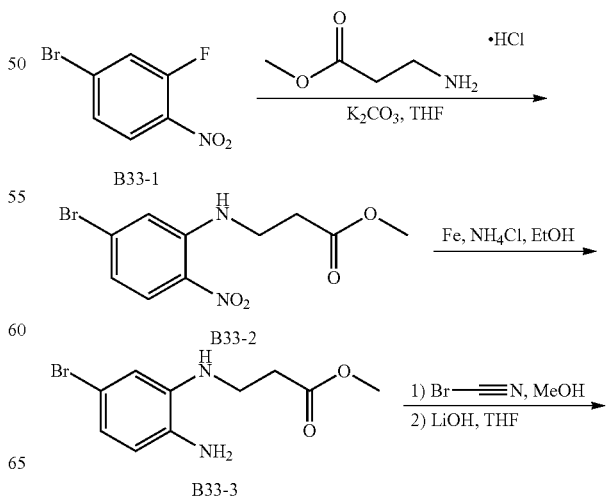

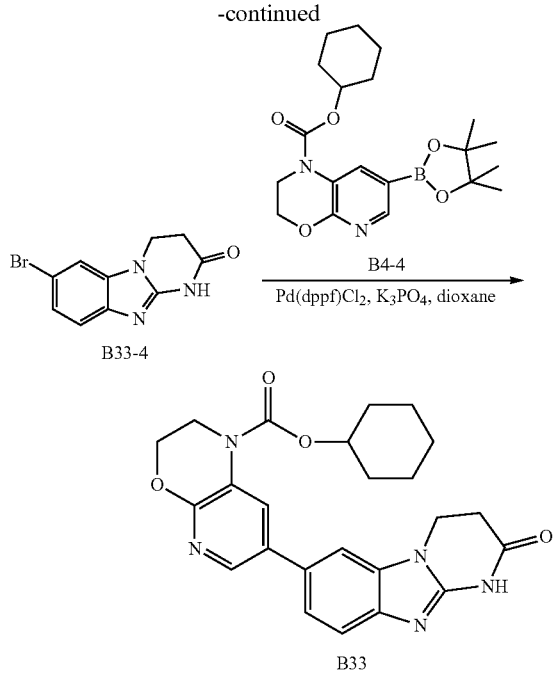

Step 1: methyl 3-((5-bromo-2-nitrophenyl)amino)propanoate (B33-2)

A mixture of 4-bromo-2-fluoro-1-nitrobenzene (2.2 g, 10 mmol), methyl 3-aminopropanoate hydrochloride (1.7 g, 12 mmol) and K$_2$CO$_3$ (4.1 g, 30 mmol) in THF (40 mL) was stirred at 75° C. overnight. After cooling to room temperature, the mixture was treated with brine (50 mL) and extracted with ethyl acetate (40 mL*2). The combined organic layers were dried over Na$_2$SO$_4$, filtered and concentrated to give the title compound as a yellow solid (3.3 g). $^1$H NMR (400 MHz, CDCl$_3$) δ 8.22 (br s, 1H), 8.04 (d, J=8.4 Hz, 1H), 7.04 (s, 1H), 6.79 (d, J=8.4 Hz, 1H), 3.75 (s, 3H), 3.63 (t, J=5.2 Hz, 2H), 2.75 (d, J=6.0 Hz, 2H).

Step 2: methyl 3-((2-amino-5-bromophenyl)amino)propanoate (B33-3)

A mixture of B33-2 (3.3 g, 10.9 mmol), Fe (1.8 g, 32.1 mmol) and saturated aqueous NH$_4$Cl (20 mL) in EtOH (40 mL) was stirred at 60° C. for 2 h. After cooling to room temperature, the mixture was filtered and evaporated to remove most of EtOH. The residue was treated with brine (20 mL) and extracted with ethyl acetate (40 mL*3). The combined organic layers were dried over Na$_2$SO$_4$, filtered and concentrated. The residue was purified by silica gel column chromatography (petroleum ether/ethyl acetate=10/1 to 5/1) to give the title compound as a brown solid (2.9 g, 96%). $^1$H NMR (400 MHz, CDCl$_3$) δ 6.78 (d, J=8.0 Hz, 1H), 6.74 (s, 1H), 6.57 (d, J=8.0 Hz, 1H), 3.71 (s, 3H), 3.40 (t, J=6.2 Hz, 2H), 2.67 (t, J=6.2 Hz, 2H).

Step 3: 7-Bromo-3,4-dihydrobenzo[4,5]imidazo[1,2-a]pyrimidin-2(1H)-one (B33-4)

A mixture of B33-3 (1 g, 3.6 mmol) and cyanogen bromide (582 mg, 5.5 mmol) was stirred at room temperature for 2 h. The mixture was evaporated. The residue was dissolved in THF (20 mL) and MeOH (2 mL). To the solution was added 1N LiOH (11 mL, 11 mmol), the mixture was stirred at room temperature overnight. The resulting suspension was filtered, the filter-cake was dried in vacuo to give the title compound as a white solid (880 mg, 90%). $^1$H NMR (400 MHz, DMSO-d6) δ 7.23 (s, 1H), 7.01 (d, J=8.4 Hz, 1H), 6.96 (d, J=8.4 Hz, 1H), 3.96 (t, J=7.2 Hz, 2H), 2.40 (t, J=7.2 Hz, 2H).

Step 4: Cyclohexyl 7-(2-oxo-1,2,3,4-tetrahydrobenzo[4,5]imidazo[1,2-a]pyrimidin-7-yl)-2,3-dihydro-1H-pyrido[2,3-b][1,4]oxazine-1-carboxylate (B33)

A mixture of B33-4 (40 mg, 0.15 mmol), B4-4 (116 mg, 0.3 mmol), K$_3$PO$_4$ (127 mg, 0.6 mmol), Pd(dppf)Cl$_2$ (22 mg, 0.03 mmol) and water (1 mL) in 1,4-dioxane (7 mL) was stirred at 80° C. overnight while nitrogen was purged through the system. After cooling to room temperature, the mixture was filtered and evaporated. The residue was purified by silica gel column chromatography (dichloromethane/methanol=100/1) to give the title compound as a white solid (10 mg, 15%). $^1$H NMR (400 MHz, DMSO-d$_6$) δ 11.49 (s, 1H), 8.59 (s, 1H), 8.22 (s, 1H), 7.67 (s, 1H), 7.48 (d, J=8.0 Hz, 1H), 7.34 (d, J=7.6 Hz, 1H), 4.84-4.73 (m, 1H), 4.39 (s, 2H), 4.35-4.25 (m, 2H), 3.91 (s, 2H), 2.97-2.86 (m, 2H), 1.95-1.80 (m, 2H), 1.73-1.60 (m, 2H), 1.60-1.27 (m, 6H).

Example 5: Compound B37 Made by Method D

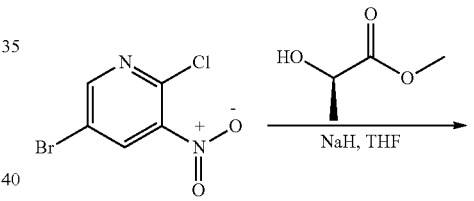

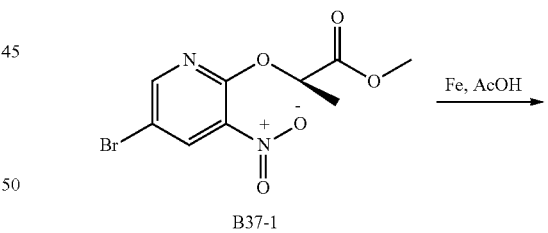

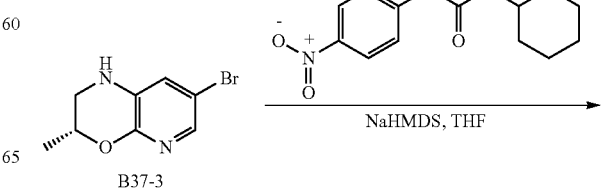

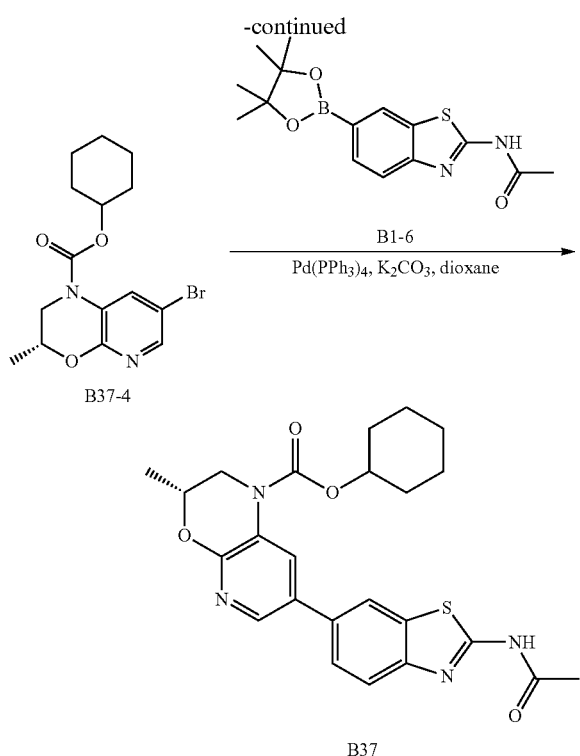

Step 1: methyl (R)-2-((5-bromo-3-nitropyridin-2-yl)oxy)propanoate (B37-1)

To a solution of 5-bromo-2-chloro-3-nitropyridine (1.2 g, 5 mmol) and methyl (R)-2-hydroxypropanoate (572 mg, 5.5 mmol) in THF (40 mL) was added slowly 60% NaH (220 mg, 5.5 mmol) at 0° C. The mixture was stirred at room temperature for 1 h. After water (20 mL) was added, the mixture was treated with brine (100 mL) and extracted with ethyl acetate (50 mL*2). The combined organic layers were dried over $Na_2SO_4$, filtered and concentrated. The residue was purified by silica gel column chromatography (petroleum ether/ethyl acetate=100/1) to give the title compound as a yellow oil (1.2 g 80%). $^1$H NMR (400 MHz, DMSO-$d_6$) δ 8.75 (s, 1H), 8.62 (s, 1H), 5.50-5.34 (m, 1H), 3.67 (s, 3H), 1.56 (d, J=6.4 Hz, 3H).

Step 2: (R)-7-bromo-3-methyl-H-pyrido[2,3-b][1,4]oxazin-2(3H)-one (B37-2)

To a solution of B37-1 (1.2 g, 4.0 mmol) in acetic acid (25 mL) was added slowly Fe (1.1 g, 20 mmol) at 70° C. The mixture was stirred at 70° C. for 3 h. After cooling to room temperature, the mixture was filtered and evaporated to remove most of acetic acid. The residue was poured into 1N HCl (20 mL). The resulting suspension was filtered, the filter-cake was dried to give the title compound as a white solid (800 mg, 82%). $^1$H NMR (400 MHz, DMSO-$d_6$) δ 10.92 (s, 1H), 7.90 (s, 1H), 7.35 (s, 1H), 5.02-4.87 (m, 1H), 1.47 (d, J=6.8 Hz, 3H).

Step 3: (R)-7-bromo-3-methyl-2,3-dihydro-1H-pyrido[2,3-b][1,4]oxazine (B37-3)

To a solution of a B37-2 (800 mg, 3.3 mmol) in of $BH_3$.THF (16 mL, 16 mmol) was stirred at 80° C. for 3 h. After cooling to room temperature, the solvent of the mixture was removed and the residue was dissolved in 3N HCl (15 mL). The mixture was stirred continued at 110° C. for 5 h. It was adjusted pH to 8 by 3N NaOH and extracted with ethyl acetate (30 mL*3). The organic layers were dried over $Na_2SO_4$, filtered and concentrated. It was obtained the title compound as a white solid (550 mg, 73%).

Step 4: Cyclohexyl-(R)-7-bromo-3-methyl-2,3-dihydro-1H-pyrido[2,3-b][1,4]oxazine-1-carboxylate (B37-4)

To a solution of B37-3 (253 mg, 1.1 mmol) in THF (20 mL) was slowly added NaHMDS (1 mL, 2 mmol) at 0° C. under $N_2$. After 10 min, a solution of cyclohexyl (4-nitrophenyl) carbonate (324 mg, 1.4 mmol) in THF (5 mL) was added slowly and stirred for 10 min. Then the reaction was added NaHMDS (0.65 mL, 1.3 mmol) and stirred at room temperature for 2 h. It was quenched by saturated aqueous $NH_4Cl$ and extracted with ethyl acetate (30 mL*3). The organic layers were dried over $Na_2SO_4$, filtered and concentrated. The residue was purified by silica gel column chromatography (petroleum ether/ethyl acetate=10/1) to give the title compound as a colorless oil (200 mg, 51%). $^1$H NMR (400 MHz, DMSO-$d_6$) δ 8.44 (s, 1H), 7.99 (d, J=1.6 Hz, 1H), 4.85-4.70 (m, 1H), 4.55-4.40 (m, 1H), 4.17-4.04 (m, 1H), 3.43-3.33 (m, 1H), 1.91-1.77 (m, 2H), 1.73-1.59 (m, 2H), 1.59-1.30 (m, 9H).

Step 5: Cyclohexyl-(R)-7-(2-acetamidobenzo[d]thiazol-6-yl)-3-methyl-2,3-dihydro-1H-pyrido[2,3-b][1,4]oxazine-1-carboxylate (B37)

A mixture of B37-4 (71 mg, 0.2 mmol), B1-6 (64 mg, 0.2 mmol), Pd(PPh$_3$)$_4$ (23 mg, 0.02 mmol), $K_2CO_3$ (69 mg, 0.5 mmol) and $H_2O$ (1 mL) in dioxane (7 mL) was stirred at 80° C. under $N_2$ overnight. The mixture was evaporated and the residue was purified by silica gel column chromatography (dichloromethane/methanol=100/1) to give the title compound as a white solid (15 mg, 16%). $^1$H NMR (400 MHz, DMSO-$d_6$) δ 12.41 (s, 1H), 8.56 (s, 1H), 8.32-8.20 (m, 2H), 7.81 (d, J=8.4 Hz, 1H), 7.65 (d, J=8.0 Hz, 1H), 4.88-4.71 (m, 1H), 4.56-4.45 (m, 1H), 4.14 (d, J=12.0 Hz, 1H), 3.48-3.33 (m, 1H), 2.21 (s, 3H), 1.94-1.78 (m, 2H), 1.76-1.60 (m, 2H), 1.58-1.30 (m, 9H).

Example 6: Compound B38 Made by Method E

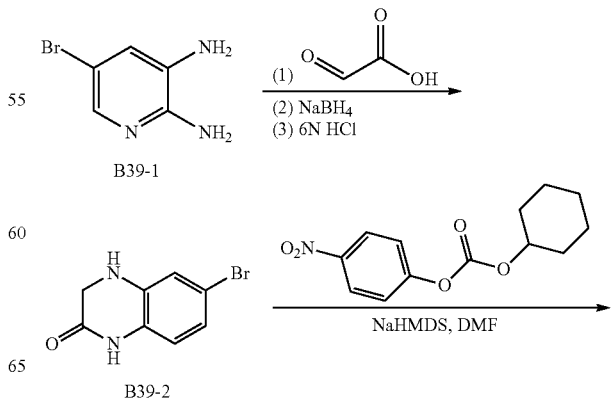

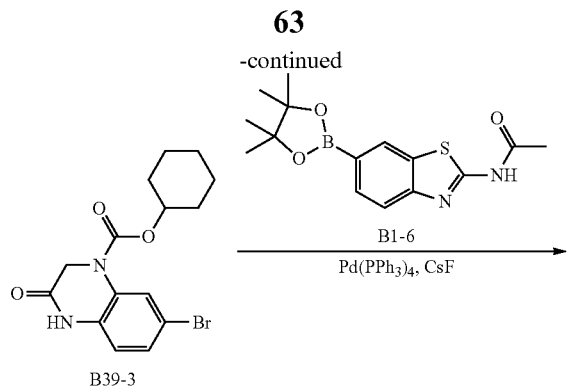

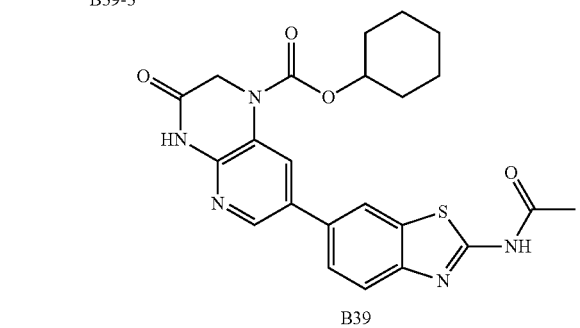

Step 1: 7-Bromo-1,4-dihydropyrido[2,3-b]pyrazin-3(2H)-one (B39-2)

A mixture of 5-bromopyridine-2,3-diamine (2 g, 10.6 mmol) and 50% 2-oxoacetic acid (2 g, 13.8 mmol) in 50 mL of H$_2$O was stirred at room temperature for 48 h. The reaction was filtered and the filter cake was washed by water. The residue was dissolved in 50 mL of methanol and added NaBH$_4$ (1 g, 26.0 mmol) in portions at 0° C. The mixture was stirred at room temperature for 2 h. Then the reaction was added 10 mL of 6N HCl. After stirring at room temperature for an hour, then the reaction was warmed to 50° C. for 2 h. The resulting reaction was evaporated and adjusted pH to 8 by saturated aqueous NaHCO$_3$. Then the mixture was filtered to give a gray solid (2.3 g, 96%). $^1$H NMR (400 MHz, DMSO-d$_6$) δ 7.64 (s, 1H), 7.01-6.98 (m, 2H), 3.93 (s, 2H).

Step 2: Cyclohexyl-7-Bromo-3-oxo-3,4-dihydro-pyrido[2,3-b]pyrazine-1(2H)-carboxylate (B39-3)

In a solution of B39-2 (1.2 g, 5.3 mmol) in 40 mL of DMF was slowly added NaHMDS (2 M, 5 mL) at 0° C. under N$_2$. The mixture was stirred at 0° C. for an hour. A solution of cyclohexyl (4-nitrophenyl) carbonate (1.7 g, 6.4 mmol) in DMF (10 mL) was added slowly and stirred for 10 min. Then the reaction was added NaHMDS (3 mL) and stirred at room temperature overnight. It was quenched by saturated aqueous NH$_4$Cl and extracted with ethyl acetate (20 mL*3). The organic layers were dried over Na$_2$SO$_4$, filtered and concentrated. The residue was purified by silica gel column chromatography (petroleum ether/ethyl acetate=5/1) to give the title compound as a yellow oil (34 mg, 2%). $^1$H NMR (400 MHz, CDCl$_3$) δ 8.26 (s, 1H), 7.30 (s, 1H), 4.79-4.74 (m, 1H), 3.97 (s, 2H), 1.98-1.94 (m, 2H), 1.80-1.76 (m, 2H), 1.61-1.58 (m, 2H), 1.45-1.41 (m, 2H), 1.40-1.36 (m, 2H).

Step 3: Cyclohexyl-7-(2-acetamidobenzo[d]thiazol-6-yl)-3-oxo-3,4-dihydropyrido[2,3-b]pyrazine-1(2H)-carboxylate (39)

A mixture of 39-3 (32 mg, 0.1 mmol), B1-6 (43 mg, 0.1 mmol), CsF (27 mg, 0.2 mmol) and Pd(PPh$_3$)$_4$ (10 mg, 0.01 mmol) in isopropanol/I$_2$O (5 mL/1 mL) was stirred at 95° C. under N$_2$ overnight. The reaction was evaporated and the residue was purified by silica gel column chromatography (dichloromethane/methanol=200/1 to 100/1) to give the title compound as a yellow solid (13 mg, 32%). $^1$H NMR (400 MHz, DMSO-d$_6$) δ 12.43 (s, 1H), 10.88 (s, 1H), 8.43 (s, 1H), 8.31 (s, 1H), 7.88-7.76 (m, 1H), 7.70-7.68 (m, 1H), 7.57 (s, 2H), 4.75 (s, 1H), 4.39 (s, 2H), 2.21 (s, 3H), 1.84-1.76 (m, 2H), 1.72-1.62 (m, 2H), 1.56-1.42 (m, 3H), 1.39-1.28 (m, 3H).

Example 7: Compound 40 Made by Method F

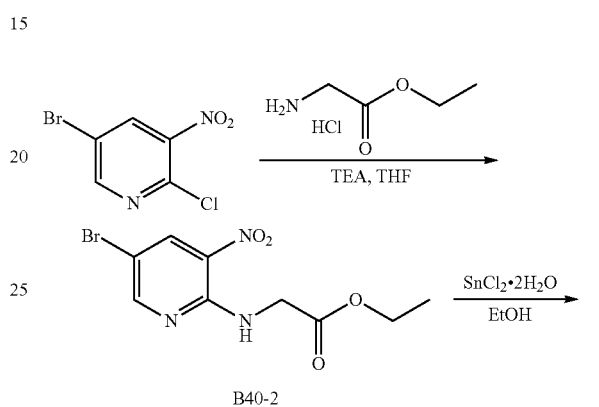

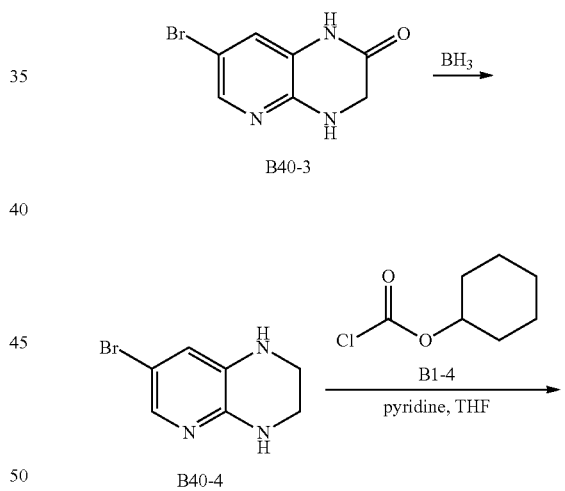

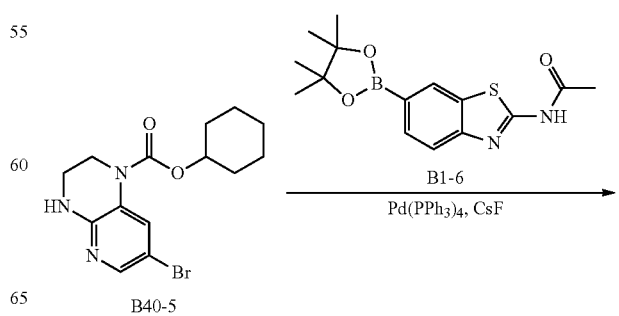

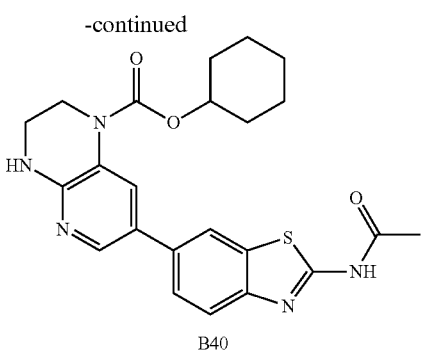

B40

Step 1: ethyl (5-bromo-3-nitropyridin-2-yl)glycinate (B40-2)

In a suspension of 5-bromo-2-chloro-3-nitropyridine (5 g, 21.0 mmol), glycine ethyl ester hydrochloride (8.8 g, 63.0 mmol) in 30 mL of THF was slowly added TEA (10 g, 105.0 mmol) at 0° C. The mixture was stirred at room temperature overnight. It was quenched by saturated aqueous NaCl solution (50 mL) and extracted with ethyl acetate (50 mL*3). The organic layers were dried over $Na_2SO_4$, filtered and concentrated. The residue was purified by silica gel column chromatography (petroleum ether/ethyl acetate=20/1 to 5/1) to give the title compound as a yellow solid (6.7 g, crude). $^1$H NMR (400 MHz, CDCl$_3$) δ 8.57 (s, 1H), 8.54-8.38 (m, 2H), 4.35 (s, 2H), 4.26 (s, 2H), 1.31 (s, 3H).

Step 2: 7-bromo-3,4-dihydropyrido[2,3-b]pyrazin-2(1H)-one (B40-3)

In a solution of B40-2 (3 g, 9.8 mmol) in 10 mL of EtOH was added $SnCl_2·2H_2O$ (9.1 g, 49 mmol) in portions. The mixture was stirred at 80° C. for 2 h. The reaction was filtered and the filter cake was washed by EtOH (10 mL*2). It was obtained the title compound as an orange solid (2.7 g). $^1$H NMR (400 MHz, DMSO-d$_6$) δ 10.49 (s, 1H), 7.65 (s, 1H), 7.03-6.99 (m, 2H), 3.93 (s, 2H).

Step 3: 7-bromo-1,2,3,4-tetrahydropyrido[2,3-b]pyrazine (B40-4)

In a solution of a B40-3 (1.5 g, 6.6 mmol) in 15 mL of BH$_3$.THF was stirred at 80° C. for 1.5 h. The mixture was cooled down and quenched by methanol, then added 3N HCl (2 mL) at 0° C. The mixture was stirred continued at 110° C. for 3 h. It was adjusted pH to 9 by saturated aqueous NaHCO$_3$ and extracted with dichloromethane (10 mL*3). The organic layers were dried over Na$_2$SO$_4$, filtered and concentrated. It was obtained the title compound as a yellow solid (685 mg, 48%). $^1$H NMR (400 MHz, DMSO-d$_6$) δ 7.23 (s, 1H), 6.65 (s, 1H), 6.42 (s, 1H), 5.89 (s, 1H), 3.28 (s, 2H), 3.16 (s, 2H).

Step 4: Cyclohexyl 7-bromo-3,4-dihydropyrido[2,3-b]pyrazine-1(2H)-carboxylate (B40-5)

In a solution of B40-4 (470 mg, 2.2 mmol) and pyridine (521 mg, 6.6 mmol) in 10 mL THF was slowly added B1-4 (356 mg, 2.2 mmol) at 0° C. The mixture was stirred at 0° C. for 2 h. The mixture was added saturated aqueous NaHCO$_3$ (20 mL) and extracted with ethyl acetate (10 mL*3). The organic layers were dried over Na$_2$SO$_4$, filtered and concentrated. The residue was purified by silica gel column chromatography (petroleum ether/ethyl acetate=5/1) to give the title compound as a colorless oil (340 mg, 45%). $^1$H NMR (400 MHz, CDCl$_3$) δ 8.04 (s, 1H), 7.82 (s, 1H), 5.12 (s, 1H), 3.82 (s, 2H), 3.50 (s, 2H), 1.95-1.83 (m, 2H), 1.58-1.51 (m, 3H), 1.48-1.36 (m, 3H), 1.31-1.21 (m, 3H).

Step 5: Cyclohexyl-7-(2-acetamidobenzo[d]thiazol-6-yl)-3,4-dihydropyrido[2,3-b]pyrazine-1(2H)-carboxylate (B40)

A mixture of B40-5 (100 mg, 0.3 mmol), B1-6 (138 mg, 0.4 mmol), CsF (88 mg, 0.6 mmol) and Pd(PPh$_3$)$_4$ (35 mg, 0.03 mmol) in isopropanol/H$_2$O (10 mL/1 mL) was stirred at 95° C. under N$_2$ overnight. The resulting reaction was evaporated and the residue was purified by silica gel column chromatography (dichloromethane/methanol=100/2) to give the title compound as a white solid (69 mg, 53%). $^1$H NMR (400 MHz, DMSO-d$_6$) δ 12.36 (s, 1H), 8.13 (s, 2H), 7.76 (d, J=8.4 Hz, 1H), 7.59 (d, J=8.0 Hz, 1H), 7.10 (s, 1H), 4.74 (s, 1H), 3.73 (s, 2H), 3.42-3.38 (m, 2H), 2.20 (s, 3H), 1.93-1.75 (m, 2H), 1.73-1.60 (m, 2H), 1.55-1.43 (m, 3H), 1.39-1.33 (m, 3H).

Example 8: Compound 43 Made by Methods F and G

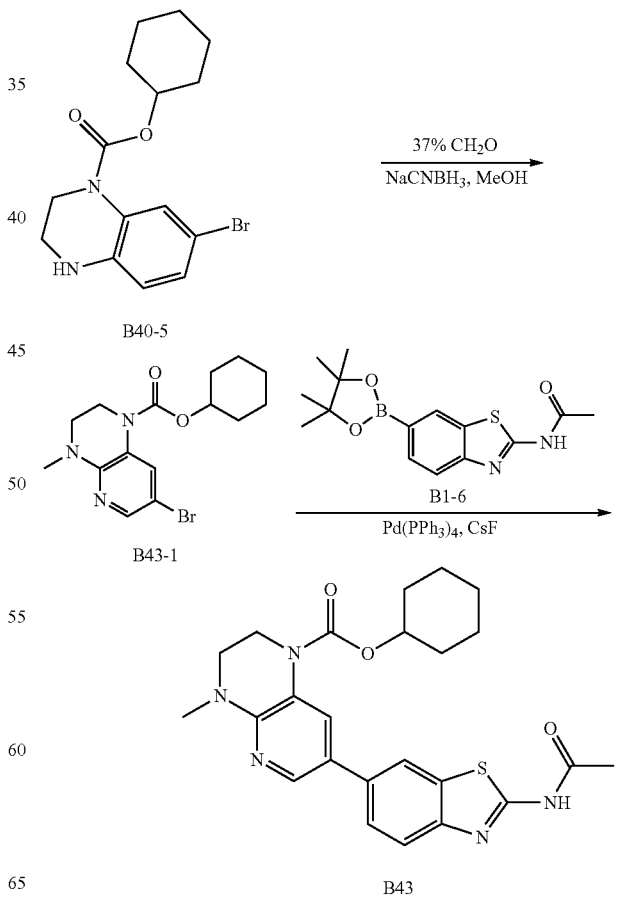

Step 1: cyclohexyl-7-bromo-4-methyl-3,4-dihydro-pyrido[2,3-b]pyrazine-1(2H)-carboxylate (B43-1)

In a solution of B40-5 (140 mg, 0.4 mmol) and 37% CH$_2$O (66 mg, 0.8 mmol) in 3 mL of methanol was stirred at r.t. for 30 min. Then the mixture was added NaBH$_3$CN (52 mg, 0.8 mmol) in portions and stirred overnight. It was quenched by H$_2$O and extracted with dichloromethane (10 mL*3). The organic layers were dried over Na$_2$SO$_4$, filtered and concentrated. The residue was purified by silica gel column chromatography (petroleum ether/ethyl acetate=20/1) to give the title compound as a colorless oil (44 mg, 30%). $^1$H NMR (400 MHz, CDCl$_3$) δ 7.90 (s, 2H), 4.80 (s, 1H), 3.86-3.70 (m, 2H), 3.45-3.40 (m, 2H), 3.12 (s, 3H), 1.95-1.78 (m, 2H), 1.77-1.60 (m, 2H), 1.55-1.45 (m, 2H), 1.42-1.37 (m, 2H), 1.36-1.28 (m, 2H).

Step 2: cyclohexyl7-(2-acetamidobenzo[d]thiazol-6-yl)-4-methyl-3,4-dihydropyrido[2,3-b]pyrazine-1(2H)-carboxylate (B43)

A mixture of B43-1 (34 mg, 0.1 mmol), B1-6 (47 mg, 0.2 mmol), CsF (29 mg, 0.2 mmol) and Pd(PPh$_3$)$_4$ (8.8 mg, 0.01 mmol) in isopropanol/H$_2$O (5 mL/1 mL) was stirred at 95° C. under N$_2$ overnight. The reaction was evaporated and the residue was purified by silica gel column chromatography (dichloromethane/methanol=100/2) to give the title compound as a white solid (7 mg, 15%). $^1$H NMR (400 MHz, DMSO-d$_6$) δ 12.35 (s, 1H), 8.22 (s, 1H), 8.14-8.08 (m, 2H), 7.77-7.75 (m, 1H), 7.61-7.59 (m, 1H), 4.74 (s, 1H), 3.83 (s, 2H), 3.46 (s, 2H), 3.12 (s, 3H), 2.21 (s, 3H), 1.92-1.78 (m, 2H), 1.74-1.58 (m, 2H), 1.57-1.43 (m, 3H), 1.40-1.28 (m, 3H).

Example 9: Compound B48 Made by Method H

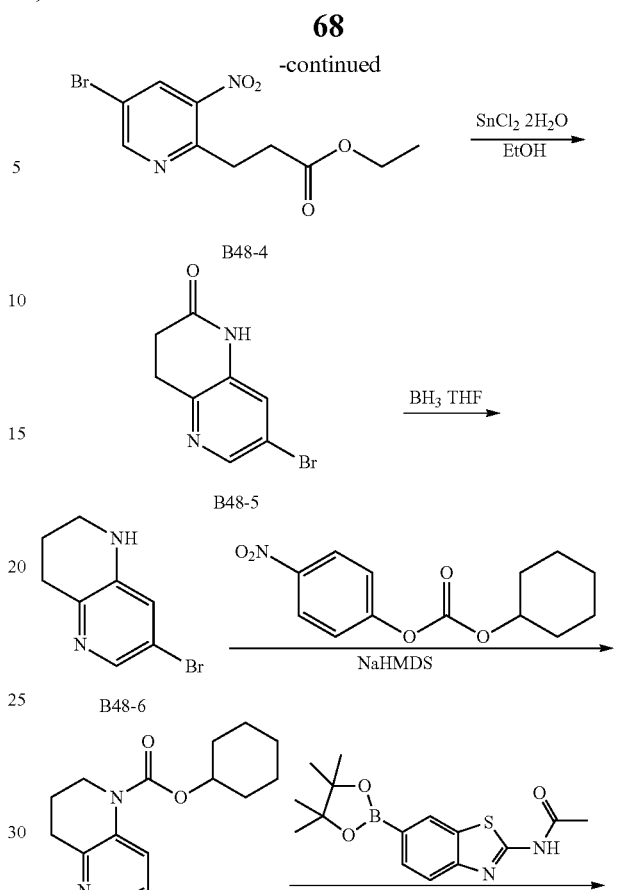

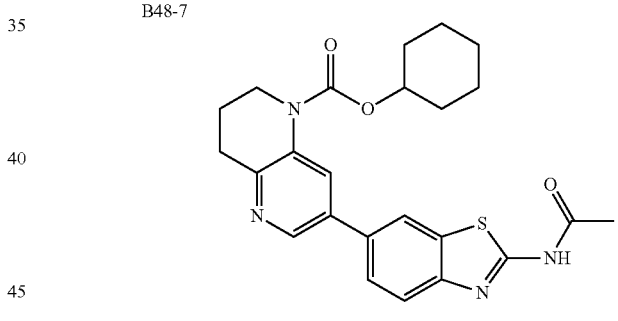

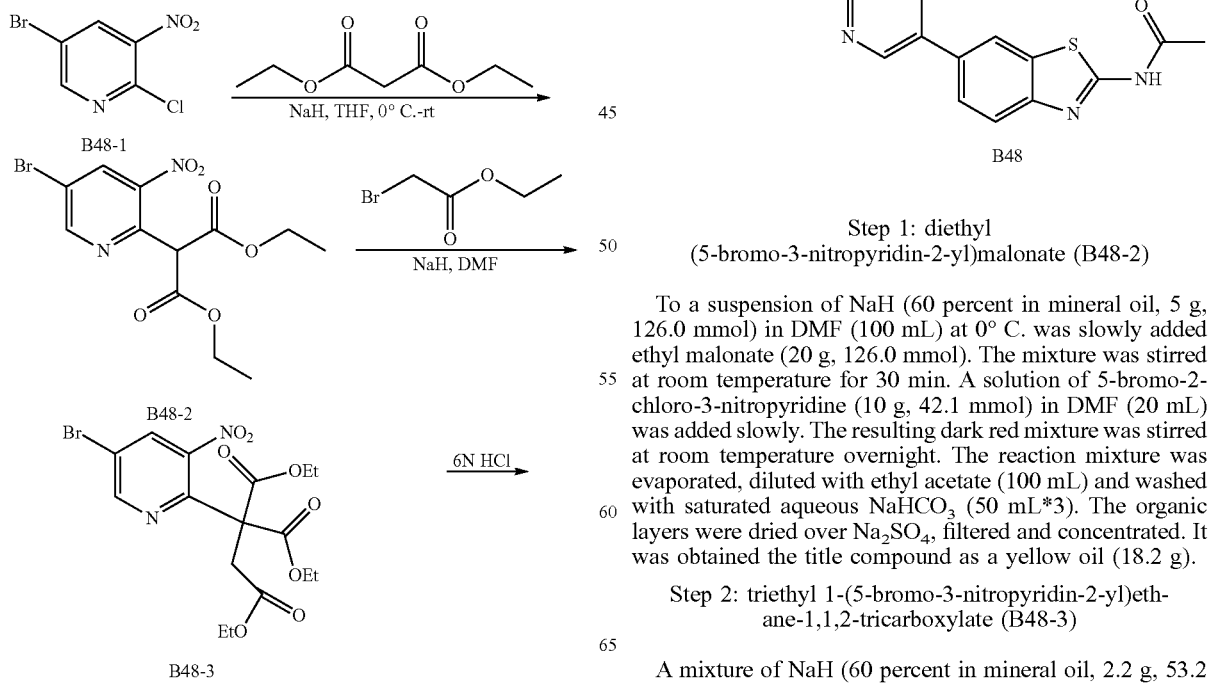

Step 1: diethyl (5-bromo-3-nitropyridin-2-yl)malonate (B48-2)

To a suspension of NaH (60 percent in mineral oil, 5 g, 126.0 mmol) in DMF (100 mL) at 0° C. was slowly added ethyl malonate (20 g, 126.0 mmol). The mixture was stirred at room temperature for 30 min. A solution of 5-bromo-2-chloro-3-nitropyridine (10 g, 42.1 mmol) in DMF (20 mL) was added slowly. The resulting dark red mixture was stirred at room temperature overnight. The reaction mixture was evaporated, diluted with ethyl acetate (100 mL) and washed with saturated aqueous NaHCO$_3$ (50 mL*3). The organic layers were dried over Na$_2$SO$_4$, filtered and concentrated. It was obtained the title compound as a yellow oil (18.2 g).

Step 2: triethyl 1-(5-bromo-3-nitropyridin-2-yl)ethane-1,1,2-tricarboxylate (B48-3)

A mixture of NaH (60 percent in mineral oil, 2.2 g, 53.2 mmol) in 40 mL of DMF was added dropwise a solution of B48-2 (9.6 g, 26.2 mmol) in 5 mL of DMF at 0° C. The mixture was stirred for 1 h. A solution ethyl 2-bromoacetate (6.6 g, 40.0 mmol) in 10 mL of DMF was added slowly. And the reaction was continued stirred overnight. The resulting reaction was evaporated, added saturated aqueous NaHCO$_3$ (50 mL) and extracted with ethyl acetate (20 mL*3). The organic layers were dried over Na$_2$SO$_4$, filtered and concentrated. The residue was purified by silica gel column chromatography (petroleum ether/ethyl acetate=100/1) to give the title compound as a yellow oil (4.9 g, 41%). $^1$H NMR (400 MHz, CDCl$_3$) δ 8.79-8.74 (m, 1H), 8.57-8.53 (m, 1H), 4.27-4.18 (m, 6H), 3.51 (s, 2H), 1.26-1.21 (m, 9H).

Step 3: ethyl 3-(5-bromo-3-nitropyridin-2-yl)propanoate (B48-4)

A mixture of B48-2 (2.5 g, 5.6 mmol) in 10 mL of 6N HCl was stirred at 80° C. under N$_2$ overnight. Then the reaction was cooled to room temperature, adjusted pH to 9 with saturated aqueous NaHCO$_3$ and extracted with dichloromethane (10 mL*3). The organic layers were dried over Na$_2$SO$_4$, filtered and concentrated. The residue was purified by silica gel column chromatography (petroleum ether/ethyl acetate=100/1) to give the title compound as a yellow oil (420 mg, 25%). $^1$H NMR (400 MHz, CDCl$_3$) δ 8.81 (s, 1H), 8.43 (s, 1H), 4.23 (q, J=7.0 Hz, 2H), 3.44 (t, J=6.6 Hz, 2H), 2.93 (t, J=6.6 Hz, 2H), 1.27-1.25 (m, 3H).

Step 4: 7-bromo-3,4-dihydro-1,5-naphthyridin-2(1H)-one (B48-5)

In a solution of B48-3 (420 mg, 1.4 mmol) in 10 mL of EtOH was added SnCl$_2$.2H$_2$O (1.3 g, 7.0 mmol) in portions. The mixture was stirred at 80° C. overnight. The mixture was filtered to give the title compound as a white solid (200 mg, 63%). $^1$H NMR (400 MHz, CDCl$_3$) δ 8.81 (s, 1H), 8.43 (s, 1H), 3.45 (t, J=6.6 Hz, 2H), 2.94 (t, J=6.4 Hz, 2H).

Step 5: 7-bromo-1,2,3,4-tetrahydro-1,5-naphthyridine (B48-6)

B48-4 (200 mg, 0.9 mmol) was added to 5 mL of BH$_3$.THF, the mixture solution was stirred at 80° C. for 2 h. The mixture solution was cooled down and quenched by MeOH at 0° C., then 3N HCl (5 mL) was added. The mixture was continued stirred at 110° C. for 3 h. The reaction was adjusted pH to 9 by saturated aqueous NaHCO$_3$ and extracted with dichloromethane (20 mL). It was obtained the title compound as a colorless oil (100 mg).

Step 6: cyclohexyl-7-bromo-3,4-dihydro-1,5-naphthyridine-1(2H)-carboxylate (B48-7)

To a solution of B48-6 (40 mg, 0.19 mmol) in THF (10 mL) was slowly added NaHMDS (0.12 mL, 0.24 mmol) at 0° C. under N$_2$. After 10 min, a solution of cyclohexyl (4-nitrophenyl) carbonate (61 mg, 0.23 mmol) in THF (2 mL) was added slowly and stirred for 10 min. Then the reaction was added NaHMDS (0.12 mL, 0.24 mmol) and stirred at room temperature for 2 h. It was quenched by saturated aqueous NH$_4$Cl (20 mL) and extracted with ethyl acetate (20 mL*3). The organic layers were dried over Na$_2$SO$_4$, filtered and concentrated. The residue was purified by silica gel column chromatography (petroleum ether/ethyl acetate=50/1) to give the title compound as a colorless oil (45 mg, 70%). $^1$H NMR (400 MHz, DMSO-d$_6$) δ 8.42 (br s, 1H), 8.25 (s, 1H), 4.91-4.76 (m, 1H), 3.78 (t, J=5.6 Hz, 2H), 2.92 (t, J=6.8 Hz, 2H), 2.08-1.95 (m, 2H), 1.94-1.86 (m, 2H), 1.78-1.66 (m, 2H), 1.58-1.38 (m, 6H).

Step 7: cyclohexyl-7-(2-acetamidobenzo[d]thiazol-6-yl)-3,4-dihydro-1,5-naphthyridine-1(2H)-carboxylate (B48)

A mixture of B48-7 (45 mg, 0.13 mmol), B1-6 (51 mg, 0.16 mmol), Pd(PPh$_3$)$_4$ (15 mg, 0.013 mmol), K$_2$CO$_3$ (45 mg, 0.33 mmol) and H$_2$O (1 mL) in dioxane (7 mL) was stirred at 80° C. under N$_2$ overnight. The mixture was evaporated and the residue was purified by silica gel column chromatography (dichloromethane/methanol=80/1) to give the title compound as a white solid (19 mg, 32%). $^1$H NMR (400 MHz, DMSO-d$_6$) δ 12.43 (s, 1H), 8.54 (s, 1H), 8.40 (s, 1H), 8.28 (s, 1H), 7.82 (d, J=8.4 Hz, 1H), 7.69 (d, J=8.4 Hz, 1H), 4.82-4.70 (m, 1H), 3.77 (t, J=5.6 Hz, 2H), 2.92 (t, J=6.0 Hz, 2H), 2.21 (s, 3H), 2.02-1.92 (m, 2H), 1.90-1.79 (m, 2H), 1.71-1.58 (m, 2H), 1.58-1.28 (m, 6H).

Example 10: Compound B50 Made by Methods H and I

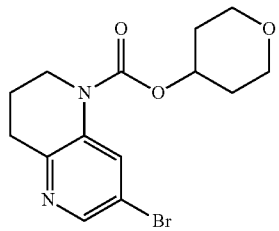

B49-1

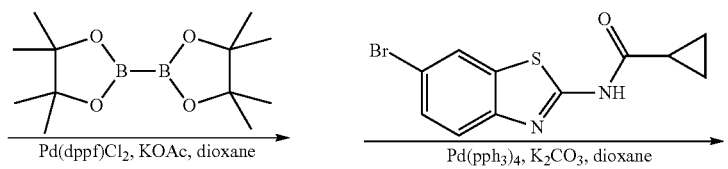

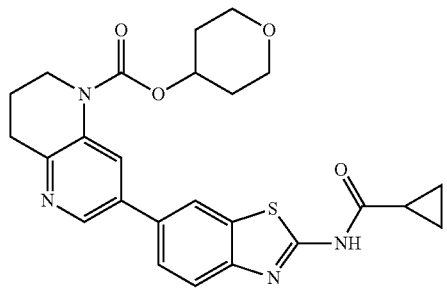

B50

Step 1: tetrahydro-2H-pyran-4-yl-7-(2-(cyclopropanecarboxamido)benzo[d]thiazol-6-yl)-3,4-dihydro-1,5-naphthyridine-1(2H)-carboxylate (B50)

In a suspension of B49-1 (50 mg, 0.2 mmol), 4,4,4',4',5,5,5',5'-octamethyl-2,2'-bi(1,3,2-dioxaborolane) (59 mg, 0.2 mmol), Pd(dppf)Cl$_2$ (11 mg, 0.01 mmol) and KOAc (37 mg, 0.4 mmol) in 5 mL of dioxane was stirred at 100° C. under N$_2$ for 5 h. The reaction was filtered. And the filtrate was added A61-2 (32 mg, 0.1 mmol), Pd(PPh$_3$)$_4$ (13 mg, 0.01 mmol), K$_2$CO$_3$ (38 mg, 0.3 mmol) and H$_2$O (2 mL). The mixture was stirred at 85° C. overnight. The mixture was evaporated and the residue was purified by silica gel column chromatography (dichloromethane/methanol=100/1) to give the title compound as a white solid (20 mg, 38%). $^1$H NMR (400 MHz, DMSO-d$_6$) δ 12.84 (s, 1H), 8.96-8.78 (m, 2H), 8.18 (d, J=8.4 Hz, 1H), 8.08 (d, J=8.4 Hz, 1H), 4.98 (s, 1H), 3.88-3.74 (m, 4H), 3.57-3.47 (m, 2H), 2.99-2.90 (m, 2H), 2.08-1.86 (m, 5H), 1.73-1.59 (m, 2H), 1.03-0.93 (m, 4H).

Example 11: Compound B53 Made by Methods H and J

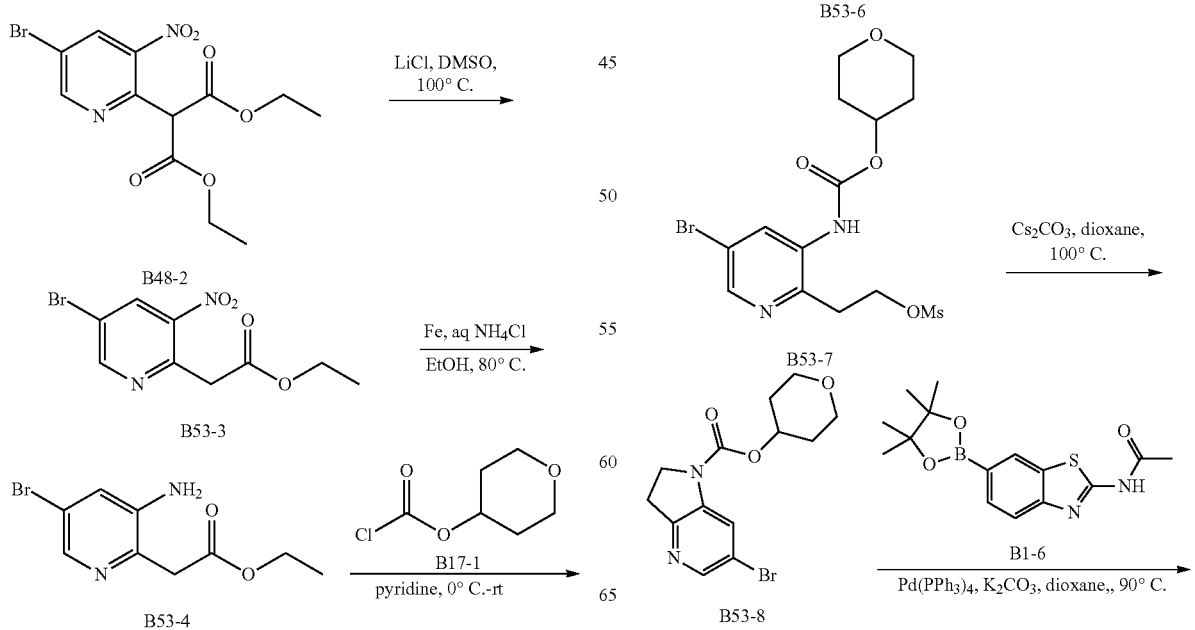

-continued

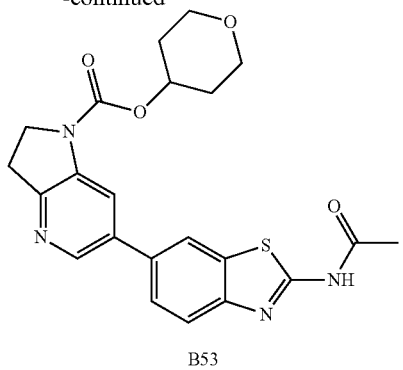

B53

Step 1: ethyl 2-(5-bromo-3-nitropyridin-2-yl)acetate (B53-3)

To a solution of B48-2 (8.6 g, 23.8 mmol) and H$_2$O (43 mg, 2.3 mmol) in 20 mL of DMSO was added LiCl (2.5 g, 23.8 mmol). The mixture was stirred at 100° C. under N$_2$ overnight. The mixture was added ethyl acetate (50 mL) and washed with saturated aqueous NaHCO$_3$ (50 mL*3). The organic layers were dried over Na$_2$SO$_4$, filtered and concentrated. The residue was purified by silica gel column chromatography (petroleum ether/ethyl acetate=100/1) to give the title compound as a yellow oil (4.1 g, 67%). $^1$H NMR (400 MHz, CDCl$_3$) δ 8.85 (s, 1H), 8.57 (s, 1H), 4.28 (s, 2H), 4.22-4.15 (m, 2H), 1.29-1.22 (m, 3H).

Step 2: ethyl 2-(3-amino-5-bromopyridin-2-yl)acetate (B53-4)

In a suspension of B53-3 (4.1 g, 14.2 mmol) and saturated aqueous NH$_4$Cl (20 mL) in 20 mL of EtOH was slowly added Fe (2.4 g, 42.5 mmol) at room temperature. The mixture was stirred at 80° C. for 3 h. The reaction was filtered and extracted with DCM (10 mL*3). The organic layers were dried over Na$_2$SO$_4$, filtered and concentrated. The residue was purified by silica gel column chromatography (petroleum ether/ethyl acetate=5/1) to give the title compound as a yellow oil (550 mg, 71%). $^1$H NMR (400 MHz, CDCl$_3$) δ 8.02 (s, 1H), 7.15 (s, 1H), 4.30-4.05 (m, 4H), 3.77 (s, 2H), 1.26 (t, J=7.0 Hz, 3H).

Step 3: ethyl2-(5-bromo-3-((((tetrahydro-2H-pyran-4-yl)oxy)carbonyl)amino)pyridin-2-yl)acetate (B53-5)

In a solution of B53-4 (500 mg, 1.9 mmol) in 10 mL of pyridine was added B17-1 (467 mg, 2.8 mmol) at 0° C. The mixture was stirred at room temperature overnight. The resulting reaction was evaporated and the residue was purified by silica gel column chromatography (petroleum ether/ethyl acetate=5/1) to give the title compound as a yellow solid (1.9 g, 53%). $^1$H NMR (400 MHz, CDCl$_3$) δ 8.43 (s, 1H), 8.37-8.20 (m, 2H), 4.96 (s, 1H), 4.21 (q, J=6.8 Hz, 2H), 4.00-3.92 (m, 2H), 3.87 (s, 2H), 3.56 (t, J=10.0 Hz, 2H), 2.08-1.90 (m, 2H), 1.85-1.70 (m, 2H), 1.30 (t, J=7.0 Hz, 3H).

Step 4: tetrahydro-2H-pyran-4-yl(5-bromo-2-(2-hydroxyethyl)pyridin-3-yl)carbamate (B53-6)

In a solution of B53-5 (550 mg, 1.4 mmol) in 10 mL of EtOH was added NaBH$_4$ (81 mg, 2.1 mmol) at 0° C. The mixture was stirred at room temperature overnight. The reaction was evaporated and the residue was purified by silica gel column chromatography (petroleum ether/ethyl acetate=1/1) to give the title compound as a yellow oil (440 mg, 83%). $^1$H NMR (400 MHz, CDCl$_3$) δ 8.40 (s, 1H), 8.31 (s, 1H), 5.02-4.87 (m, 1H), 4.08 (s, 2H), 3.99-3.91 (m, 2H), 3.61-3.49 (m, 2H), 2.97 (t, J=5.0 Hz, 2H), 2.08-1.94 (m, 2H), 1.80-1.68 (m, 2H).

Step 5: tetrahydro-2H-pyran-4-yl6-bromo-2,3-dihydro-1H-pyrrolo[3,2-b]pyridine-1-carboxylate (B53-8)

In a solution of B53-6 (200 mg, 0.5 mmol) and TEA (117 mg, 1.1 mmol) in 4 mL of dichloromethane was added MsCl (80 mg, 0.7 mmol) at 0° C. The mixture was stirred at room temperature for 2 h. The reaction was evaporated and the residue was resolved in 4 mL of dioxane. The solution was added Cs$_2$CO$_3$ (284 mg, 0.8 mmol) and stirred at 120° C. overnight. The resulting reaction was added the saturated aqueous NaHCO$_3$ (10 mL) and extracted with ethyl acetate (10 mL*3). The organic layers were combined and dried over Na$_2$SO$_4$, filtered and concentrated. The residue was purified by silica gel column chromatography (petroleum ether/ethyl acetate=10/1) to give the title compound as a colorless oil (65 mg, 34%). $^1$H NMR (400 MHz, CDCl$_3$) δ 8.15 (s, 2H), 5.15-4.90 (m, 1H), 4.10-4.06 (m, 2H), 3.96-3.89 (m, 2H), 3.59 (t, J=9.2 Hz, 2H), 3.19 (t, J=8.4 Hz, 2H), 2.03-1.92 (m, 2H), 1.78-1.68 (m, 2H).

Step 6: tetrahydro-2H-pyran-4-yl6-(2-acetamidobenzo[d]thiazol-6-yl)-2,3-dihydro-1H-pyrrolo[3,2-b]pyridine-1-carboxylate (B53)

In a suspension of B53-8 (50 mg, 0.15 mmol), B1-6 (71 mg, 0.22 mmol), Pd(PPh$_3$)$_4$ (17 mg, 0.015 mmol) K$_2$CO$_3$ (41 mg, 0.3 mmol) and H$_2$O (1 mL) in 5 mL of dioxane was stirred at 90° C. under N$_2$ overnight. The mixture was evaporated and the residue was purified by silica gel column chromatography (dichloromethane/methanol=100/1) to give the title compound as a yellow solid (36 mg, 55%). $^1$H NMR (400 MHz, DMSO-d$_6$) δ 12.42 (s, 1H), 8.42 (s, 1H), 8.28 (s, 1H), 8.19 (s, 1H), 7.83 (d, J=8.4 Hz, 1H), 7.68 (d, J=8.0 Hz, 1H), 4.96 (s, 1H), 4.18-4.00 (m, 2H), 3.88-3.78 (m, 2H), 3.60-3.50 (m, 2H), 3.27-3.18 (m, 2H), 2.22 (s, 3H), 2.02-1.88 (m, 2H), 1.74-1.56 (m, 2H).

Example 12: Compound B59 Made by Methods H and J

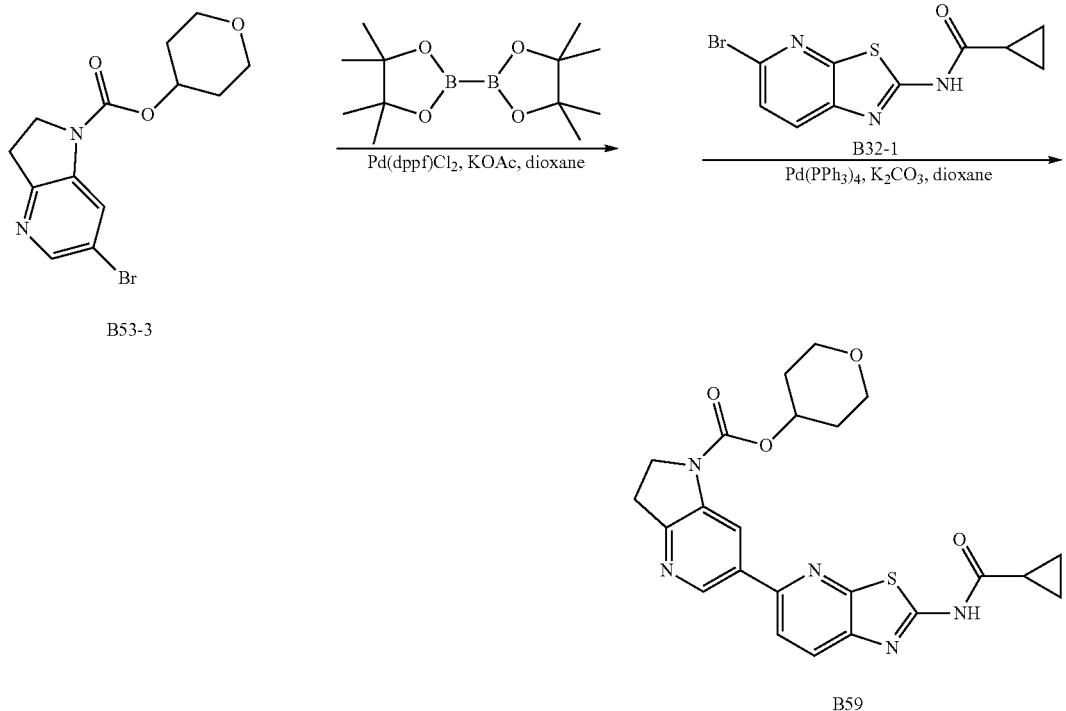

Step 1: tetrahydro-2H-pyran-4-yl6-(2-(cyclopropanecarboxamido)thiazolo[5,4-b]pyridin-5-yl)-2,3-dihydro-1H-pyrrolo[3,2-b]pyridine-1-carboxylate (B59)

In a suspension of B53-8 (90 mg, 0.3 mmol), 4,4,4',4',5,5,5',5'-octamethyl-2,2'-bi(1,3,2-dioxaborolane) (101 mg, 0.4 mmol), Pd(dppf)Cl$_2$ (19 mg, 0.03 mmol) and KOAc (65 mg, 0.7 mmol) in 5 mL of dioxane was stirred at 100° C. under N$_2$ overnight. The reaction was filtered. And the filtrate was added B32-1 (57 mg, 0.2 mmol), Pd(PPh$_3$)$_4$ (23 mg, 0.02 mmol), K$_2$CO$_3$ (66 mg, 0.5 mmol) and H$_2$O (2 mL). The mixture was stirred at 90° C. under N$_2$ for 4 h. The mixture was filtered and the filtrate was evaporated. The residue was purified by silica gel column chromatography (dichloromethane/methanol=100/1) to give the title compound as a gray solid (13 mg, 15%). $^1$H NMR (400 MHz, DMSO-d$_6$) δ 12.88 (s, 1H), 8.82 (s, 1H), 8.70-8.58 (m, 1H), 8.18 (d, J=8.4 Hz, 1H), 8.15-8.06 (m, 1H), 5.20-4.90 (m, 1H), 4.18-4.00 (m, 2H), 3.95-3.80 (m, 2H), 3.65-3.60 (m, 2H), 3.31-3.24 (m, 2H), 2.10-1.90 (m, 4H), 1.75 (s, 1H), 0.99 (s, 4H).

Example 13: Compound B62 Made by Methods H, J and K

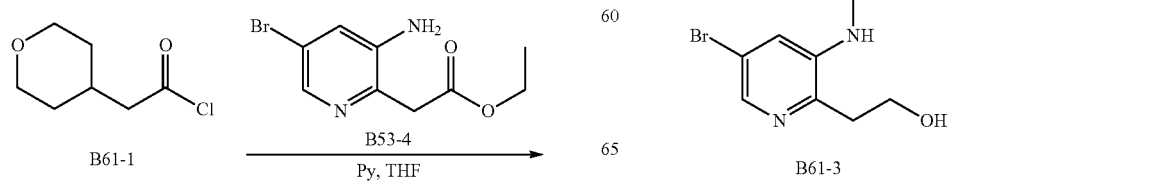

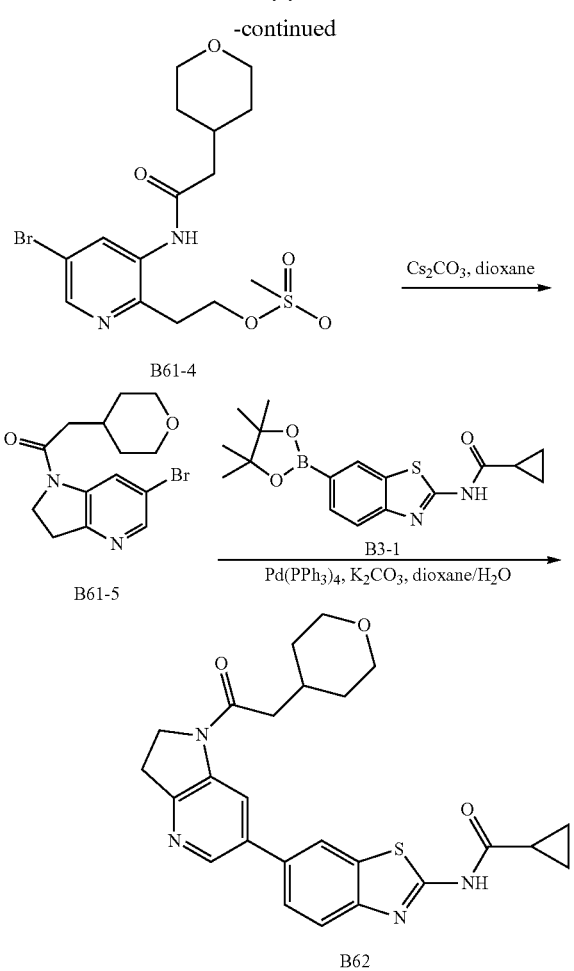

Step 1: Ethyl2-(5-bromo-3-(2-(tetrahydro-2H-pyran-4-yl)acetamido)pyridin-2-yl)acetate (B61-2)

In a solution of B53-4 (1.5 g, 5.8 mmol) and pyridine (1.4 g, 17.4 mmol) in THF (25 mL) was added B61-1 (1.2 g, 7.0 mmol) at 0° C. The mixture was stirred at room temperature for 4 h. The resulting reaction was evaporated and the residue was purified by silica gel column chromatography (petroleum ether/ethyl acetate=2/1) to give the title compound as a yellow oil (1.4 g, 64%). $^1$H NMR (400 MHz, CDCl$_3$) δ 9.21 (br s, 1H), 8.56 (s, 1H), 8.35 (s, 1H), 4.27-4.14 (m, 2H), 4.05-3.91 (m, 2H), 3.86 (s, 2H), 3.49-3.35 (m, 2H), 2.43-2.29 (m, 2H), 2.26-2.10 (m, 1H), 1.77-1.65 (m, 2H), 1.49-1.35 (m, 2H), 1.31 (t, J=7.2 Hz, 3H).

Step 2: N-(5-bromo-2-(2-hydroxyethyl)pyridin-3-yl)-2-(tetrahydro-2H-pyran-4-yl)acetamide (B61-3)

In a solution of B61-2 (1.4 g, 3.6 mmol) in EtOH (10 mL) was added NaBH$_4$ (680 mg, 18 mmol) at 0° C. The mixture was stirred at room temperature overnight. The reaction was evaporated and the residue was purified by silica gel column chromatography (dichloromethane/methanol=30/1) to give the title compound as a yellow oil (1.1 g, 92%). $^1$H NMR (400 MHz, DMSO-d$_6$) δ 9.69 (br s, 1H), 8.40 (s, 1H), 8.20 (s, 1H), 4.95 (br s, 1H), 3.99-3.63 (m, 4H), 3.33-3.25 (m, 2H), 2.98-2.81 (m, 2H), 2.39-2.20 (m, 2H), 2.08-1.87 (m, 1H), 1.77-1.49 (m, 2H), 1.38-1.14 (m, 2H).

Step 3: 2-(5-bromo-3-(2-(tetrahydro-2H-pyran-4-yl)acetamido)pyridin-2-yl)ethyl methanesulfonate (B61-4)

In a solution of B61-3 (1.1 g, 3.5 mmol) and TEA (400 mg, 3.9 mmol) in dichloromethane (30 mL) was added slowly MsCl (440 mg, 3.9 mmol) at 0° C. The mixture was stirred at room temperature for 2 h. The mixture was treated with brine (50 mL) and extracted with ethyl acetate (30 mL*2). The combined organic layers were dried over Na$_2$SO$_4$, filtered and concentrated to give the title compound as a brown solid (1.4 g, 95%).

Step 4: 1-(6-bromo-2,3-dihydro-1H-pyrrolo[3,2-b]pyridin-1-yl)-2-(tetrahydro-2H-pyran-4-yl)ethan-1-one (B61-5)

A mixture of B61-4 (1.4 g, 3.3 mmol) and Cs$_2$CO$_3$ (1.3 g, 4.0 mmol) in dioxane (30 mL) was stirred at 110° C. for 5 h. After cooling to room temperature, the mixture was filtered and evaporated. The residue was purified by silica gel column chromatography (dichloromethane/methanol=70/1) to give the title compound as a white solid (800 mg, 75%). $^1$H NMR (400 MHz, DMSO-d$_6$) δ 8.37 (s, 1H), 8.19 (s, 1H), 4.17 (s, 2H), 3.83 (s, 2H), 3.28-2.99 (m, 4H), 2.49-2.25 (m, 2H), 2.15-1.91 (m, 1H), 1.78-1.42 (m, 2H), 1.40-1.00 (m, 2H).

Step 6: N-(6-(1-(2-(tetrahydro-2H-pyran-4-yl)acetyl)-2,3-dihydro-1H-pyrrolo[3,2-b]pyridin-6-yl)benzo[d]thiazol-2-yl)cyclopropanecarboxamide (B62)

A mixture of B62-5 (65 mg, 0.2 mmol), B3-1 (206 mg, 0.6 mmol), Pd(PPh$_3$)$_4$ (23 mg, 0.02 mmol), K$_2$CO$_3$ (69 mg, 0.5 mmol) and H$_2$O (1 mL) in dioxane (7 mL) was stirred at 80° C. under N$_2$ overnight. After cooling to room temperature, the mixture was evaporated and the residue was purified by silica gel column chromatography (dichloromethane/methanol=50/1) to give the title compound as a white solid (20 mg, 22%). $^1$H NMR (400 MHz, DMSO-d$_6$) δ 12.72 (br s, 1H), 8.58 (s, 1H), 8.45 (s, 1H), 8.27 (s, 1H), 7.81 (d, J=8.4 Hz, 1H), 7.68 (d, J=8.0 Hz, 1H), 4.20 (t, J=8.0 Hz, 2H), 3.89-3.78 (m, 2H), 3.30-3.19 (m, 4H), 2.45 (d, J=6.4 Hz, 2H), 2.15-1.94 (m, 2H), 1.73-1.60 (m, 2H), 1.36-1.19 (m, 2H), 1.02-0.88 (m, 4H).

Example 14: Compound B78 Made by Methods H, J and K

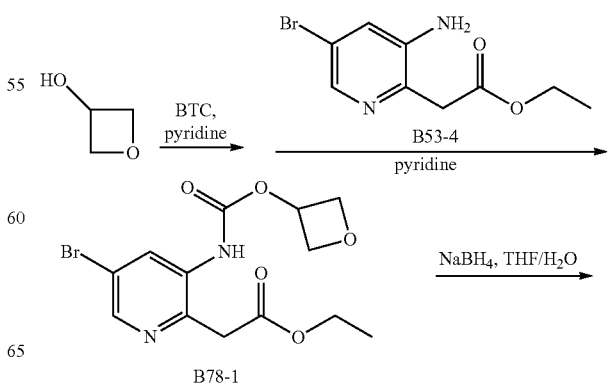

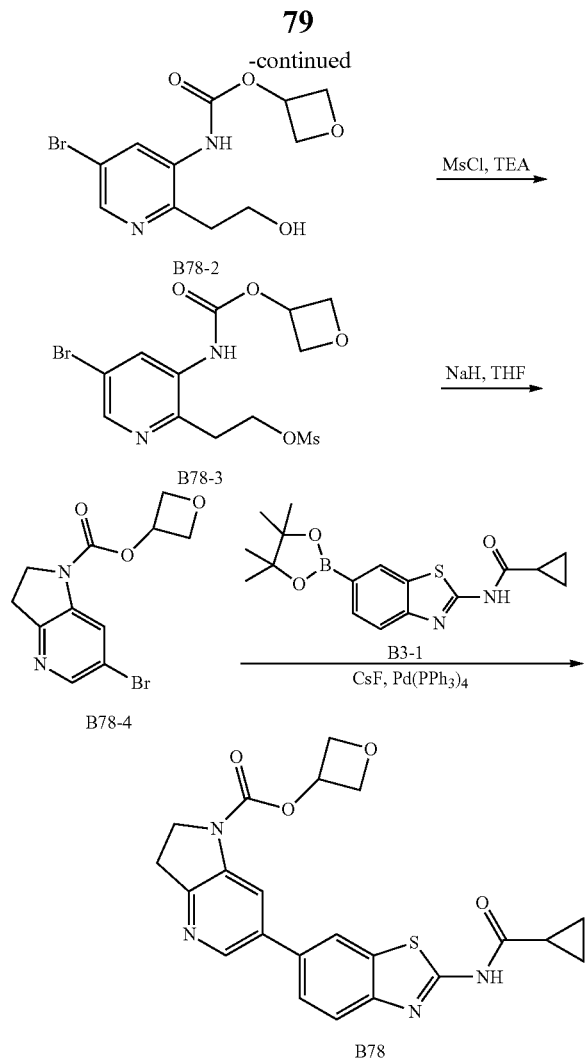

Step 1: Ethyl 2-(5-bromo-3-(((oxetan-3-yloxy)car-bonyl)amino)pyridin-2-yl)acetate (B78-1)

To a solution of bis(trichloromethyl)carbonate (1.6 g, 5.6 mmol) in 30 mL of dichloromethane was added dropwise pyridine (1.2 g, 15.2 mmol) at 0° C. After stirring for 10 min, a solution of oxetan-3-ol (1 g, 14.0 mmol) in 10 mL of dichloromethane was added slowly. The mixture was stirred for 1 h. The resulting solution was filtered. The filtrate was added to a solution of B53-4 (1.2 g, 4.6 mmol) in 50 mL of pyridine. The mixture was stirred at room temperature overnight. The resulting mixture was evaporated, added the saturated aqueous $NaHCO_3$ (50 mL) and extracted with ethyl acetate (50 mL*3). The organic layers were combined and dried over $Na_2SO_4$, filtered and concentrated. The residue was purified by silica gel column chromatography (petroleum ether/ethyl acetate=10/1 to 5/1) to give the title compound as a yellow oil (1.2 g, 75%). $^1$H NMR (400 MHz, $CDCl_3$) δ 8.61 (s, 1H), 8.42-8.27 (m, 2H), 5.57-5.47 (m, 1H), 4.96-4.90 (m, 2H), 4.76-4.70 (m, 2H), 4.22 (q, J=7.2 Hz, 2H), 3.88 (s, 2H), 1.30 (t, J=7.2 Hz, 3H).

Step 2: Oxetan-3-yl (5-bromo-2-(2-hydroxyethyl)pyridin-3-yl)carbamate (B78-2)

To a solution of B78-1 (500 mg, 1.4 mmol) in a mixed solution of THF (20 mL) and $H_2O$ (4 mL) was added $NaBH_4$ (159 mg, 4.2 mmol) at 0° C. in portions. The mixture was stirred at 0° C. for 2 h. The mixture was added the saturated aqueous $NaHCO_3$ (20 mL) and extracted with ethyl acetate (20 mL). The organic layer was dried over $Na_2SO_4$, filtered and concentrated. The residue was purified by silica gel column chromatography (petroleum ether/ethyl acetate=1/1) to give the title compound as a colorless oil (273 mg, 62%). $^1$H NMR (400 MHz, $CDCl_3$) δ 8.42-8.28 (m, 2H), 8.22 (s, 1H), 5.57-5.45 (m, 1H), 4.93 (t, J=7.0 Hz, 2H), 4.76-4.66 (m, 2H), 4.10 (t, J=5.2 Hz, 2H), 3.00 (t, J=5.2 Hz, 2H).

Step 3: 2-(5-Bromo-3-(((oxetan-3-yloxy)carbonyl)amino)pyridin-2-yl)ethyl methanesulfonate (B78-3)

In a solution of B78-2 (273 mg, 0.86 mmol) and TEA (96 mg, 0.95 mmol) in 10 mL of dichloromethane was added MsCl (109 mg, 0.95 mmol) at 0° C. The mixture was stirred at room temperature for 1 h. The mixture was added the saturated aqueous $NaHCO_3$ (10 mL) and extracted with dichloromethane (10 mL). The organic layer was dried over $Na_2SO_4$, filtered and concentrated to give the title compound as a yellow oil (200 mg).

Step 4: Oxetan-3-yl 6-bromo-2,3-dihydro-H-pyrrolo[3,2-b]pyridine-1-carboxylate (B78-4)

To a suspension of NaH (60 percent in mineral oil, 40 mg, 1.0 mmol) in THF (15 mL) at 0° C. was slowly added B78-3 (200 mg, 0.5 mmol). The mixture was stirred at 0° C. for 1.5 h. It was quenched by saturated aqueous $NH_4Cl$ and extracted with ethyl acetate (10 mL). The organic layer was dried over $Na_2SO_4$, filtered and concentrated. The residue was purified by silica gel column chromatography (petroleum ether/ethyl acetate=1/1) to give the title compound as a colorless solid (120 mg, 80%). $^1$H NMR (400 MHz, $CDCl_3$) δ 8.28-8.11 (m, 2H), 5.68-5.45 (m, 1H), 5.05-4.85 (m, 2H), 4.83-4.60 (m, 2H), 4.19-4.05 (m, 2H), 3.33-3.14 (m, 2H).

Step 5: Oxetan-3-yl-6-(2-(cyclopropanecarbox-amido)benzo[d]thiazol-6-yl)-2,3-dihydro-1H-pyrrolo[3,2-b]pyridine-1-carboxylate (B78)

A mixture of B78-4 (60 mg, 0.2 mmol), B1-3 (138 mg, 0.4 mmol), CsF (106 mg, 0.7 mmol) and $Pd(PPh_3)_4$ (23 mg, 0.02 mmol) in isopropanol/$H_2O$ (10 mL/2 mL) was stirred at 95° C. under $N_2$ overnight. The reaction was evaporated and the residue was purified by silica gel column chromatography (dichloromethane/methanol=200/1) to give the title compound as a yellow solid (20 mg, 23%). $^1$H NMR (400 MHz, DMSO-$d_6$) δ 12.72 (s, 1H), 8.50-8.40 (m, 1H), 8.29 (s, 1H), 8.14 (s, 1H), 7.82 (d, J=8.4 Hz, 1H), 7.68 (d, J=8.4 Hz, 1H), 5.49 (s, 1H), 4.85 (t, J=7.0 Hz, 2H), 4.62 (s, 2H), 4.25-4.05 (m, 2H), 3.24 (t, J=8.8 Hz, 4H), 2.06-1.94 (m, 1H), 1.02-0.88 (m, 4H).

Example 15: Compound 60 Made by Methods H, J, K and L

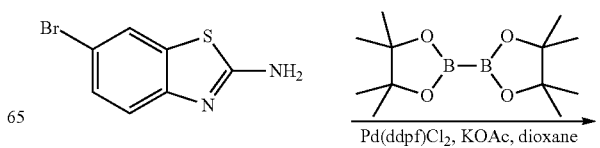

-continued

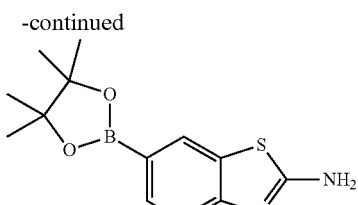

B60-1

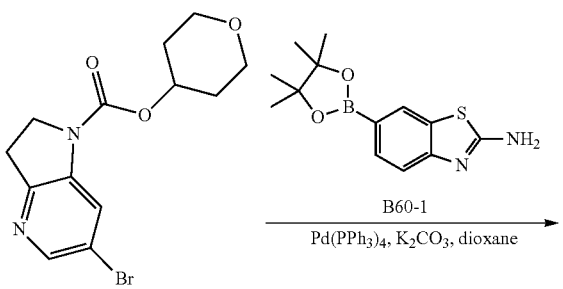

B53-8

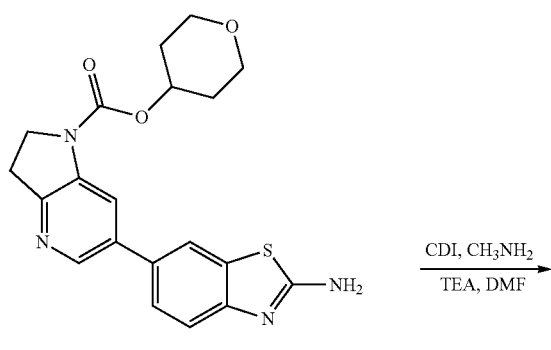

B60-2

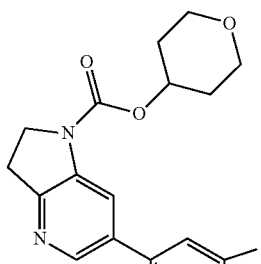

B60

Step 1: 6-(4,4,5,5-Tetramethyl-1,3,2-dioxaborolan-2-yl)benzo[d]thiazol-2-amine (B60-1)

In a suspension of 6-bromobenzo[d]thiazol-2-amine (500 mg, 2.2 mmol), 4,4,4',4',5,5,5',5'-octamethyl-2,2'-bi(1,3,2-dioxaborolane) (1.1 g, 4.4 mmol), Pd(dppf)Cl$_2$ (161 mg, 0.2 mmol) and KOAc (754 mg, 7.7 mmol) in 20 mL of dioxane was stirred at 100° C. under N$_2$ overnight. The reaction was filtered. And the filtrate was evaporated to give the title compound as a black oil (1.5 g).

Step 2: Tetrahydro-2H-pyran-4-yl6-(2-aminobenzo[d]thiazol-6-yl)-2,3-dihydro-1H-pyrrolo[3,2-b]pyridine-1-carboxylate (B60-2)

In a suspension of B53-8 (100 mg, 0.3 mmol), B60-1 (165 mg, 0.6 mmol), Pd(PPh$_3$)$_4$ (35 mg, 0.03 mmol) K$_2$CO$_3$ (145 mg, 1.0 mmol) and H$_2$O (2 mL) in 10 mL of dioxane was stirred at 90° C. overnight. The mixture was evaporated and the residue was purified by silica gel column chromatography (dichloromethane/methanol=100/1) to give the title compound as a yellow solid (86 mg, 73%). $^1$H NMR (400 MHz, DMSO-d$_6$) δ 8.35 (s, 1H), 7.97 (s, 1H), 7.59 (s, 2H), 7.49-7.44 (m, 1H), 7.43-7.38 (m, 1H), 4.44 (s, 1H), 4.12-4.02 (m, 2H), 3.89-3.77 (m, 2H), 3.40-3.37 (m, 2H), 3.23-3.18 (m, 2H), 2.02-1.90 (m, 2H), 1.71-1.60 (m, 2H).

Step 3: Tetrahydro-2H-pyran-4-yl6-(2-(3-methylureido)benzo[d]thiazol-6-yl)-2,3-dihydro-1H-pyrrolo[3,2-b]pyridine-1-carboxylate (B60)

In a solution of B60-2 (70 mg, 0.2 mmol) and CDI (142 mg, 0.9 mmol) in 5 mL of DMF was stirred at room temperature overnight. Then the reaction was added TEA (171 mg, 1.7 mmol) and methylamine hydrochloride (115 mg, 1.7 mmol). The mixture was stirred at room temperature for 3 h. The resulting reaction was evaporated, added the saturated aqueous NaHCO$_3$ (10 mL) and extracted with ethyl acetate (10 mL*3). The organic layers were dried over Na$_2$SO$_4$, filtered and concentrated. The residue was purified by silica gel column chromatography (dichloromethane/methanol=100/1) to give the title compound as a yellow solid (3 mg, 4%). $^1$H NMR (400 MHz, DMSO-d$_6$) δ 10.92 (s, 1H), 8.40 (s, 1H), 8.19 (s, 2H), 7.70 (d, J=8.0 Hz, 1H), 7.60 (d, J=8.0 Hz, 1H), 6.68 (s, 1H), 4.96 (s, 1H), 4.25-3.95 (m, 2H), 3.92-3.75 (m, 2H), 3.60-3.45 (m, 2H), 3.22 (t, J=8.6 Hz, 2H), 2.73 (d, J=4.4 Hz, 3H), 2.05-1.90 (m, 2H), 1.75-1.60 (m, 2H).

Example 16: Compounds 67 and 68 Made by Methods H, J, K and M

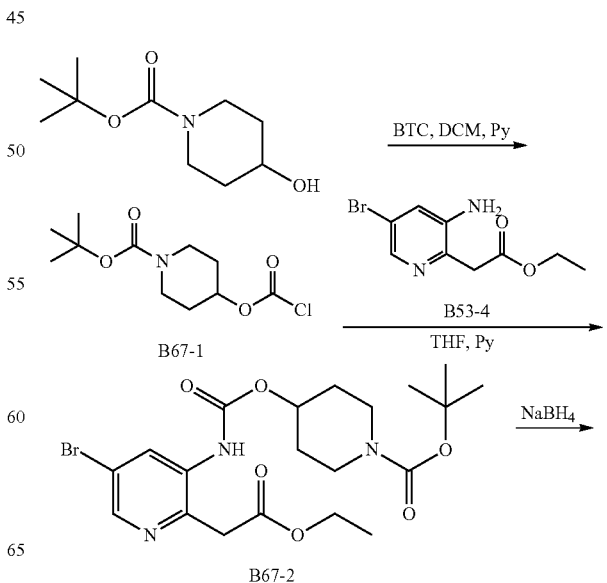

-continued

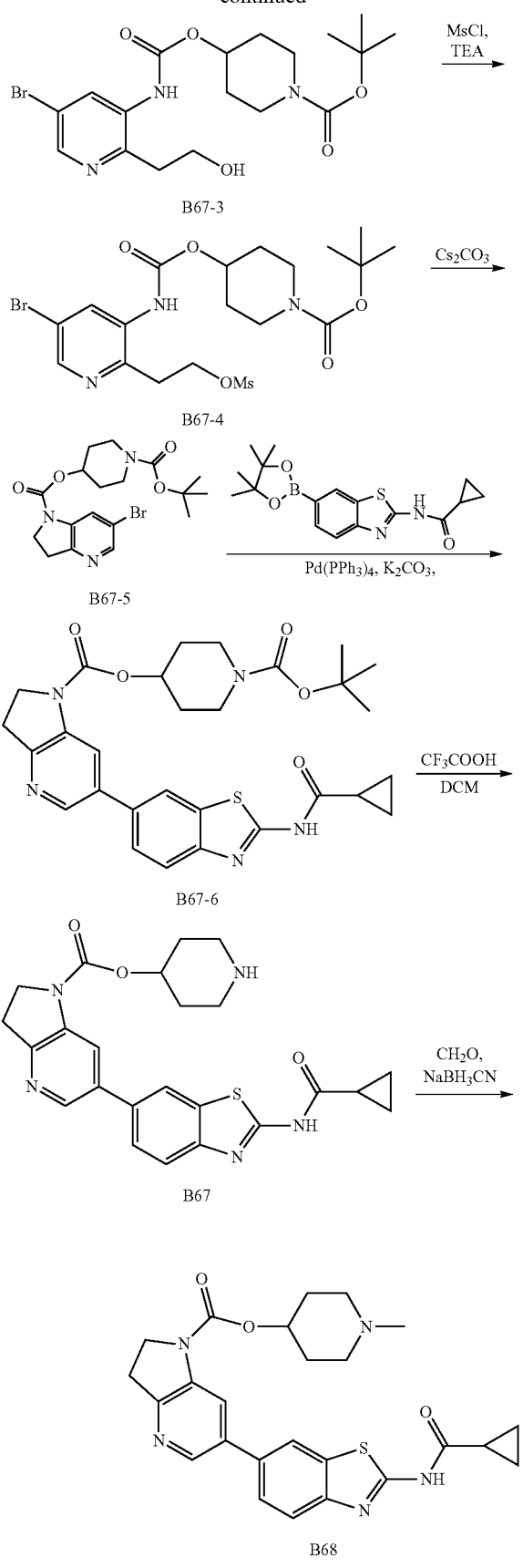

Step 1: Tert-butyl-4-((chlorocarbonyl)oxy)piperidine-1-carboxylate (B67-1)

To a solution of bis(trichloromethyl)carbonate (592 mg, 2 mmol) in 40 mL of dichloromethane was added dropwise pyridine (553 mg, 7 mmol) at 0° C. After stirring for 10 min, a solution of tert-butyl 4-hydroxypiperidine-1-carboxylate (950 mg, 4.7 mmol) in dichloromethane (10 mL) was added slowly. The mixture was stirred for 1 h. The resulting solution was filtered and the filtrate was evaporated to give the crude title compound as a colorless oil (1.1 g, 92%).

Step 2: Tert-butyl-4-(((5-bromo-2-(2-ethoxy-2-oxoethyl)pyridin-3-yl)carbamoyl)oxy)piperidine-1-carboxylate (B67-2)

In a solution of B53-4 (130 mg, 0.5 mmol) and pyridine (160 mg, 2 mmol) in THF (25 mL) was added B67-1 (264 mg, 1 mmol) at 0° C. The mixture was stirred at room temperature for 4 h. The resulting reaction was evaporated and the residue was purified by silica gel column chromatography (petroleum ether/ethyl acetate=2/1) to give the title compound as a yellow oil (120 mg, 50%). $^1$H NMR (400 MHz, CDCl$_3$) δ 8.42 (br s, 1H), 8.36-8.22 (m, 2H), 5.03-4.87 (m, 1H), 4.28-4.11 (m, 2H), 3.87 (s, 2H), 3.81-3.70 (m, 2H), 3.28-3.15 (m, 2H), 2.00-1.90 (m, 2H), 1.76-1.67 (m, 2H), 1.48 (s, 9H). 1.30 (t, J=6.8 Hz, 3H).

Step 3: Tert-butyl-4-(((5-bromo-2-(2-hydroxyethyl)pyridin-3-yl)carbamoyl)oxy)piperidine-1-carboxylate (B67-3)

In a solution of B67-2 (850 mg, 1.8 mmol) in EtOH (30 mL) was added NaBH$_4$ (333 mg, 8.8 mmol) at 0° C. The mixture was stirred at room temperature overnight. The reaction was evaporated and the residue was purified by silica gel column chromatography (dichloromethane/methanol=30/1) to give the title compound as a yellow oil (760 mg, 95%). $^1$H NMR (400 MHz, CDCl$_3$) δ 8.40 (br s, 1H), 8.30 (s, 1H), 7.93 (s, 1H), 4.00-4.85 (m, 1H), 4.17-4.08 (m, 2H), 3.93-3.75 (m, 2H), 3.29-3.17 (m, 2H), 3.04-2.93 (m, 2H), 2.00-1.85 (m, 2H), 1.75-1.65 (m, 2H), 1.46 (s, 9H).

Step 4: Tert-butyl-4-(((5-bromo-2-(2-((methylsulfonyl)oxy)ethyl)pyridin-3-yl)carbamoyl)oxy)piperidine-1-carboxylate (B67-4)

In a solution of B67-3 (753 mg, 1.7 mmol) and TEA (189 mg, 1.9 mmol) in dichloromethane (20 mL) was added slowly MsCl (213 mg, 1.9 mmol) at 0° C. The mixture was stirred at room temperature for 2 h. The mixture was treated with brine (50 mL) and extracted with ethyl acetate (30 mL*2). The combined organic layers were dried over Na$_2$SO$_4$, filtered and concentrated to give the title compound as a brown solid (890 mg).

Step 5: 1-(tert-butoxycarbonyl)piperidin-4-yl-6-bromo-2,3-dihydro-1H-pyrrolo[3,2-b]pyridine-1-carboxylate (B67-5)

A mixture of B67-4 (886 mg, 1.7 mmol) and Cs$_2$CO$_3$ (665 mg, 2.0 mmol) in dioxane (30 mL) was stirred at 110° C. for 5 h. After cooling to room temperature, the mixture was filtered and evaporated. The residue was purified by silica gel column chromatography (petroleum ether/ethyl acetate=5/1) to give the title compound as a white solid (400 mg, 55%). $^1$H NMR (400 MHz, CDCl$_3$) δ 8.30-8.08 (m, 2H), 5.11-4.93 (m, 1H), 4.14-4.04 (m, 2H), 3.75-3.65 (m, 2H), 3.38-3.26 (m, 2H), 3.22-3.14 (m, 2H), 2.00-1.85 (m, 2H), 1.82-1.65 (m, 2H). 1.46 (s, 9H).

Step 6: 1-(tert-butoxycarbonyl)piperidin-4-yl-6-(2-(cyclopropanecarboxamido)benzo[d]thiazol-6-yl)-2,3-dihydro-1H-pyrrolo[3,2-b]pyridine-1-carboxylate (B67-6)

A mixture of B67-5 (106 mg, 0.25 mmol), B3-1 (172 mg, 0.5 mmol), Pd(PPh₃)₄ (29 mg, 0.025 mmol), K₂CO₃ (87 mg, 0.63 mmol) and H₂O (1 mL) in dioxane (7 mL) was stirred at 80° C. under N₂ overnight. After cooling to room temperature, the mixture was evaporated and the residue was purified by silica gel column chromatography (dichloromethane/methanol=50/1) to give the title compound as a white solid (100 mg, 71%).

Step 7: Piperidin-4-yl-6-(2-(cyclopropanecarboxamido)benzo[d]thiazol-6-yl)-2,3-dihydro-1H-pyrrolo[3,2-b]pyridine-1-carboxylate (B67)

To a solution of B67-6 (50 mg, 0.09 mmol) in dichloromethane (5 mL) was added dropwise TFA (0.5 mL) at 0° C. The mixture was stirred at room temperature for 4 h. The resulting reaction was evaporated. The residue was adjusted pH to 8 by saturated aqueous NaHCO₃ and extracted with dichloromethane (20 mL*3). The combined organic layers were dried over Na₂SO₄, filtered and concentrated to give the title compound as a white solid (20 mg, 48%). ¹H NMR (400 MHz, DMSO-d₆) δ 8.43 (s, 1H), 8.28 (s, 1H), 8.17 (br s, 1H), 7.82 (d, J=7.6 Hz, 1H), 7.68 (d, J=8.0 Hz, 1H), 5.09-4.94 (m, 1H), 4.26-3.94 (m, 2H), 3.29-2.96 (m, 6H), 2.21-1.78 (m, 5H), 0.96 (s, 4H).

Step 8: 1-methylpiperidin-4-yl-6-(2-(cyclopropanecarboxamido)benzo[d]thiazol-6-yl)-2,3-dihydro-1H-pyrrolo[3,2-b]pyridine-1-carboxylate (B68)

In a solution of B67 (46 mg, 0.1 mmol) and 37% CH₂O (180 mg, 2 mmol) in 3 mL of methanol was stirred for 30 min. Then the mixture was added NaBH₃CN (13 mg, 0.2 mmol) in portions and stirred overnight. It was quenched by H₂O and extracted with dichloromethane (10 mL*3). The organic layers were dried over Na₂SO₄, filtered and concentrated. The residue was purified by silica gel column chromatography (dichloromethane/methanol=20/1) to give the title compound as a white solid (20 mg, 43%). ¹H NMR (400 MHz, CDCl₃) δ 11.33 (br s, 1H), 8.43 (s, 1H), 8.31 (s, 1H), 8.04 (s, 1H), 7.82 (d, J=8.0 Hz, 1H), 7.66 (d, J=8.0 Hz, 1H), 5.18-4.95 (m, 1H), 4.14 (t, J=8.0 Hz, 2H), 3.33 (t, J=8.0 Hz, 2H), 3.10-2.66 (m, 4H), 2.58 (s, 3H), 2.38-2.18 (m, 2H), 2.15-2.04 (m, 2H), 1.84-1.71 (m, 1H), 1.32-1.27 (m, 2H), 1.09-0.95 (m, 2H).

Example 17: Compound B69 Made by Methods H, J and N

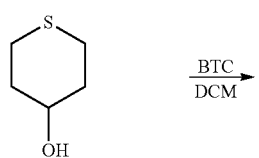

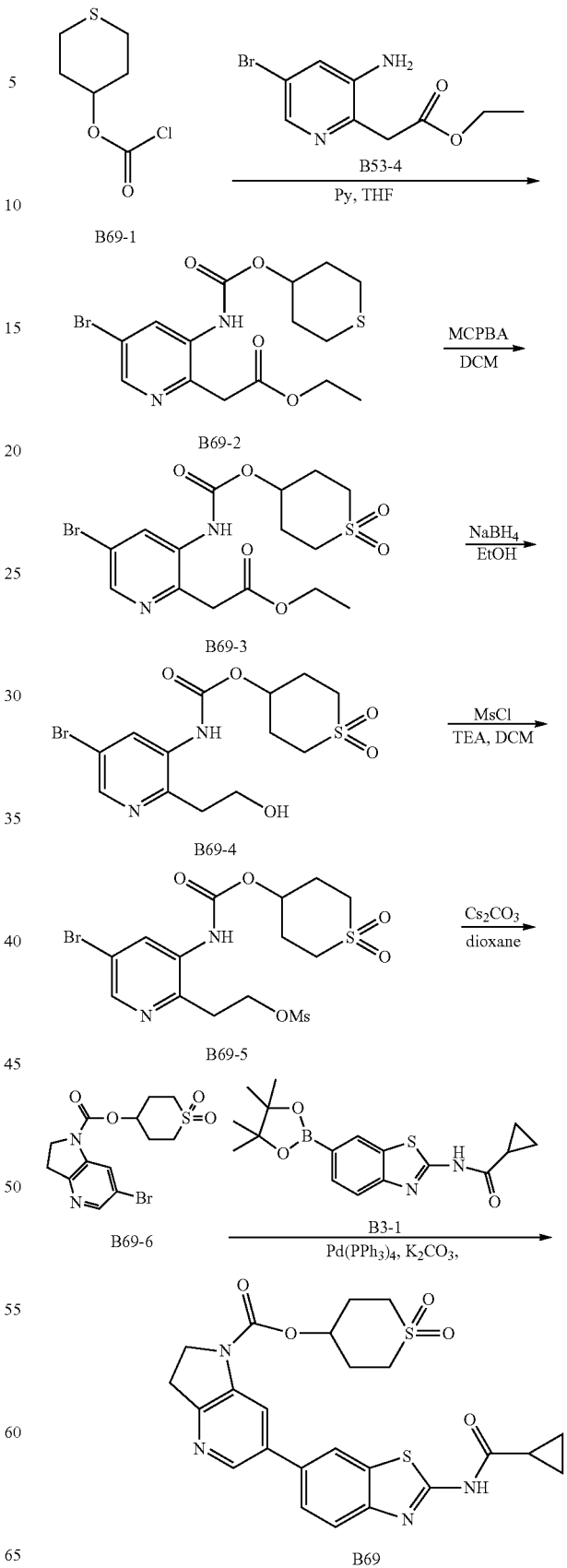

Step 1: Tetrahydro-2H-thiopyran-4-yl carbonochloridate (B69-1)

To a solution of bis(trichloromethyl)carbonate (1.2 g, 4 mmol) in 40 mL of dichloromethane was added dropwise pyridine (1.1 g, 14 mmol) at 0° C. After stirring for 10 min, a solution of tert-butyl 4-hydroxypiperidine-1-carboxylate (1 g, 8.5 mmol) in dichloromethane (10 mL) was added slowly. The mixture was stirred for 1 h. The resulting solution was filtered. The filtrate was evaporated to give the crude title compound as a colorless oil (1.5 g, 98%).

Step 2: Ethyl 2-(5-bromo-3-(((((tetrahydro-2H-thiopyran-4-yl)oxy)carbonyl)amino)pyridin-2-yl)acetate (B69-2)

In a solution of B53-4 (1.3 g, 5 mmol) and pyridine (1.2 g, 15 mmol) in THF (25 mL) was added B69-1 (1.4 g, 7.5 mmol) at 0° C. The mixture was stirred at room temperature for 4 h. The resulting reaction was evaporated and the residue was purified by silica gel column chromatography (petroleum ether/ethyl acetate=10/1) to give the title compound as a yellow solid (820 mg, 41%). $^1$H NMR (400 MHz, CDCl$_3$) δ 8.42 (br s, 1H), 8.35-8.18 (m, 2H), 4.91-4.74 (m, 1H), 4.29-4.11 (m, 2H), 3.87 (s, 2H), 2.91-2.71 (m, 2H), 2.66 (t, J=10.4 Hz, 2H), 2.30-2.10 (m, 2H), 2.07-1.84 (m, 2H), 1.30 (t, J=6.8 Hz, 3H).

Step 3: Ethyl 2-(5-bromo-3-(((((1,1-dioxidotetrahydro-2H-thiopyran-4-yl)oxy)carbonyl)amino)pyridin-2-yl)acetate (B69-3)

To a solution of B69-2 (804 mg, 2 mmol) in 50 mL of dichloromethane was added slowly 3-chloroperbenzoic acid (1.1 g, 14 mmol) at 0° C. After the mixture was stirred at room temperature overnight, saturated aqueous Na$_2$S$_2$O$_3$ (50 mL) was added to quench the redundant 3-chloroperbenzoic acid. After the organic phase was washed with saturated aqueous (50 mL*3) and evaporated, the residue was purified by silica gel column chromatography (petroleum ether/ethyl acetate=1/1) to give the title compound as a yellow oil (800 mg, 92%). $^1$H NMR (400 MHz, CDCl$_3$) δ 8.67 (br s, 1H), 8.41 (br s, 1H), 8.36 (s, 1H), 5.18-5.06 (m, 1H), 4.30-4.15 (m, 2H), 3.89 (s, 2H), 3.41-3.20 (m, 2H), 3.11-2.94 (m, 2H), 2.48-2.38 (m, 4H), 1.32 (t, J=7.2 Hz, 3H).

Step 4: 1,1-dioxidotetrahydro-2H-thiopyran-4-yl(5-bromo-2-(2-hydroxyethyl)pyridin-3-yl)carbamate (B69-4)

In a solution of B69-3 (900 mg, 2.1 mmol) in EtOH (50 mL) was added NaBH$_4$ (394 mg, 10.5 mmol) at 0° C. The mixture was stirred at room temperature overnight. The mixture was filtered to give the title compound as a white solid (700 mg, 85%). $^1$H NMR (400 MHz, DMSO-d$_6$) δ 9.28 (br s, 1H), 8.36 (d, J=8.4 Hz, 1H), 8.18 (d, J=8.0 Hz, 1H), 5.05-4.90 (m, 1H), 3.87-3.61 (m, 2H), 3.25-3.10 (m, 4H), 3.02-2.82 (m, 2H), 2.33-2.05 (m, 4H).

2-(5-bromo-3-(((((1,1-dioxidotetrahydro-2H-thiopyran-4-yl)oxy)carbonyl)amino)pyridin-2-yl)ethyl methanesulfonate (B69-5)

In a solution of B69-4 (700 mg, 1.8 mmol) and TEA (200 mg, 2.0 mmol) in dichloromethane (20 mL) was added slowly MsCl (224 mg, 2.0 mmol) at 0° C. The mixture was stirred at room temperature for 2 h. The mixture was treated with brine (50 mL) and extracted with ethyl acetate (30 mL*2). The combined organic layers were dried over Na$_2$SO$_4$, filtered and concentrated to give the title compound as a brown solid (850 mg).

Step 5: 1,1-dioxidotetrahydro-2H-thiopyran-4-yl6-bromo-2,3-dihydro-1H-pyrrolo[3,2-b]pyridine-1-carboxylate (B69-6).

A mixture of B69-5 (844 mg, 1.8 mmol) and Cs$_2$CO$_3$ (717 mg, 2.2 mmol) in dioxane (20 mL) was stirred at 110° C. for 5 h. After cooling to room temperature, the mixture was filtered and evaporated. The residue was purified by silica gel column chromatography (petroleum ether/ethyl acetate=5/1) to give the title compound as a white solid (600 mg, 89%). $^1$H NMR (400 MHz, CDCl$_3$) δ 8.21 (s, 1H), 8.18 (s, 1H), 5.22-5.11 (m, 1H), 4.11 (t, J=8.8 Hz, 2H), 3.30-3.18 (m, 4H), 3.10-3.05 (m, 2H), 2.55-2.38 (m, 4H).

Step 6: 1,1-dioxidotetrahydro-2H-thiopyran-4-yl6-(2-(cyclopropanecarboxamido)benzo[d]thiazol-6-yl)-2,3-dihydro-1H-pyrrolo[3,2-b]pyridine-1-carboxylate (B69)

A mixture of B69-6 (75 mg, 0.2 mmol), B3-1 (124 mg, 0.36 mmol), Pd(PPh$_3$)$_4$ (23 mg, 0.02 mmol), K$_2$CO$_3$ (70 mg, 0.5 mmol) and H$_2$O (1 mL) in dioxane (7 mL) was stirred at 80° C. under N$_2$ overnight. After cooling to room temperature, the mixture was evaporated and the residue was purified by silica gel column chromatography (dichloromethane/methanol=50/1) to give the title compound as a white solid (57 mg, 56%). $^1$H NMR (400 MHz, DMSO-d$_6$) δ 12.73 (br s, 1H), 8.43 (s, 1H), 8.28 (s, 1H), 8.18 (br s, 1H), 7.82 (d, J=8.4 Hz, 1H), 7.68 (d, J=8.4 Hz, 1H), 5.22-4.98 (m, 1H), 4.26-3.97 (m, 2H), 3.31-3.12 (m, 6H), 2.38-2.18 (m, 4H), 2.07-1.95 (m, 1H), 1.09-0.88 (m, 4H).

Example 18: Compound 80 Made by Method O

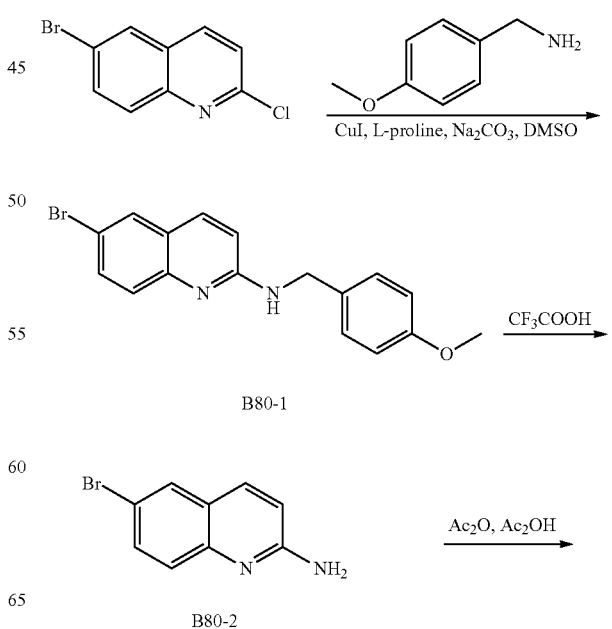

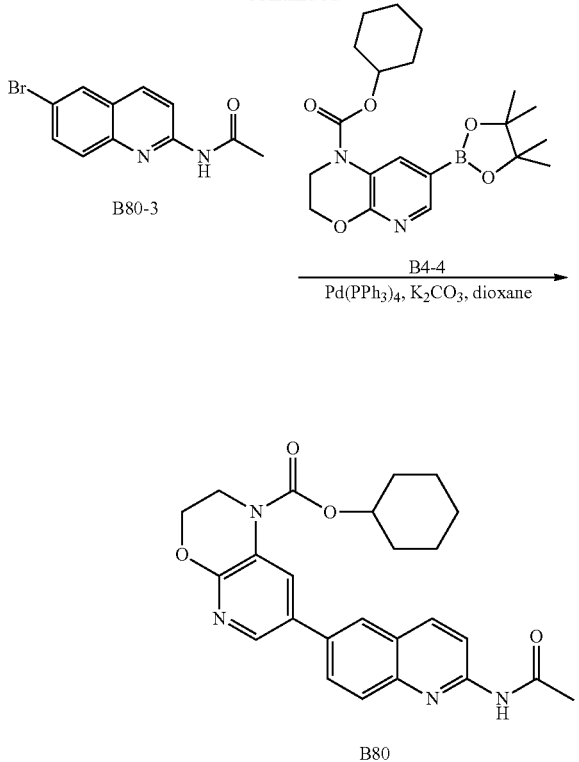

δ 7.71 (d, J=7.2 Hz, 2H), 7.58 (s, 2H), 7.32 (d, J=8.0 Hz, 2H), 8.88 (d, J=8.0 Hz, 2H), 8.62 (d, J=8.8 Hz, 1H), 5.02 (s, 1H), 4.63 (d, J=4.8 Hz, 2H), 3.80 (s, 3H).

Step 2: 6-bromoquinolin-2-amine (B80-2)

A mixture of B80-1 (100 mg, 0.29 mmol) in TFA (4 mL) was stirred at 80° C. overnight. After cooling to room temperature, the mixture was evaporated. The residue was dissolved in 1N HCl (10 mL) and washed with ethyl acetate (10 mL*3). It was adjusted pH to 9 by 1N NaOH and extracted with dichloromethane (20 mL*3). The organic layer was dried over $Na_2SO_4$, filtered and concentrated to give the title compound as a yellow oil (50 mg, 78%).

Step 3: N-(6-bromoquinolin-2-yl)acetamide (B80-3)

To a solution of B80-2 (45 mg, 0.2 mmol) in acetic acid (2 mL) was added slowly acetic anhydride (0.5 mL) at 0° C. The mixture was stirred at 80° C. overnight. After cooling to room temperature, the mixture was evaporated. After cooling to room temperature, the mixture was treated with aqueous $NaHCO_3$ (20 mL) and extracted with ethyl acetate (20 mL*2). The combined organic layers were dried over $Na_2SO_4$, filtered and concentrated to give the title compound as a white solid (30 mg, 57%). $^1$H NMR (400 MHz, DMSO-$d_6$) δ 10.90 (s, 1H), 8.32 (s, 2H), 8.19 (d, J=1.6 Hz, 1H), 7.84-7.77 (m, 1H), 7.72 (d, J=8.8 Hz, 1H), 2.15 (s, 3H).

Step 4: Cyclohexyl7-(2-acetamidoquinolin-6-yl)-2,3-dihydro-1H-pyrido[2,3-b][1,4]oxazine-1-carboxylate (B80)

A mixture of B80-3 (28 mg, 0.11 mmol), B4-4 (70 mg, 0.18 mmol), Pd(PPh$_3$)$_4$ (13 mg, 0.01 mmol), $K_2CO_3$ (38 mg, 0.28 mmol) and $H_2O$ (1 mL) in dioxane (7 mL) was stirred at 80° C. under $N_2$ overnight. The mixture was evaporated and the residue was purified by silica gel column chromatography (dichloromethane/methanol=80/1) to give the title compound as a white solid (15 mg, 31%). $^1$H NMR (400 MHz, DMSO-$d_6$) δ 10.86 (s, 1H), 8.70 (s, 1H), 8.43-8.36 (m, 1H), 8.35-8.28 (m, 2H), 8.13 (s, 1H), 7.96 (d, J=8.4 Hz, 1H), 7.87 (d, J=8.4 Hz, 1H), 8.87-8.69 (m, 1H), 4.42 (s, 2H), 3.93 (s, 2H), 2.16 (s, 3H), 1.95-1.82 (m, 2H), 1.77-1.61 (m, 2H), 1.61-1.26 (m, 6H).

Step 1: 6-bromo-N-(4-methoxybenzyl)quinolin-2-amine (B80-1)

A mixture of 6-bromo-2-chloroquinoline (242 mg, 1 mmol), CuI (19 mg, 0.1 mmol), L-Proline (23 mg, 0.2 mmol), $Na_2CO_3$ (212 mg, 2 mmol) and (4-methoxyphenyl)methylamine (410 mg, 3 mmol) in DMSO (10 mL) was stirred at 80° C. overnight. After cooling to room temperature, the mixture was filtered and evaporated. The residue was purified by silica gel column chromatography (petroleum ether/ethyl acetate=40/1) to give the title compound as a yellow solid (110 mg, 32%). $^1$H NMR (400 MHz, CDCl$_3$)

TABLE 1

| | Selected compounds synthesized by Methods A-O | | |
|---|---|---|---|
| Compd. | Structure | Method | $^1$H NMR |
| B1 |  | A | $^1$H NMR (400 MHz, CDCl$_3$) δ 8.55 (s, 1H), 8.17 (s, 1H), 7.92 (s, 1H), 7.57 (s, 2H), 7.45-7.38 (m, 2H), 4.82-4.75 (m, 1H), 4.39 (s, 2H), 3.90 (s, 2H), 1.93-1.81 (m, 2H), 1.73-1.61 (m, 2H), 1.59-1.12 (m, 6H). |

TABLE 1-continued

Selected compounds synthesized by Methods A-O

| Compd. | Structure | Method | ¹H NMR |
|---|---|---|---|
| B2 | 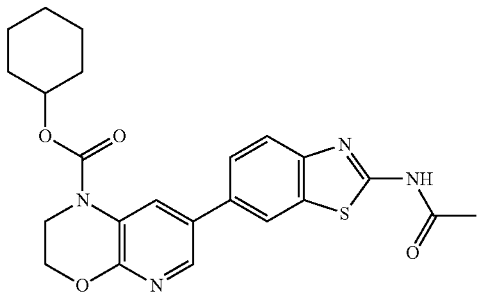 [SMILES: CC(=O)Nc1nc2ccc(-c3cnc4c(c3)N(C(=O)OC3CCCCC3)CCO4)cc2s1] | A | ¹H NMR (400 MHz, DMSO-d6) δ 12.40 (s, 1H), 8.62 (s, 1H), 8.24 (d, J = 5.9 Hz, 2H), 7.81 (d, J = 8.4 Hz, 1H), 7.65 (d, J = 8.3 Hz, 1H), 4.79 (s, 1H), 4.84-4.73 (m, 2H), 3.92 (s, 2H), 2.21 (s, 3H), 1.94-1.79 (m, 2H), 1.74-1.61 (m, 2H), 1.60-1.44 (m, 3H), 1.45-1.28 (m, 3H). |
| B3 | 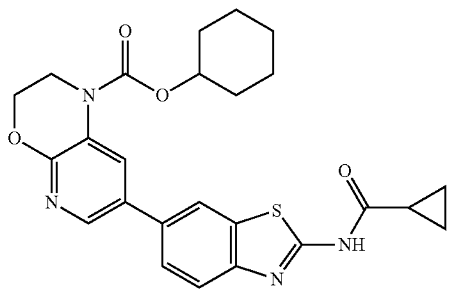 [SMILES: O=C(Nc1nc2ccc(-c3cnc4c(c3)N(C(=O)OC3CCCCC3)CCO4)cc2s1)C1CC1] | A | ¹H NMR (400 MHz, CDCl₃) δ 11.43 (s, 1H), 8.69 (s, 1H), 8.24 (s, 1H), 8.00 (s, 1H), 7.83 (d, J = 8.4 Hz, 1H), 7.63 (d, J = 8.4 Hz, 1H), 4.94-4.82 (m, 1H), 4.45 (s, 2H), 3.99 (s, 2H), 2.03-1.89 (m, 2H), 1.84-1.34 (m, 11H) 1.02 (d, J = 4.6 Hz, 2H). |
| B4 | 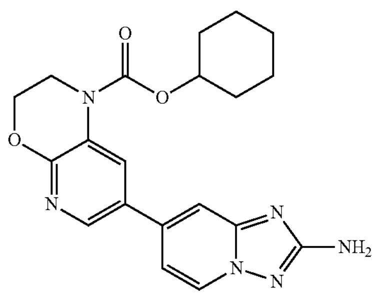 [SMILES: Nc1nc2cc(-c3cnc4c(c3)N(C(=O)OC3CCCCC3)CCO4)ccn2n1] | A, B | ¹H NMR (400 MHz, DMSO-d6) δ 8.83 (s, 1H), 8.54 (s, 1H), 8.25 (s, 1H), 7.66 (d, J = 9.0 Hz, 1H), 7.45 (d, J = 9.0 Hz, 1H), 6.09 (s, 2H), 4.77 (s, 1H), 4.40 (s, 2H), 3.90 (s, 2H), 1.86 (s, 2H), 1.65 (s, 2H), 1.43 (ddd, J = 31.7, 21.3, 9.4 Hz, 6H). |
| B5 | 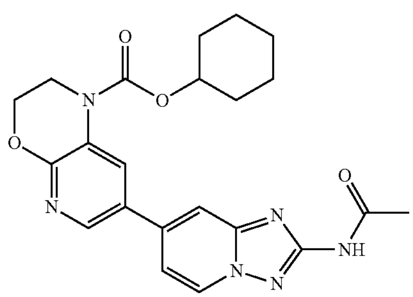 [SMILES: CC(=O)Nc1nc2cc(-c3cnc4c(c3)N(C(=O)OC3CCCCC3)CCO4)ccn2n1] | A, B | ¹H NMR (400 MHz, DMSO-d6) δ 10.82 (s, 1H), 9.18 (s, 1H), 8.62 (s, 1H), 8.31 (s, 1H), 7.87 (d, J = 9.4 Hz, 1H), 7.78 (d, J = 9.1 Hz, 1H), 4.78 (s, 1H), 4.42 (s, 2H), 3.92 (s, 2H), 2.15 (s, 3H), 1.86 (s, 2H), 1.65 (s, 2H), 1.59-1.44 (m, 3H), 1.41-1.32 (m, 2H), 1.23 (s, 1H). |
| B6 | 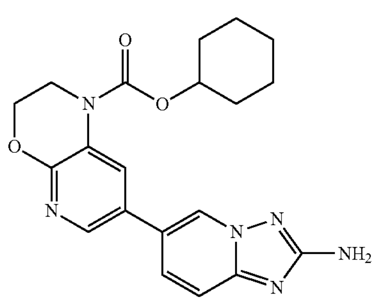 [SMILES: Nc1nc2ccc(-c3cnc4c(c3)N(C(=O)OC3CCCCC3)CCO4)cn2n1] | A, B | ¹H NMR (400 MHz, DMSO-d6) δ 8.83 (s, 1H), 8.54 (s, 1H), 8.25 (s, 1H), 7.66 (d, J = 9.0 Hz, 1H), 7.45 (d, J = 9.0 Hz, 1H), 6.09 (s, 2H), 4.77 (s, 1H), 4.40 (s, 2H), 3.90 (s, 2H), 1.86 (s, 2H), 1.65 (s, 2H), 1.60-1.44 (m, 3H), 1.35 (dd, J = 21.7, 9.8 Hz, 3H). |

TABLE 1-continued

Selected compounds synthesized by Methods A-O

| Compd. | Structure | Method | ¹H NMR |
|---|---|---|---|
| B7 | 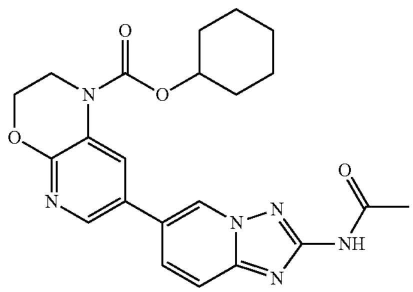 [SMILES: CC(=O)Nc1nc2ccc(-c3cnc4c(c3)N(C(=O)OC3CCCCC3)CCO4)cn2n1] | A, B | ¹H NMR (400 MHz, DMSO-d6) δ 10.82 (s, 1H), 9.18 (s, 1H), 8.62 (s, 1H), 8.31 (s, 1H), 7.87 (d, J = 9.4 Hz, 1H), 7.78 (d, J = 9.1 Hz, 1H), 4.78 (s, 1H), 4.42 (s, 2H), 3.92 (s, 2H), 2.15 (s, 3H), 1.86 (s, 2H), 1.65 (s, 2H), 1.59-1.44 (m, 3H), 1.40-1.32 (m, 2H), 1.23 (s, 1H). |
| B8 | 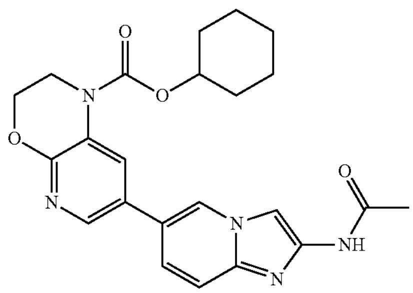 [SMILES: CC(=O)Nc1cn2cc(-c3cnc4c(c3)N(C(=O)OC3CCCCC3)CCO4)ccc2n1] | A, B | ¹H NMR (400 MHz, CDCl₃) δ 9.15 (s, 1H), 8.62 (s, 1H), 8.25 (s, 1H), 8.13 (d, J = 7.0 Hz, 2H), 7.48 (s, 1H), 7.40 (s, 1H), 4.86 (s, 1H), 4.44 (s, 2H), 3.98 (s, 2H), 2.23 (s, 3H), 1.95 (s, 2H), 1.84-1.48 (m, 8H). |
| B9 | 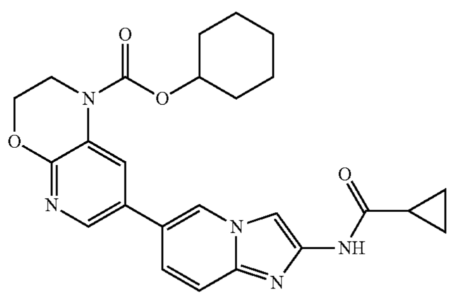 [SMILES: O=C(Nc1cn2cc(-c3cnc4c(c3)N(C(=O)OC3CCCCC3)CCO4)ccc2n1)C1CC1] | A, B | ¹H NMR (400 MHz, DMSO-d6) δ 11.00 (s, 1H), 8.86 (s, 1H), 8.57 (s, 1H), 8.21 (s, 1H), 8.08 (s, 1H), 7.52 (d, J = 9.2 Hz, 1H), 7.45 (d, J = 9.2 Hz, 1H), 4.82-4.72 (m, 1H), 4.40 (s, 2H), 3.91 (s, 2H), 2.04-1.78 (m, 3H), 1.75-1.13 (m, 8H), 0.88-0.74 (m, 4H). |
| B10 | 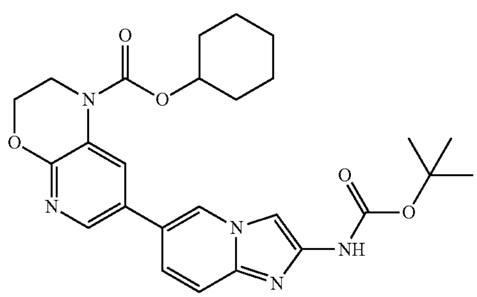 | A, B | ¹H NMR (400 MHz, CDCl₃) δ 8.59 (s, 1H), 8.18 (s, 1H), 8.13 (s, 1H), 8.03 (s, 1H), 7.83 (s, 1H), 7.53 (d, J = 9.2 Hz, 1H), 7.33 (d, J = 9.2 Hz, 1H), 4.92-4.79 (s, 1H), 4.45 (s, 2H), 3.99 (s, 2H), 2.00-1.89 (m, 2H), 1.82-1.69 (m, 2H), 1.60-1.33 (m, 15H). |
| B11 | 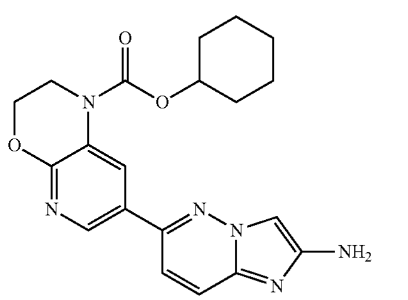 [SMILES: Nc1cn2nc(-c3cnc4c(c3)N(C(=O)OC3CCCCC3)CCO4)ccc2n1] | A, B | ¹H NMR (400 MHz, CDCl₃) δ 8.96 (s, 1H), 8.47 (s, 1H), 7.71 (s, 1H), 7.36 (s, 1H), 7.32 (d, J = 9.2 Hz, 1H), 4.96-4.85 (m, 1H), 4.47 (s, 2H), 4.32-4.06 (m, 2H), 3.99 (s, 2H), 2.02-1.88 (m, 2H), 1.84-1.71 (s, 2H), 1.60-1.33 (m, 6H). |

TABLE 1-continued

Selected compounds synthesized by Methods A-O

| Compd. | Structure | Method | ¹H NMR |
|---|---|---|---|
| B12 | 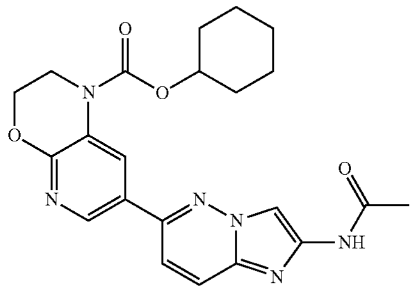 [SMILES: CC(=O)Nc1cn2nc(-c3cnc4c(c3)N(C(=O)OC3CCCCC3)CCO4)ccc2n1] | A, B | ¹H NMR (400 MHz, CDCl₃) δ 10.92 (s, 1H), 8.97 (s, 1H), 8.56 (s, 1H), 8.25 (s, 1H), 8.06 (d, J = 9.4 Hz, 1H), 7.77 (d, J = 9.5 Hz, 1H), 4.90-4.78 (m, 1H), 4.45 (s, 2H), 3.93 (s, 2H), 2.11 (s, 3H), 1.93-1.79 (m, 2H), 1.79-1.54 (m, 4H), 1.54-1.32 (m, 4H). |
| B13 | 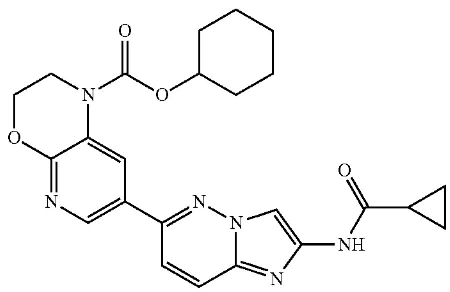 [SMILES: O=C(Nc1cn2nc(-c3cnc4c(c3)N(C(=O)OC3CCCCC3)CCO4)ccc2n1)C1CC1] | A, B | ¹H NMR (400 MHz, CDCl₃) δ 11.20 (s, 1H), 8.94 (s, 1H), 8.56 (s, 1H), 8.22 (s, 1H), 8.06 (d, J = 9.4 Hz, 1H), 7.76 (d, J = 9.4 Hz, 1H), 4.91-4.79 (m, 1H), 4.44 (s, 2H), 3.92 (s, 2H), 2.02-1.92 (m, 1H), 1.90-1.78 (s, 2H), 1.80-1.53 (m, 4H), 1.52-1.32 (m, 4H), 0.90-0.77 (m, 4H). |
| B14 | 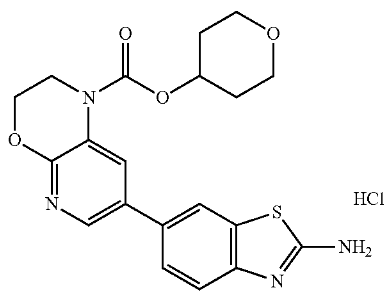 [SMILES: Nc1nc2ccc(-c3cnc4c(c3)N(C(=O)OC3CCOCC3)CCO4)cc2s1 ; Cl] | A, B, B' | ¹H NMR (400 MHz, DMSO-d6) δ 9.30 (s, 2H), 8.61 (s, 1H), 8.19 (s, 1H), 8.12 (s, 1H), 7.63 (d, J = 7.8 Hz, 1H), 7.55 (d, J = 8.3 Hz, 1H), 5.00-4.90 (m, 1H), 4.41 (s, 2H), 3.94 (s, 2H), 3.85-3.70 (m, 2H), 3.51 (t, J = 8.5 Hz, 2H), 2.02-1.88 (m, 2H), 1.72-1.61 (m, 2H). |
| B15 | 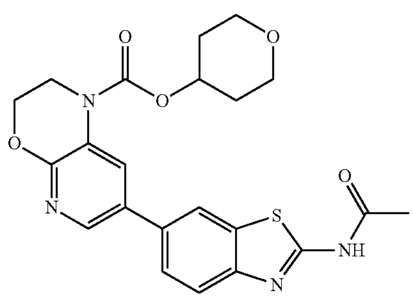 [SMILES: CC(=O)Nc1nc2ccc(-c3cnc4c(c3)N(C(=O)OC3CCOCC3)CCO4)cc2s1] | A | ¹H NMR (400 MHz, CDCl₃) δ 10.97 (s, 1H), 8.70 (s, 1H), 8.26 (s, 1H), 7.99 (s, 1H), 7.81 (d, J = 7.8 Hz, 1H), 7.63 (d, J = 7.2 Hz, 1H), 5.11-4.98 (m, 1H), 4.47 (s, 2H), 4.08-3.84 (m, 4H), 3.59 (t, J = 9.2 Hz, 2H), 2.33 (s, 3H), 2.15-1.99 (m, 2H), 1.88-1.70 (m, 2H). |
| B16 | 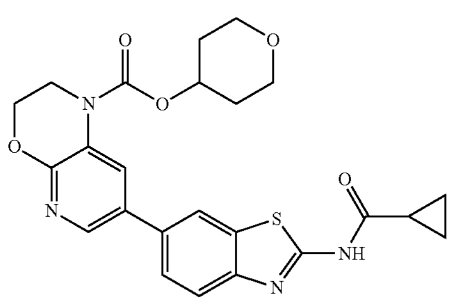 [SMILES: O=C(Nc1nc2ccc(-c3cnc4c(c3)N(C(=O)OC3CCOCC3)CCO4)cc2s1)C1CC1] | A | ¹H NMR (400 MHz, CDCl₃) δ 11.05 (s, 1H), 8.69 (s, 1H), 8.25 (s, 1H), 7.99 (s, 1H), 7.82 (d, J = 8.4 Hz, 1H), 7.62 (d, J = 8.2 Hz, 1H), 5.09-4.97 (m, 1H), 4.51-4.37 (m, 2H), 4.05-3.76 (m, 4H), 3.67-3.36 (m, 2H), 2.12-1.92 (m, 2H), 1.80-1.70 (m, 3H), 1.08-0.76 (m, 4H). |

TABLE 1-continued

Selected compounds synthesized by Methods A-O

| Compd. | Structure | Method | ¹H NMR |
|---|---|---|---|
| B17 | 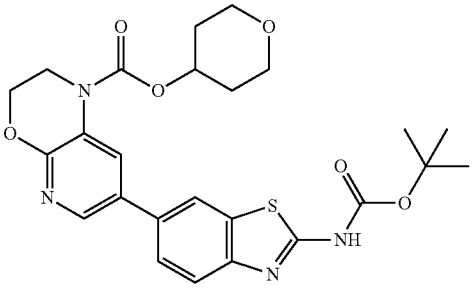 [SMILES: CC(C)(C)OC(=O)Nc1nc2ccc(-c3cnc4c(c3)N(C(=O)OC3CCOCC3)CCO4)cc2s1] | A, B | ¹H NMR (400 MHz, CDCl₃) δ 10.10 (s, 1H), 8.65 (s, 1H), 8.24 (s, 1H), 8.00-7.78 (m, 2H), 7.58 (d, J = 7.6 Hz, 1H), 5.11-4.99 (s, 1H), 4.46 (s, 2H), 4.06-3.88 (m, 4H), 3.68-3.51 (m, 2H), 2.14-1.96 (m, 2H), 1.87-1.72 (m, 2H), 1.61 (s, 9H). |
| B18 | 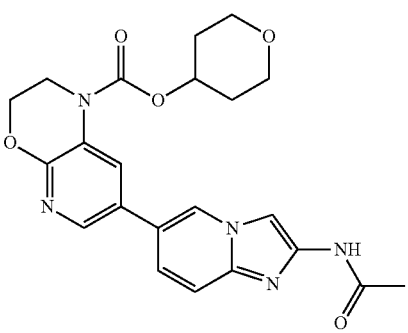 [SMILES: CC(=O)Nc1cn2cc(-c3cnc4c(c3)N(C(=O)OC3CCOCC3)CCO4)ccc2n1] | A, B | ¹H NMR (400 MHz, DMSO-d6) δ 10.70 (s, 1H), 8.88 (s, 1H), 8.58 (s, 1H), 8.26-8.08 (m, 2H), 7.68-7.42 (m, 2H), 5.02-4.88 (m, 1H), 4.41 (s, 2H), 3.94 (s, 2H), 3.85-3.73 (m, 2H), 3.50 (t, J = 8.8 Hz, 2H), 2.08 (s, 3H), 2.02-1.88 (m, 2H), 1.74-1.60 (m, 2H). |
| B19 | 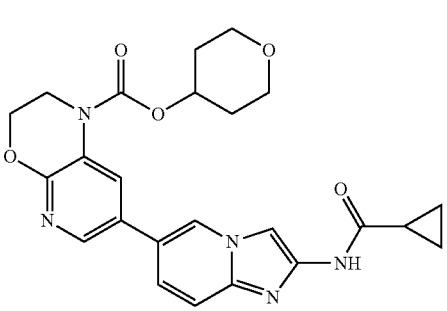 [SMILES: O=C(Nc1cn2cc(-c3cnc4c(c3)N(C(=O)OC3CCOCC3)CCO4)ccc2n1)C1CC1] | A, B | ¹H NMR (400 MHz, DMSO-d6) δ 10.98 (s, 1H), 8.86 (s, 1H), 8.58 (br s, 1H), 8.21 (s, 1H), 8.09 (s, 1H), 7.52 (d, J = 9.2 Hz, 1H), 7.44 (d, J = 8.8 Hz, 1H), 5.01-4.90 (m, 1H), 4.42 (s, 2H), 3.94 (s, 2H), 3.86-3.74 (m, 2H), 3.50 (t, J = 8.4 Hz, 2H), 2.02-1.87 (m, 3H), 1.74-1.60 (m, 2H), 0.89-0.74 (m, 4H). |
| B20 | 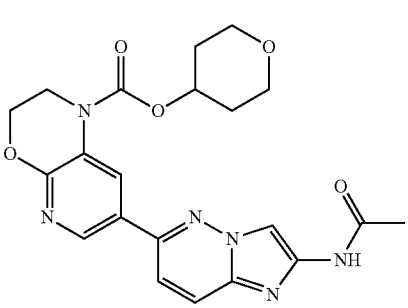 | A, B | ¹H NMR (400 MHz, DMSO-d6) δ 10.89 (s, 1H), 8.99 (s, 1H), 8.57 (s, 1H), 8.27 (s, 1H), 8.06 (d, J = 9.3 Hz, 1H), 7.76 (d, J = 9.3 Hz, 1H), 5.07-4.96 (m, 1H), 4.46 (s, 2H), 4.00-3.79 (m, 4H), 3.61-3.49 (m, 2H), 2.11 (s, 3H), 2.04-1.92 (m, 2H), 1.76-1.63 (m, 2H). |
| B21 | 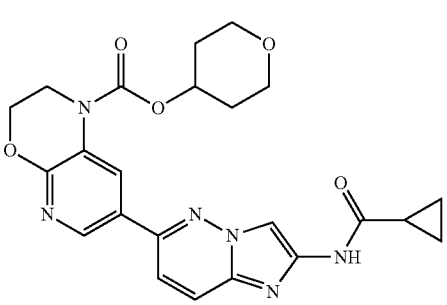 [SMILES: O=C(Nc1cn2nc(-c3cnc4c(c3)N(C(=O)OC3CCOCC3)CCO4)ccc2n1)C1CC1] | A, B | ¹H NMR (400 MHz, DMSO-d6) δ 11.20 (s, 1H), 8.97 (s, 1H), 8.57 (s, 1H), 8.25 (s, 1H), 8.07 (d, J = 9.4 Hz, 1H), 7.77 (d, J = 9.4 Hz, 1H), 5.08-4.95 (m, 1H), 4.46 (s, 2H), 4.00-3.76 (m, 4H), 3.63-3.44 (m, 2H), 2.07-1.80 (m, 3H), 1.76-1.56 (m, 2H), 0.90-0.69 (m, 4H). |

TABLE 1-continued

Selected compounds synthesized by Methods A-O

| Compd. | Structure | Method | ¹H NMR |
|---|---|---|---|
| B22 | 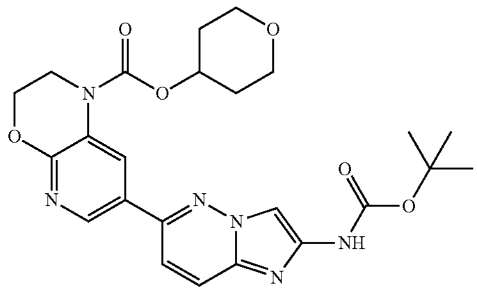 [SMILES: CC(C)(C)OC(=O)Nc1cn2nc(-c3cnc4c(c3)N(C(=O)OC3CCOCC3)CCO4)ccc2n1] | A, B | ¹H NMR (400 MHz, CDCl₃) δ 8.98 (s, 1H), 8.52 (s, 1H), 8.39-8.12 (m, 2H), 7.89 (d, J = 8.8 Hz, 1H), 7.41 (d, J = 9.2 Hz, 1H), 5.17-5.04 (m, 1H), 4.49 (s, 2H), 4.07-3.90 (m, 4H), 3.64 (t, J = 8.8 Hz, 2H), 2.15-1.99 (m, 2H), 1.89-1.75 (m, 2H), 1.58 (s, 9H). |
| B23 | 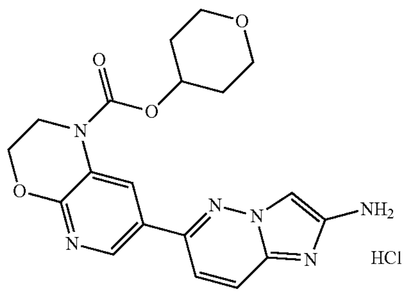 [SMILES: Nc1cn2nc(-c3cnc4c(c3)N(C(=O)OC3CCOCC3)CCO4)ccc2n1 ; Cl] | A, B, B' | ¹H NMR (400 MHz, DMSO-d6) δ 8.99 (s, 1H), 8.59 (s, 1H), 8.12 (d, J = 9.0 Hz, 1H), 7.99 (d, J = 8.6 Hz, 1H), 7.56 (s, 1H), 5.09-4.97 (m, 1H), 4.52-4.38 (m, 2H), 4.00-3.90 (m, 2H), 3.90-3.82 (m, 2H), 3.65-3.51 (m, 2H), 2.05-1.92 (m, 2H), 1.77-1.62 (m, 2H). |
| B24 | 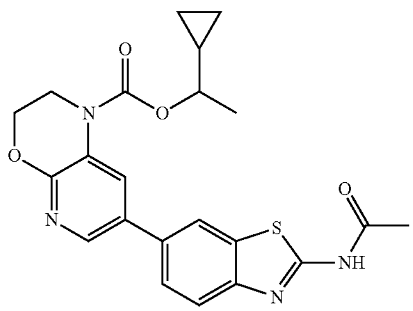 [SMILES: CC(=O)Nc1nc2ccc(-c3cnc4c(c3)N(C(=O)OC(C)C3CC3)CCO4)cc2s1] | A | ¹H NMR (400 MHz, DMSO-d₆) δ 12.40 (s, 1H), 8.59 (s, 1H), 8.23 (d, J = 4.4 Hz, 2H), 7.81 (d, J = 8.4 Hz, 1H), 7.65 (d, J = 8.4 Hz, 1H), 4.49-4.30 (m, 3H), 4.04-3.80 (m, 2H), 2.21 (s, 3H), 1.35 (d, J = 5.6 Hz, 3H), 1.17-1.07 (m, 1H), 0.40-0.30 (m, 4H). |
| B25 | 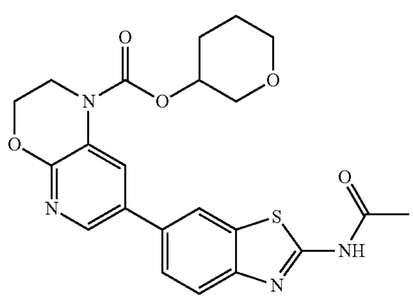 | A | ¹H NMR (400 MHz, DMSO-d₆) δ 12.41 (s, 1H), 8.62 (s, 1H), 8.27 (s, 2H), 7.81 (d, J = 8.4 Hz, 1H), 7.71 (d, J = 8.0 Hz, 1H), 4.87-4.77 (m, 1H), 4.48-4.38 (m, 2H), 3.98-3.88 (m, 2H), 3.78-3.65 (m, 3H), 3.61-3.50 (m, 1H), 2.21 (s, 3H), 2.05-1.70 (m, 3H), 1.55-1.41 (m, 1H). |
| B26 | 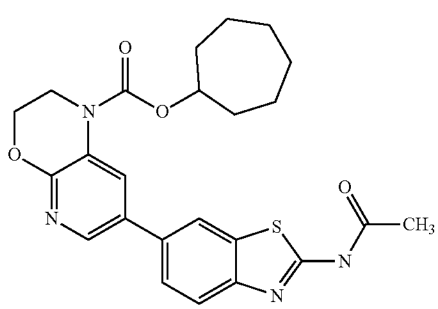 [SMILES: CC(=O)Nc1nc2ccc(-c3cnc4c(c3)N(C(=O)OC3CCCCCC3)CCO4)cc2s1] | A | ¹H NMR (400 MHz, DMSO-d₆) δ 12.39 (s, 1H), 8.60 (s, 1H), 8.23 (s, 2H), 7.92-7.54 (m, 2H), 5.09-4.82 (m, 1H), 4.40 (s, 2H), 3.91 (s, 2H), 2.21 (s, 3H), 2.07-1.45 (m, 12 H). |

TABLE 1-continued

Selected compounds synthesized by Methods A-O

| Compd. | Structure | Method | ¹H NMR |
|---|---|---|---|
| B27 | 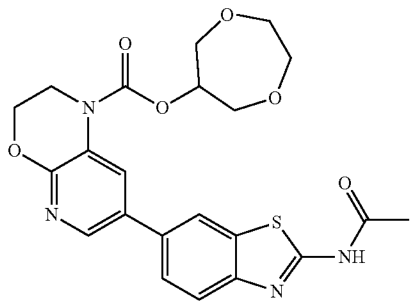 [SMILES: CC(=O)Nc1nc2ccc(-c3cnc4c(c3)N(C(=O)OC3COCCOC3)CCO4)cc2s1] | A, B | ¹H NMR (400 MHz, DMSO-$d_6$) δ 8.60 (br s, 1H), 8.26 (s, 2H), 7.80 (d, J = 8.4 Hz, 1H), 7.71 (d, J = 8.0 Hz, 1H), 5.13-5.02 (m, 1H), 4.46-4.36 (m, 2H), 4.09-3.98 (m, 2H), 3.95-3.83 (m, 4H), 3.79-3.66 (m, 4H), 2.21 (s, 3H). |
| B28 | 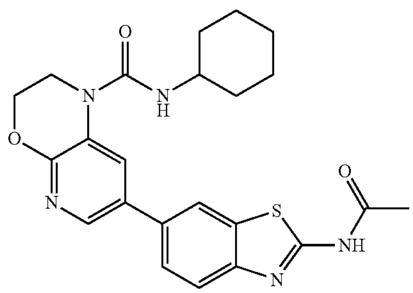 [SMILES: CC(=O)Nc1nc2ccc(-c3cnc4c(c3)N(C(=O)NC3CCCCC3)CCO4)cc2s1] | A | ¹H NMR (400 MHz, DMSO-$d_6$) δ 12.39 (s, 1H), 8.43 (s, 1H), 8.20 (s, 1H), 8.12 (s, 1H), 7.79 (d, J = 8.4 Hz, 1H), 7.63 (d, J = 8.4 Hz, 1H), 6.98 (d, J = 7.2 Hz, 1H), 4.34 (s, 2H), 3.76 (s, 2H), 3.62-3.46 (m, 1H), 2.21 (s, 3H), 1.92-1.51 (m, 5H), 1.35-1.20 (m, 5H). |
| B29 | 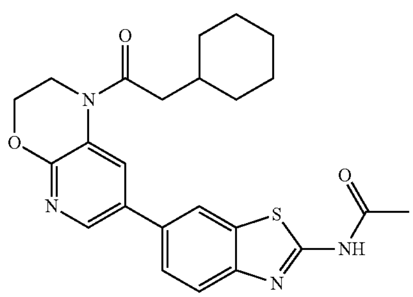 | A | ¹H NMR (400 MHz, DMSO-$d_6$) δ 12.40 (s, 1H), 8.74 (s, 1H), 8.32-8.16 (m, 2H), 7.81 (d, J = 8.4 Hz, 1H), 7.65 (d, J = 8.0 Hz, 1H), 4.41 (s, 2H), 3.94 (s, 2H), 2.21 (s, 3H), 1.91-1.48 (m, 7H), 1.32-0.85 (m, 6H). |
| B30 | 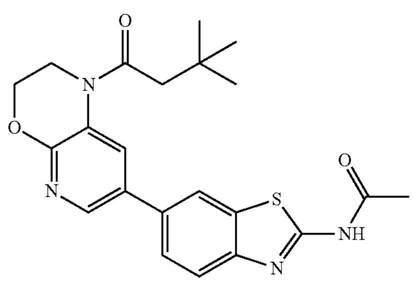 [SMILES: CC(=O)Nc1nc2ccc(-c3cnc4c(c3)N(C(=O)CC(C)(C)C)CCO4)cc2s1] | A | 1H NMR (400 MHz, DMSO-$d_6$) δ 12.40 (s, 1H), 8.61 (s, 1H), 8.35-8.11 (m, 2H), 7.81 (d, J = 8.0 Hz, 1H), 7.66 (d, J = 7.6 Hz, 1H), 4.41 (s, 2H), 3.98 (s, 2H), 2.55 (s, 2H), 2.21 (s, 3H), 1.04 (s, 9H). |
| B31 | 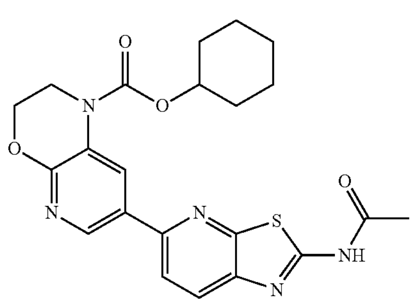 [SMILES: CC(=O)Nc1nc2ccc(-c3cnc4c(c3)N(C(=O)OC3CCCCC3)CCO4)nc2s1] | A, B | ¹H NMR (400 MHz, DMSO-$d_6$) δ 12.51 (s, 1H), 9.06 (s, 1H), 8.61 (s, 1H), 8.28-7.89 (m, 2H), 4.87 (s, 1H), 4.43 (s, 2H), 3.92 (s, 2H), 2.23 (s, 3H), 1.92-1.43 (m, 10H). |

TABLE 1-continued

Selected compounds synthesized by Methods A-O

| Compd. | Structure | Method | ¹H NMR |
|---|---|---|---|
| B32 | 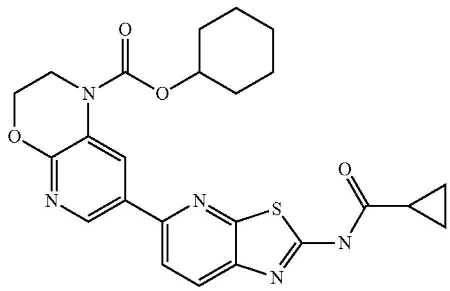 [SMILES: O=C(Nc1nc2ccc(-c3cnc4c(c3)N(C(=O)OC3CCCCC3)CCO4)nc2s1)C1CC1] | A, B | ¹H NMR (400 MHz, DMSO-d$_6$) δ 12.83 (s, 1H), 9.05 (s, 1H), 8.61 (s, 1H), 8.15 (d, J = 8.8 Hz, 1H), 8.03 (d, J = 8.8 Hz, 1H), 4.93-4.82 (m, 1H), 4.43 (s, 2H), 3.92 (s, 2H), 2.11-1.98 (m, 1H), 1.95-1.79 (m, 2H), 1.77-1.55 (m, 4H), 1.54-1.34 (m, 4H). 1.06-0.93 (m, 4H). |
| B33 | 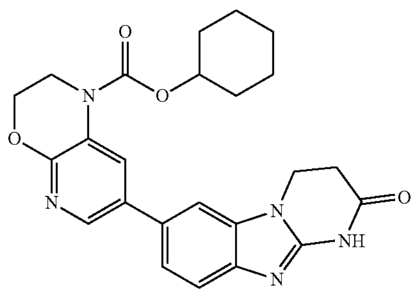 [SMILES: O=C1CCn2c(nc3ccc(-c4cnc5c(c4)N(C(=O)OC4CCCCC4)CCO5)cc32)N1] | C | ¹H NMR (400 MHz, DMSO-d$_6$) δ 11.49 (s, 1H), 8.59 (s, 1H), 8.22 (s, 1H), 7.67 (s, 1H), 7.48 (d, J = 8.0 Hz, 1H), 7.34 (d, J = 7.6 Hz, 1H), 4.84-4.73 (m, 1H), 4.39 (s, 2H), 4.35-4.25 (m, 2H), 3.91 (s, 2H), 2.97-2.86 (m, 2H), 1.95-1.80 (m, 2H), 1.73-1.60 (m, 2H), 1.60-1.27 (m, 6H). |
| B34 | 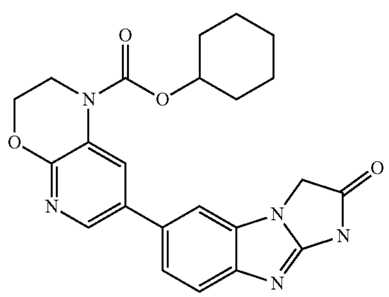 [SMILES: O=C1Cn2c(nc3ccc(-c4cnc5c(c4)N(C(=O)OC4CCCCC4)CCO5)cc32)N1] | C | ¹H NMR (400 MHz, DMSO-d$_6$) δ 8.59 (s, 1H), 8.19 (s, 1H), 7.59-7.47 (m, 2H), 7.33 (d, J = 8.0 Hz, 1H), 4.83-4.74 (m, 1H), 4.68 (s, 2H), 4.39 (s, 2H), 3.91 (s, 2H), 1.94-1.79 (m, 2H), 1.76-1.61 (m, 2H), 1.61-1.27 (m, 6H). |
| B35 | 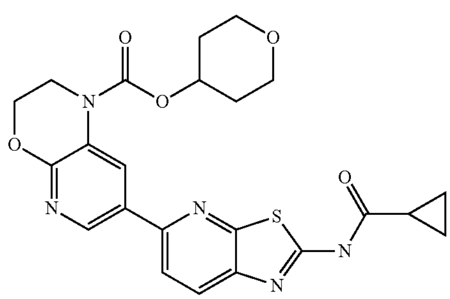 | A, B | ¹H NMR (400 MHz, DMSO-d$_6$) δ 12.80 (s, 1H), 9.06 (s, 1H), 8.61 (s, 1H), 8.15 (d, J = 8.0 Hz, 1H), 8.03 (d, J = 8.4 Hz, 1H), 5.08-4.89 (m, 1H), 4.43 (s, 2H), 4.03-3.72 (m, 4H), 3.54 (s, 2H), 2.09-1.81 (m, 3H), 1.77-1.54 (m, 2H), 1.04-0.86 (m, 4H). |
| B36 | 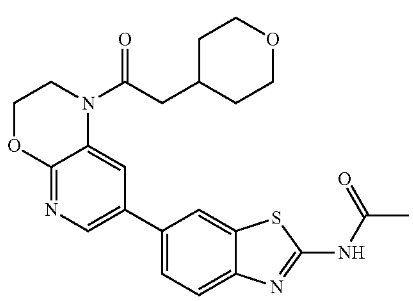 [SMILES: CC(=O)Nc1nc2ccc(-c3cnc4c(c3)N(C(=O)CC3CCOCC3)CCO4)cc2s1] | A | ¹H NMR (400 MHz, DMSO-d$_6$) δ 12.38 (br s, 1H), 8.75 (br s, 1H), 8.32-8.18 (m, 2H), 7.81 (d, J = 8.4 Hz, 1H), 7.65 (d, J = 8.0 Hz, 1H), 4.42 (s, 2H), 3.95 (s, 2H), 3.87-3.78 (m, 2H), 3.31-3.25 (m, 2H), 2.64-2.54 (m, 2H), 2.21 (s, 3H), 2.09-1.97 (m, 1H), 1.73-1.59 (m, 2H), 1.32-1.21 (m, 2H). |

TABLE 1-continued

Selected compounds synthesized by Methods A-O

| Compd. | Structure | Method | ¹H NMR |
|---|---|---|---|
| B37 | 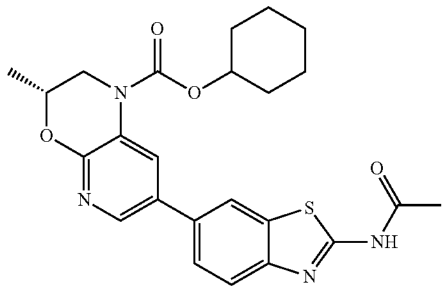 [SMILES: CC(=O)Nc1nc2ccc(-c3cnc4c(c3)N(C(=O)OC3CCCCC3)C[C@@H](C)O4)cc2s1] | D | ¹H NMR (400 MHz, DMSO-d$_6$) δ 12.41 (s, 1H), 8.56 (s, 1H), 8.32-8.20 (m, 2H), 7.81 (d, J = 8.4 Hz, 1H), 7.65 (d, J = 8.0 Hz, 1H), 4.88-4.71 (m, 1H), 4.56-4.45 (m, 1H), 4.14 (d, J = 12.0 Hz, 1H), 3.48-3.33 (m, 1H), 2.21 (s, 3H), 1.94-1.78 (m, 2H), 1.76-1.60 (m, 2H), 1.58-1.30 (m, 9H). |
| B38 | 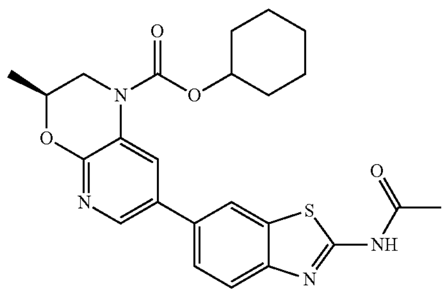 [SMILES: CC(=O)Nc1nc2ccc(-c3cnc4c(c3)N(C(=O)OC3CCCCC3)C[C@H](C)O4)cc2s1] | D | ¹H NMR (400 MHz, DMSO-d$_6$) δ 12.41 (s, 1H), 8.56 (s, 1H), 8.31-8.17 (m, 2H), 7.80 (d, J = 8.4 Hz, 1H), 7.65 (d, J = 7.6 Hz, 1H), 4.85-4.73 (m, 1H), 4.57-4.46 (m, 1H), 4.14 (d, J = 12.0 Hz, 1H), 3.45-3.33 (m, 1H), 2.21 (s, 3H), 1.94-1.79 (m, 2H), 1.74-1.69 (m, 2H), 1.59-1.28 (m, 9H). |
| B39 | 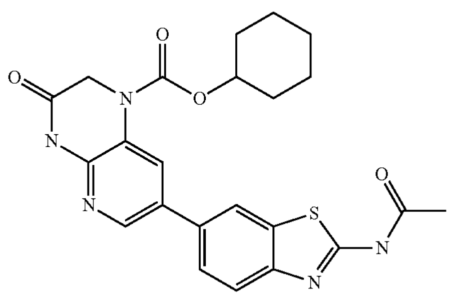 [SMILES: CC(=O)Nc1nc2ccc(-c3cnc4c(c3)N(C(=O)OC3CCCCC3)CC(=O)N4)cc2s1] | E | ¹H NMR (400 MHz, DMSO-d$_6$) δ 12.43 (s, 1H), 10.88 (s, 1H), 8.43 (s, 1H), 8.31 (s, 1H), 7.88-7.76 (m, 1H), 7.70-7.68 (m, 1H), 7.57 (s, 2H), 4.75 (s, 1H), 4.39 (s, 2H), 2.21 (s, 3H), 1.84-1.76 (m, 2H), 1.72-1.62 (m, 2H), 1.56-1.42 (m, 3H), 1.39-1.28 (m, 3H). |
| B40 | 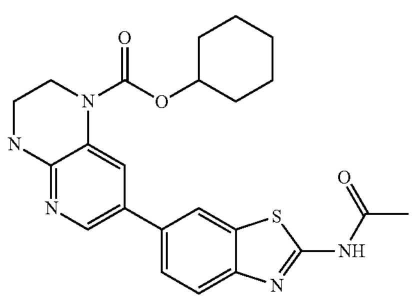 [SMILES: CC(=O)Nc1nc2ccc(-c3cnc4c(c3)N(C(=O)OC3CCCCC3)CCN4)cc2s1] | F | ¹H NMR (400 MHz, DMSO-d$_6$) δ 12.36 (s, 1H), 8.13 (s, 2H), 7.76 (d, J = 8.4 Hz, 1H), 7.59 (d, J = 8.0 Hz, 1H), 7.10 (s, 1H), 4.74 (s, 1H), 3.73 (s, 2H), 3.42-3.38 (m, 2H), 2.20 (s, 3H), 1.93-1.75 (m, 2H), 1.73-1.60 (m, 2H), 1.55-1.43 (m, 3H), 1.39-1.33 (m, 3H). |
| B41 | 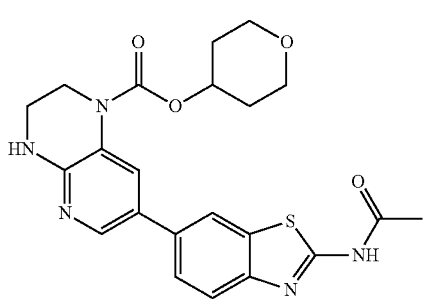 [SMILES: CC(=O)Nc1nc2ccc(-c3cnc4c(c3)N(C(=O)OC3CCOCC3)CCN4)cc2s1] | F | ¹H NMR (400 MHz, DMSO-d$_6$) δ 12.36 (s, 1H), 8.14 (d, J = 4.4 Hz, 2H), 7.76 (d, J = 8.4 Hz, 1H), 7.59 (d, J = 8.4 Hz, 1H), 7.18 (s, 1H), 4.91 (s, 1H), 3.76 (s, 4H), 3.55-3.42 (m, 4H), 2.21 (s, 3H), 1.99-1.87 (m, 2H), 1.68-1.56 (m, 2H). |

TABLE 1-continued

Selected compounds synthesized by Methods A-O

| Compd. | Structure | Method | ¹H NMR |
|---|---|---|---|
| B42 | 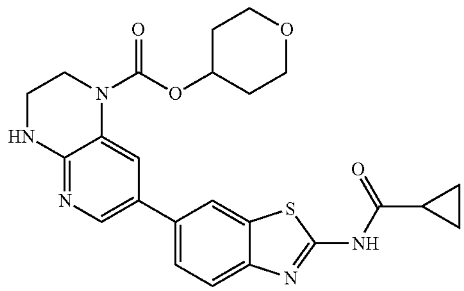 [SMILES: O=C(Nc1nc2ccc(-c3cnc4c(c3)N(C(=O)OC3CCOCC3)CCN4)cc2s1)C1CC1] | F | ¹H NMR (400 MHz, DMSO-d$_6$) δ 12.66 (s, 1H), 8.20-8.00 (m, 3H), 7.82-7.78 (m, 1H), 7.66-7.55 (m, 1H), 7.18-7.08 (m, 1H), 4.92 (s, 1H), 3.76 (s, 4H), 3.56-3.47 (m, 2H), 2.10-1.85 (s, 4H), 1.64 (s, 2H), 1.23 (s, 1H), 0.95 (s, 4H). |
| B43 | 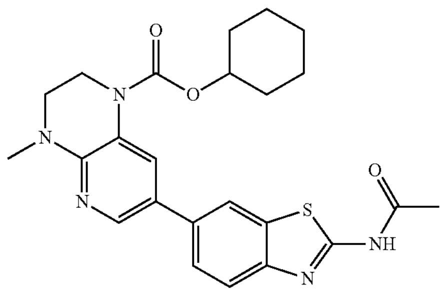 [SMILES: CC(=O)Nc1nc2ccc(-c3cnc4c(c3)N(C(=O)OC3CCCCC3)CCN4C)cc2s1] | F, G | ¹H NMR (400 MHz, DMSO-d$_6$) δ 12.35 (s, 1H), 8.22 (s, 1H), 8.14-8.08 (m, 2H), 7.77-7.75 (m, 1H), 7.61-7.59 (m, 1H), 4.74 (s, 1H), 3.83 (s, 2H), 3.46 (s, 2H), 3.12 (s, 3H), 2.21 (s, 3H), 1.92-1.78 (m, 2H), 1.74-1.58 (m, 2H), 1.57-1.43 (m, 3H), 1.40-1.28 (m, 3H). |
| B44 | 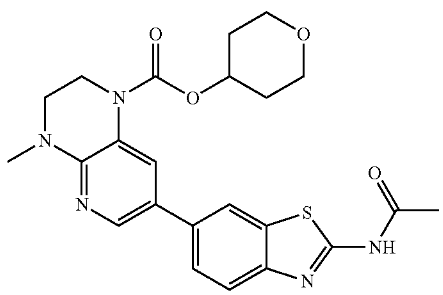 | F, G | ¹H NMR (400 MHz, DMSO-d$_6$) δ 12.37 (br s, 1H), 8.32-8.03 (m, 3H), 7.87-7.54 (m, 2H), 5.01-4.84 (m, 1H), 3.94-3.72 (m, 4H), 3.58-3.46 (m, 4H), 3.12 (s, 3H), 2.21 (s, 3H), 2.05-1.88 (m, 2H), 1.72-1.53 (m, 2H). |
| B45 | 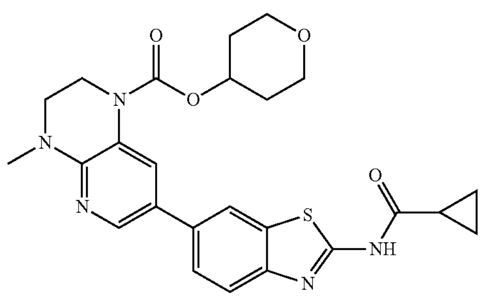 [SMILES: CN1CCN(C(=O)OC2CCOCC2)c2cc(-c3ccc4nc(NC(=O)C5CC5)sc4c3)cnc21] | F, G | ¹H NMR (400 MHz, DMSO-d$_6$) δ 12.67 (br s, 1H), 8.78-8.07 (m, 3H), 7.77 (d, J = 8.0 Hz, 1H), 7.62 (d, J = 6.8 Hz, 1H), 4.97-4.85 (m, 1H), 3.92-3.70 (m, 4H), 3.59-3.40 (m, 4H), 3.12 (s, 3H), 2.04-1.87 (m, 3H), 1.71-1.53 (m, 2H), 1.02-0.90 (m, 4H). |
| B46 | 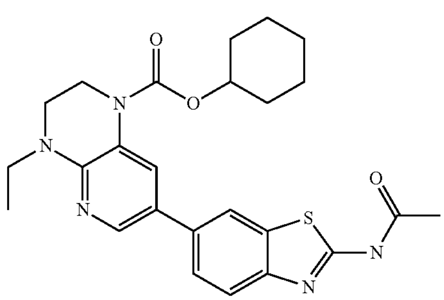 [SMILES: CCN1CCN(C(=O)OC2CCCCC2)c2cc(-c3ccc4nc(NC(C)=O)sc4c3)cnc21] | F, G | ¹H NMR (400 MHz, DMSO-d$_6$) δ 12.35 (br s, 1H), 8.21 (s, 1H), 8.13 (s, 1H), 8.05 (br s, 1H), 7.76 (d, J = 8.4 Hz, 1H), 7.60 (d, J = 8.8 Hz, 1H), 4.79-4.69 (m, 1H), 3.85-3.74 (m, 2H), 3.70-3.60 (m, 2H), 3.59-3.48 (m, 2H), 2.20 (s, 3H), 1.90-1.77 (m, 2H), 1.70-1.59 (m, 2H), 1.56-1.26 (m, 6H), 1.11 (t, J = 7.2 Hz, 3H). |

TABLE 1-continued

Selected compounds synthesized by Methods A-O

| Compd. | Structure | Method | ¹H NMR |
|---|---|---|---|
| B47 | 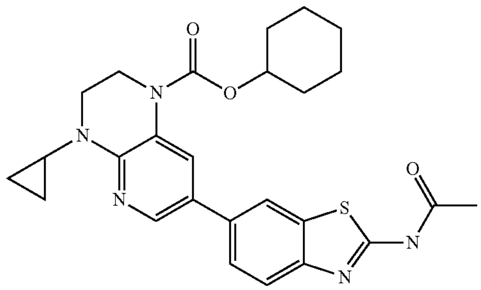 [SMILES: CC(=O)Nc1nc2ccc(-c3cnc4c(c3)N(C(=O)OC3CCCCC3)CCN4C3CC3)cc2s1] | F | ¹H NMR (400 MHz, DMSO-d$_6$) δ 12.37 (br s, 1H), 8.27 (s, 1H), 8.15 (s, 2H), 7.77 (d, J = 8.4 Hz, 1H), 7.62 (d, J = 8.4 Hz, 1H), 4.82-4.66 (m, 1H), 3.89-3.50 (m, 4H), 2.80-2.70 (m, 1H), 2.21 (s, 3H), 1.90-1.76 (m, 2H), 1.73-1.58 (m, 2H), 1.58-1.30 (m, 6H), 0.86-0.72 (m, 2H), 0.71-0.57 (m, 2H). |
| B48 | 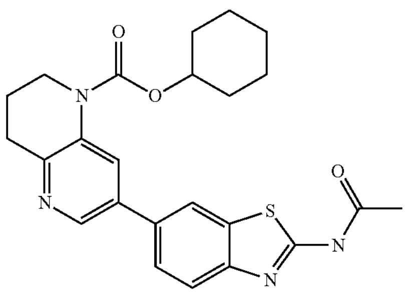 [SMILES: CC(=O)Nc1nc2ccc(-c3cnc4c(c3)N(C(=O)OC3CCCCC3)CCC4)cc2s1] | H | ¹H NMR (400 MHz, DMSO-d$_6$) δ 12.43 (s, 1H), 8.54 (s, 1H), 8.40 (s, 1H), 8.28 (s, 1H), 7.82 (d, J = 8.4 Hz, 1H), 7.69 (d, J = 8.4 Hz, 1H), 4.82-4.70 (m, 1H), 3.77 (t, J = 5.6 Hz, 2H), 2.92 (t, J = 6.0 Hz, 2H), 2.21 (s, 3H), 2.02-1.92 (m, 2H), 1.90-1.79 (m, 2H), 1.71-1.58 (m, 2H), 1.58-1.28 (m, 6H). |
| B49 | 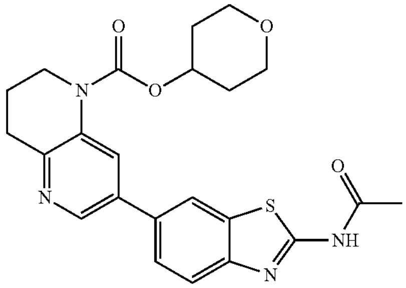 [SMILES: CC(=O)Nc1nc2ccc(-c3cnc4c(c3)N(C(=O)OC3CCOCC3)CCC4)cc2s1] | H | ¹H NMR (400 MHz, DMSO-d$_6$) δ 12.43 (br s, 1H), 8.55 (s, 1H), 8.41 (s, 1H), 8.29 (s, 1H), 7.83 (d, J = 8.4 Hz, 1H), 7.69 (d, J = 8.0 Hz, 1H), 4.99-4.87 (m, 1H), 3.90-3.67 (m, 4H), 3.56-3.45 (m, 2H), 2.93 (t, J = 6.0 Hz, 2H), 2.21 (s, 3H), 2.04-1.88 (m, 4H) 1.55 (m, 2H). |
| B50 | 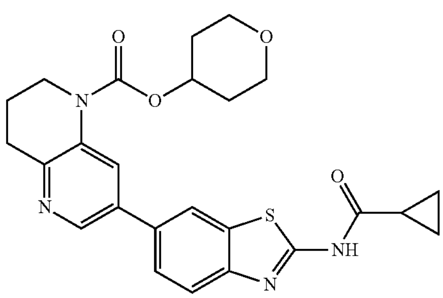 [SMILES: O=C(Nc1nc2ccc(-c3cnc4c(c3)N(C(=O)OC3CCOCC3)CCC4)cc2s1)C1CC1] | H, I | ¹H NMR (400 MHz, DMSO-d$_6$) δ 12.84 (s, 1H), 8.96-8.78 (m, 2H), 8.18 (d, J = 8.4 Hz, 1H), 8.08 (d, J = 8.4 Hz, 1H), 4.98 (s, 1H), 3.88-3.74 (m, 4H), 3.57-3.47 (m, 2H), 2.99-2.90 (m, 2H), 2.08-1.86 (m, 5H), 1.73-1.59 (m, 2H), 1.03-0.93 (m, 4H). |
| B51 | 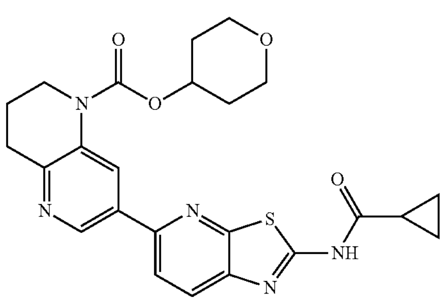 [SMILES: O=C(Nc1nc2ccc(-c3cnc4c(c3)N(C(=O)OC3CCOCC3)CCC4)nc2s1)C1CC1] | H, I | ¹H NMR (400 MHz, DMSO-d$_6$) δ 12.84 (s, 1H), 8.88-8.76 (m, 2H), 8.18 (d, J = 8.4 Hz, 1H), 8.08 (d, J = 8.4 Hz, 1H), 4.99 (s, 1H), 3.88-3.73 (m, 4H), 3.60-3.45 (m, 2H), 2.95 (t, J = 6.2 Hz, 2H), 2.09-1.86 (m, 5H), 1.73-1.54 (m, 2H), 1.07-0.91 (m, 4H) |

TABLE 1-continued

Selected compounds synthesized by Methods A-O

| Compd. | Structure | Method | ¹H NMR |
|---|---|---|---|
| B52 | 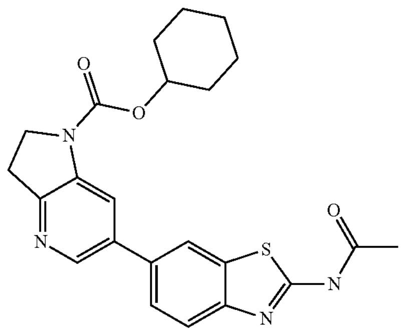 [SMILES: CC(=O)Nc1nc2ccc(-c3cnc4c(c3)N(C(=O)OC3CCCCC3)CC4)cc2s1] | H, J, K | ¹H NMR (400 MHz, DMSO-d$_6$) δ 12.42 (s, 1H), 8.40 (s, 1H), 8.27 (s, 1H), 8.18 (s, 1H), 7.83 (d, J = 8.0 Hz, 1H), 7.67 (d, J = 8.0 Hz, 1H), 4.78 (s, 1H), 4.13-3.98 (m, 2H), 3.22 (t, J = 8.6 Hz, 2H), 2.22 (s, 3H), 1.92-1.79 (m, 2H), 1.77-1.63 (m, 2H), 1.62-1.26 (m, 6H). |
| B53 | 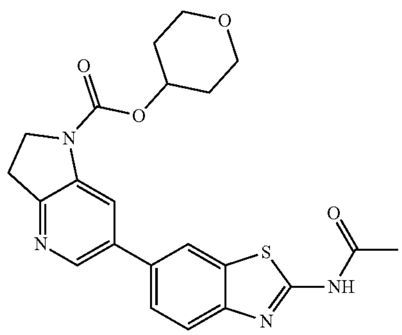 [SMILES: CC(=O)Nc1nc2ccc(-c3cnc4c(c3)N(C(=O)OC3CCOCC3)CC4)cc2s1] | H, J, K | ¹H NMR (400 MHz, DMSO-d$_6$) δ 12.42 (s, 1H), 8.42 (s, 1H), 8.28 (s, 1H), 8.19 (s, 1H), 7.83 (d, J = 8.4 Hz, 1H), 7.68 (d, J = 8.0 Hz, 1H), 4.96 (s, 1H), 4.18-4.00 (m, 2H), 3.88-3.78 (m, 2H), 3.60-3.50 (m, 2H), 3.27-3.18 (m, 2H), 2.22 (s, 3H), 2.02-1.88 (m, 2H), 1.74-1.56 (m, 2H). |
| B54 | 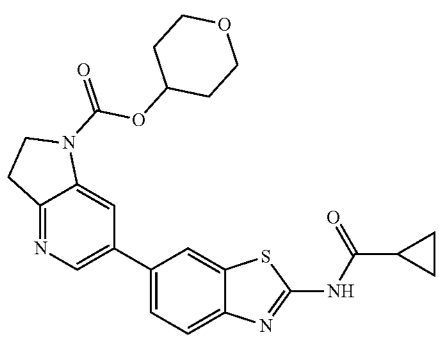 [SMILES: O=C(Nc1nc2ccc(-c3cnc4c(c3)N(C(=O)OC3CCOCC3)CC4)cc2s1)C1CC1] | H, J, K | ¹H NMR (400 MHz, DMSO-d$_6$) δ 12.72 (s, 1H), 8.41 (s, 1H), 8.28 (s, 1H), 8.22-8.06 (m, 1H), 7.83 (d, J = 8.0 Hz, 1H), 7.67 (d, J = 8.0 Hz, 1H), 4.96 (s, 1H), 4.08 (s, 2H), 3.88-3.78 (m, 2H), 3.57-3.49 (m, 2H), 3.26-3.19 (m, 2H), 2.15-1.82 (m, 4H), 1.66 (s, 2H), 0.96 (s, 4H). |
| B55 | 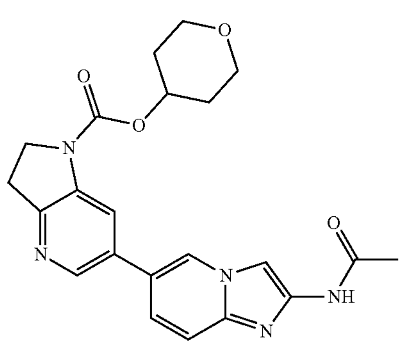 [SMILES: CC(=O)Nc1cn2cc(-c3cnc4c(c3)N(C(=O)OC3CCOCC3)CC4)ccc2n1] | H, J | ¹H NMR (400 MHz, DMSO-d$_6$) δ 10.75 (s, 1H), 8.93 (s, 1H), 8.38 (s, 1H), 8.16 (s, 2H), 7.60-7.30 (m, 2H), 4.95 (s, 1H), 4.07 (s, 2H), 3.83 (s, 2H), 3.51 (s, 2H), 3.20-3.05 (m, 2H), 2.08 (s, 3H), 2.00-1.87 (m, 2H), 1.75-1.55 (m, 2H). |

TABLE 1-continued

Selected compounds synthesized by Methods A-O

| Compd. | Structure | Method | ¹H NMR |
|---|---|---|---|
| B56 | 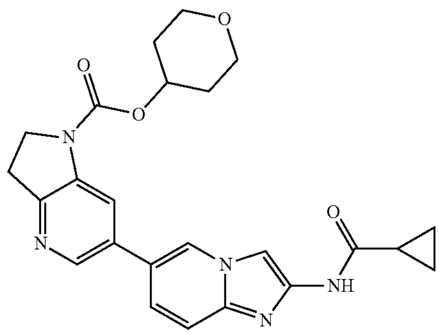 [SMILES: O=C(Nc1cn2cc(-c3cnc4c(c3)N(C(=O)OC3CCOCC3)CC4)ccc2n1)C1CC1] | H, J | ¹H NMR (400 MHz, DMSO-d$_6$) δ 11.01 (s, 1H), 8.92 (s, 1H), 8.38 (s, 1H), 8.11 (s, 2H), 7.60-7.40 (m, 2H), 4.95 (s, 1H), 4.08 (s, 2H), 3.90-3.75 (m, 2H), 3.60-3.45 (m, 2H), 3.25-3.15 (m, 2H), 1.95 (s, 3H), 1.66 (s, 2H), 0.82 (s, 4H). |
| B57 | 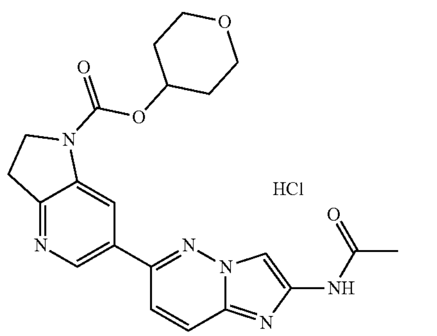 [SMILES: CC(=O)Nc1cn2nc(-c3cnc4c(c3)N(C(=O)OC3CCOCC3)CC4)ccc2n1 ; Cl] | H, J | ¹H NMR (400 MHz, DMSO-d$_6$) δ 10.96 (s, 1H), 8.75 (s, 1H), 8.60-8.40 (m, 1H), 8.29 (s, 1H), 8.15-8.05 (m, 1H), 7.90-7.70 (m, 1H), 5.15-4.85 (m, 1H), 4.11 (s, 2H), 3.83 (s, 2H), 3.75-3.65 (m, 2H), 3.35-3.25 (m, 2H), 2.11 (s, 3H), 1.98 (s, 2H), 1.67 (s, 2H). |
| B58 | 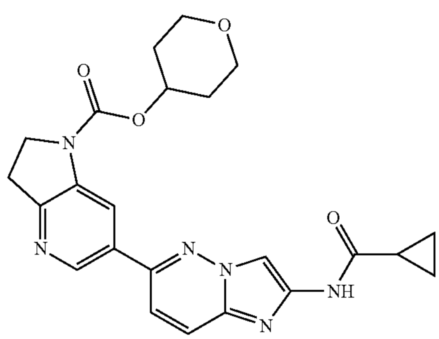 [SMILES: O=C(Nc1cn2nc(-c3cnc4c(c3)N(C(=O)OC3CCOCC3)CC4)ccc2n1)C1CC1] | H, J | ¹H NMR (400 MHz, DMSO-d$_6$) δ 11.22 (s, 1H), 8.72 (s, 1H), 8.55-8.40 (m, 1H), 8.26 (s, 1H), 8.07 (d, J = 9.2 Hz, 1H), 7.80 (s, 1H), 5.20-4.80 (m, 1H), 4.08 (s, 2H), 3.95-3.85 (m, 2H), 3.75-3.50 (m, 2H), 3.28-3.20 (m, 2H), 2.05-1.85 (m, 3H), 1.78-1.66 (m, 2H), 0.87-0.79 (m, 4H). |
| B59 | 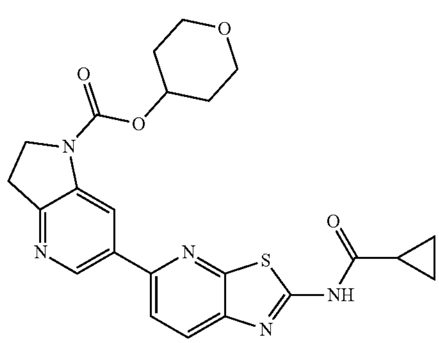 [SMILES: O=C(Nc1nc2ccc(-c3cnc4c(c3)N(C(=O)OC3CCOCC3)CC4)nc2s1)C1CC1] | H, J | ¹H NMR (400 MHz, DMSO-d$_6$) δ 12.88 (s, 1H), 8.82 (s, 1H), 8.70-8.58 (m, 1H), 8.18 (d, J = 8.4 Hz, 1H), 8.15-8.06 (m, 1H), 5.20-4.90 (m, 1H), 4.18-4.00 (m, 2H), 3.95-3.80 (m, 2H), 3.65-3.60 (m, 2H), 3.31-3.24 (m, 2H), 2.10-1.90 (m, 4H), 1.75 (s, 1H), 0.99 (s, 4H). |

TABLE 1-continued

Selected compounds synthesized by Methods A-O

| Compd. | Structure | Method | ¹H NMR |
|---|---|---|---|
| B60 | 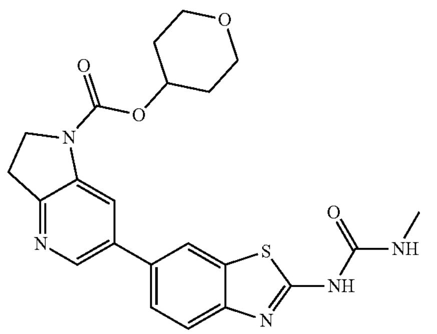 [SMILES: CNC(=O)Nc1nc2ccc(-c3cnc4c(c3)N(C(=O)OC3CCOCC3)CC4)cc2s1] | H, J, K, L | ¹H NMR (400 MHz, DMSO-d$_6$) δ 10.92 (s, 1H), 8.40 (s, 1H), 8.19 (s, 2H), 7.70 (d, J = 8.0 Hz, 1H), 7.60 (d, J = 8.0 Hz, 1H), 6.68 (s, 1H), 4.96 (s, 1H), 4.25-3.95 (m, 2H), 3.92-3.75 (m, 2H), 3.60-3.45 (m, 2H), 3.22 (t, J = 8.6 Hz, 2H), 2.73 (d, J = 4.4 Hz, 3H), 2.05-1.90 (m, 2H), 1.75-1.60 (m, 2H). |
| B61 | 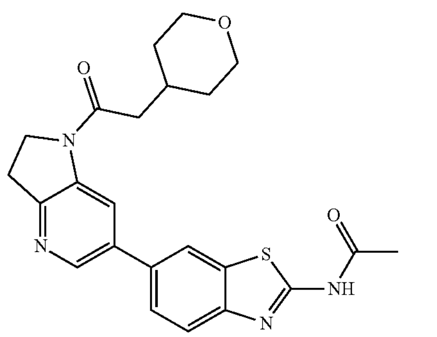 [SMILES: CC(=O)Nc1nc2ccc(-c3cnc4c(c3)N(C(=O)CC3CCOCC3)CC4)cc2s1] | H, J, K | ¹H NMR (400 MHz, DMSO-d$_6$) δ 12.41 (br s, 1H), 8.58 (s ,1H), 8.46 (s ,1H), 8.28 (s, 1H), 7.81 (d, J = 8.0 Hz, 1H), 7.80 (d, J = 8.4 Hz, 1H), 4.21 (t, J = 8.0 Hz, 2H), 3.90-2.78 (m, 2H), 3.32-3.21 (m, 4H), 2.45 (d, J = 6.4 Hz, 2H), 2.22 (s, 3H), 2.15-2.01 (m, 1H), 1.74-1.60 (m, 2H), 1.36-1.21 (m, 2H). |
| B62 | 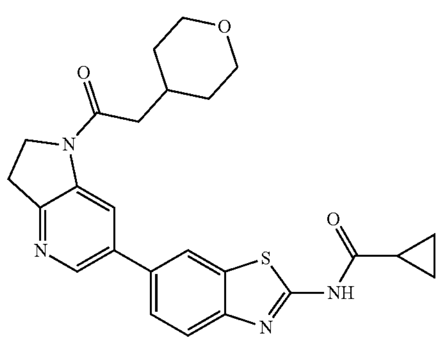 [SMILES: O=C(Nc1nc2ccc(-c3cnc4c(c3)N(C(=O)CC3CCOCC3)CC4)cc2s1)C1CC1] | H, J, K | ¹H NMR (400 MHz, DMSO-d$_6$) δ 12.72 (br s, 1H), 8.58 (s, 1H), 8.45 (s, 1H), 8.27 (s, 1H), 7.81 (d, J = 8.4 Hz, 1H), 7.68 (d, J = 8.0 Hz, 1H), 4.20 (t, J = 8.0 Hz, 2H), 3.89-3.78 (m, 2H), 3.30-3.19 (m, 4H), 2.45 (d, J = 6.4 Hz, 2H), 2.15-1.94 (m, 2H), 1.73-1.60 (m, 2H), 1.36-1.19 (m, 2H), 1.02-0.88 (m, 4H). |
| B63 | 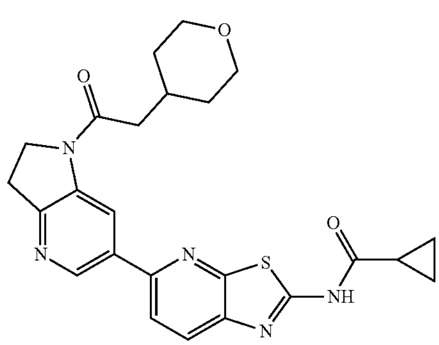 [SMILES: O=C(Nc1nc2ccc(-c3cnc4c(c3)N(C(=O)CC3CCOCC3)CC4)nc2s1)C1CC1] | H, J | ¹H NMR (400 MHz, DMSO-d$_6$) δ 12.85 (br s, 1H), 8.95 (s, 1H), 8.82 (s, 1H), 8.16 (d, J = 8.4 Hz, 1H), 8.06 (d, J = 8.4 Hz, 1H), 4.21 (t, J = 8.0 Hz, 2H), 3.89-3.77 (m, 2H), 3.31-3.22 (m, 4H), 2.47-2.43 (m, 2H), 2.14-2.00 (m, 2H), 1.74-1.62 (m, 2H), 1.36-1.20 (m, 2H), 1.05-0.94 (m, 4H). |

TABLE 1-continued

Selected compounds synthesized by Methods A-O

| Compd. | Structure | Method | ¹H NMR |
|---|---|---|---|
| B64 | 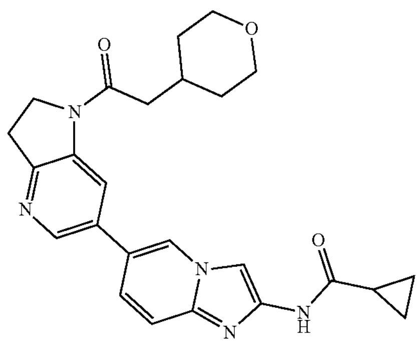 [SMILES: O=C(Nc1cn2cc(-c3cnc4c(c3)N(C(=O)CC3CCOCC3)CC4)ccc2n1)C1CC1] | H, J | ¹H NMR (400 MHz, DMSO-d$_6$) δ 11.79 (br s, 1H), 9.18 (s, 1H), 8.63 (s, 1H), 8.50 (s, 1H), 8.18 (s, 1H), 7.99-7.89 (m, 1H), 7.83-7.75 (m, 1H), 4.22 (t, J = 8.4 Hz, 2H), 3.93-3.82 (m, 2H), 3.38-3.25 (m, 4H), 2.47-2.39 (m, 2H), 2.13-1.91 (m, 2H), 1.72-1.61 (m, 2H), 1.38-1.18 (m, 2H), 0.90 (s, 4H). |
| B65 | 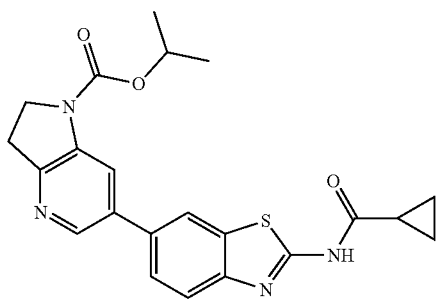 [SMILES: CC(C)OC(=O)N1CCc2ncc(-c3ccc4nc(NC(=O)C5CC5)sc4c3)cc21] | H, J, K | ¹H NMR (400 MHz, DMSO-d$_6$) δ 12.71 (s, 1H), 8.41 (s, 1H), 8.28 (s, 2H), 8.18 (s, 1H), 7.82 (d, J = 8.4 Hz, 1H), 7.68 (d, J = 8.0 Hz, 1H), 5.05-4.85 (m, 1H), 4.03 (t, J = 8.2 Hz, 2H), 3.21 (t, J = 8.4 Hz, 2H), 2.08-1.98 (m, 1H), 1.32 (s, 6H), 1.00-0.95 (m, 4H). |
| B66 | 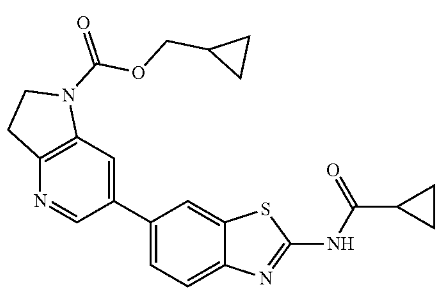 [SMILES: O=C(Nc1nc2ccc(-c3cnc4c(c3)N(C(=O)OCC3CC3)CC4)cc2s1)C1CC1] | H, J, K | ¹H NMR (400 MHz, CDCl$_3$) δ 11.44 (s, 1H), 8.40 (s, 1H), 8.33 (s, 1H), 8.04 (s, 1H), 7.83 (d, J = 7.6 Hz, 1H), 7.67 (d, J = 8.0 Hz, 1H), 4.21-4.04 (m, 4H), 3.32 (t, J = 8.6 Hz, 2H), 1.79-1.70 (m, 1H), 1.63 (s, 2H), 1.33 (s, 1H), 1.10-0.98 (m, 2H), 0.70-0.58 (m, 2H), 0.48-0.30 (m, 2H). |
| B67 | 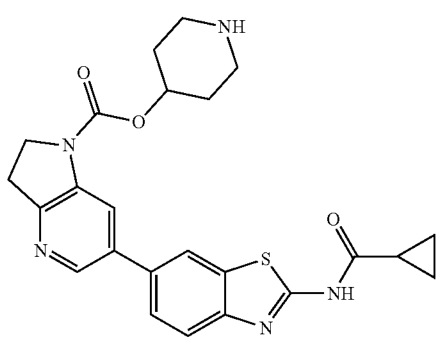 [SMILES: O=C(Nc1nc2ccc(-c3cnc4c(c3)N(C(=O)OC3CCNCC3)CC4)cc2s1)C1CC1] | H, J, K, M | ¹H NMR (400 MHz, DMSO-d$_6$) δ 8.43 (s, 1H), 8.28 (s, 1H), 8.17 (br s, 1H), 7.82 (d, J = 7.6 Hz, 1H), 7.68 (d, J = 8.0 Hz, 1H), 5.09-4.94 (m, 1H), 4.26-3.94 (m, 2H), 3.29-2.96 (m, 6H), 2.21-1.78 (m, 5H), 0.96 (s, 4H). |

TABLE 1-continued

Selected compounds synthesized by Methods A-O

| Compd. | Structure | Method | ¹H NMR |
|---|---|---|---|
| B68 | 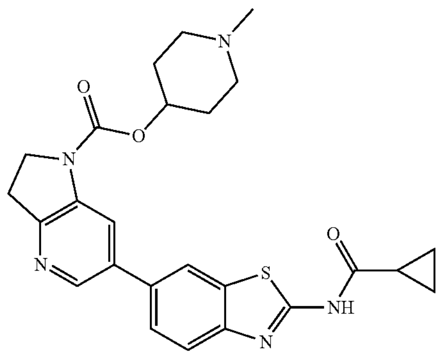 [SMILES: CN1CCC(OC(=O)N2CCc3ncc(-c4ccc5nc(NC(=O)C6CC6)sc5c4)cc32)CC1] | H, J, K, M | ¹H NMR (400 MHz, CDCl$_3$) δ 11.33 (br s, 1H), 8.43 (s, 1H), 8.31 (s, 1H), 8.04 (s, 1H), 7.82 (d, J = 8.0 Hz, 1H), 7.66 (d, J = 8.0 Hz, 1H), 5.18-4.95 (m, 1H), 4.14 (t, J = 8.0 Hz, 2H), 3.33 (t, J = 8.0 Hz, 2H), 3.10-2.66 (m, 4H), 2.58 (s, 3H), 2.38-2.18 (m, 2H), 2.15-2.04 (m, 2H), 1.84-1.71 (m, 1H), 1.32-1.27 (m, 2H), 1.09-0.95 (m, 2H). |
| B69 | 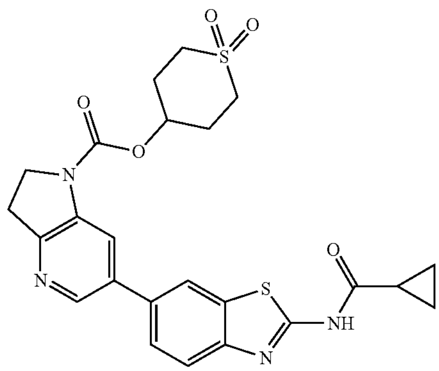 [SMILES: O=C(Nc1nc2ccc(-c3cnc4c(c3)N(C(=O)OC3CCS(=O)(=O)CC3)CC4)cc2s1)C1CC1] | H, J, N | ¹H NMR (400 MHz, DMSO-d$_6$) δ 12.73 (br s, 1H), 8.43 (s, 1H), 8.28 (s, 1H), 8.18 (br s, 1H), 7.82 (d, J = 8.4 Hz, 1H), 7.68 (d, J = 8.4 Hz, 1H), 5.22-4.98 (m, 1H), 4.26-3.97 (m, 2H), 3.31-3.12 (m, 6H), 2.38-2.18 (m, 4H), 2.07-1.95 (m, 1H), 1.09-0.88 (m, 4H). |
| B70 | 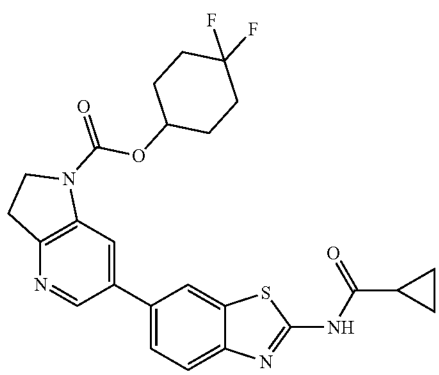 [SMILES: O=C(Nc1nc2ccc(-c3cnc4c(c3)N(C(=O)OC3CCC(F)(F)CC3)CC4)cc2s1)C1CC1] | H, J, K | ¹H NMR (400 MHz, DMSO-d$_6$) δ 12.73 (s, 1H), 8.42 (s, 1H), 8.28 (s, 1H), 8.18 (s, 1H), 7.82 (d, J = 8.4 Hz, 1H), 7.68 (d, J = 8.0 Hz, 1H), 4.97 (s, 1H), 4.18-4.03 (m, 2H), 3.22 (t, J = 8.6 Hz, 2H), 2.18-1.80 (m, 11H), 1.00-0.93 (m, 4H). |
| B71 | 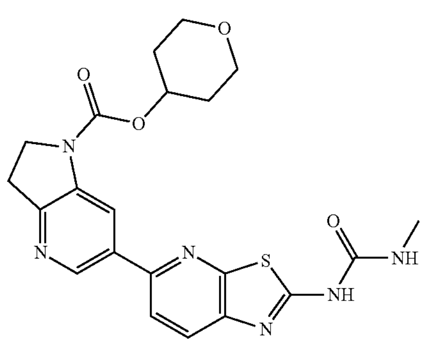 [SMILES: CNC(=O)Nc1nc2ccc(-c3cnc4c(c3)N(C(=O)OC3CCOCC3)CC4)nc2s1] | H, J | ¹H NMR (400 MHz, DMSO-d$_6$) δ 11.13 (br s, 1H), 8.77 (s, 1H), 8.58 (s, 1H), 8.08-7.95 (m, 2H), 6.80 (br s, 1H), 5.19-4.88 (m, 1H), 4.18-3.83 (m, 4H), 3.74-3.45 (m, 2H), 3.24 (t, J = 8.4 Hz, 2H), 2.74 (d, J = 4.4 Hz, 3H), 2.09-1.91 (m, 2H), 1.82-1.56 (m, 2H). |

TABLE 1-continued

Selected compounds synthesized by Methods A-O

| Compd. | Structure | Method | ¹H NMR |
|---|---|---|---|
| B72 | 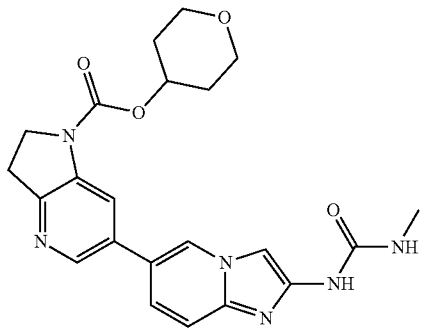 [SMILES: CNC(=O)Nc1cn2cc(-c3cnc4c(c3)N(C(=O)OC3CCOCC3)CC4)ccc2n1] | H, J | ¹H NMR (400 MHz, DMSO-d$_6$) δ 9.02 (s, 1H), 8.88 (s, 1H), 8.37 (s, 1H), 8.13 (s, 1H), 7.83 (s, 1H), 7.52-7.39 (m, 2H), 6.56 (br s, 1H), 5.06-4.86 (m, 1H), 4.19-3.94 (m, 2H), 3.90-3.75 (m, 2H), 3.53 (t, J = 8.8 Hz, 2H), 3.22 (t, J = 8.4 Hz, 2H), 2.68 (d, J = 4.4 Hz, 3H), 2.06-1.88 (m, 2H), 1.80-1.55 (m, 2H). |
| B73 | 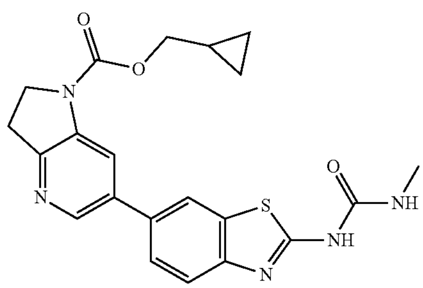 [SMILES: CNC(=O)Nc1nc2ccc(-c3cnc4c(c3)N(C(=O)OCC3CC3)CC4)cc2s1] | H, J | ¹H NMR (400 MHz, DMSO-d$_6$) δ 10.93 (s, 1H), 8.42 (s, 1H), 8.20 (s, 2H), 7.78-7.66 (m, 1H), 7.65-7.58 (m, 1H), 6.69 (s, 1H), 4.06 (s, 4H), 3.24 (s, 2H), 2.80-2.66 (m, 3H), 1.32-1.10 (m, 1H), 0.66-0.50 (m, 2H), 0.37 (s, 2H). |
| B74 | 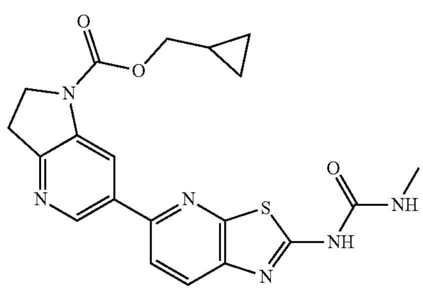 [SMILES: CNC(=O)Nc1nc2ccc(-c3cnc4c(c3)N(C(=O)OCC3CC3)CC4)nc2s1] | H, J | ¹H NMR (400 MHz, DMSO-d$_6$) δ 11.13 (br s, 1H), 8.76 (s, 1H), 8.57 (s, 1H), 8.03-7.98 (m, 2H), 6.79 (br s, 1H), 4.21-3.94 (m, 4H), 3.23 (t, J = 8.2 Hz, 2H), 2.74 (d, J = 4.4 Hz, 3H), 1.19-1.15 (m, 1H), 0.76-0.58 (m, 2H), 0.50-0.28 (m, 2H). |
| B75 | 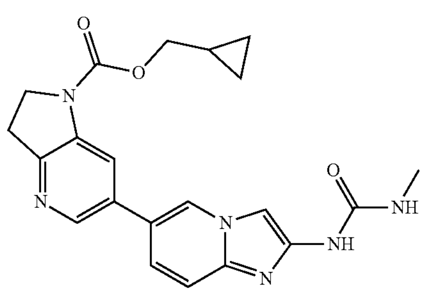 [SMILES: CNC(=O)Nc1cn2cc(-c3cnc4c(c3)N(C(=O)OCC3CC3)CC4)ccc2n1] | H, J | ¹H NMR (400 MHz, DMSO-d$_6$) δ 9.04 (s, 1H), 8.89 (s, 1H), 8.42-8.32 (m, 1H), 8.12 (s, 1H), 7.82 (s, 1H), 7.57-7.36 (m, 2H), 6.56 (s, 1H), 4.05 (s, 4H), 3.22 (t, J = 8.6 Hz, 2H), 2.68 (d, J = 4.4 Hz, 2H), 1.22 (s, 1H), 0.65-0.48 (m, 2H), 0.36 (s, 2H). |
| B76 | 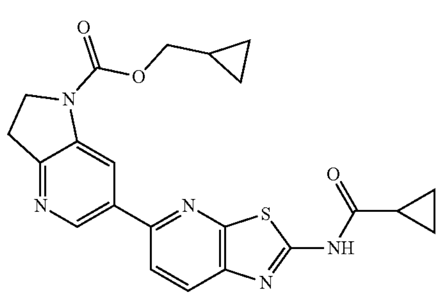 [SMILES: O=C(Nc1nc2ccc(-c3cnc4c(c3)N(C(=O)OCC3CC3)CC4)nc2s1)C1CC1] | H, J | ¹H NMR (400 MHz, DMSO-d$_6$) δ 12.85 (br s, 1H), 8.79 (s, 1H), 8.59 (br s, 1H), 8.16 (d, J = 8.8 Hz, 1H), 8.07 (d, J = 8.4 Hz, 1H), 4.22-3.95 (m, 4H), 3.24 (t, J = 8.4 Hz, 2H), 2.10-1.97 (m, 1H), 1.32-1.18 (m, 1H), 1.07-0.91 (m, 4H), 0.74-0.50 (m, 2H), 0.50-0.25 (m, 2H). |

TABLE 1-continued

Selected compounds synthesized by Methods A-O

| Compd. | Structure | Method | ¹H NMR |
|---|---|---|---|
| B77 | 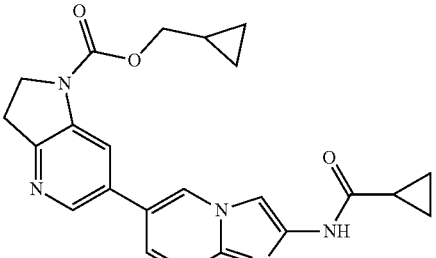 | H, J | ¹H NMR (400 MHz, DMSO-$d_6$) δ 11.01 (s, 1H), 8.92 (s, 1H), 8.38 (s, 1H), 8.22-8.05 (m, 2H), 7.59-7.45 (m, 2H), 4.17-4.00 (m, 4H), 3.23 (t, J = 8.0 Hz, 2H), 1.99-1.88 (m, 1H), 1.30-1.17 (m, 1H), 0.98-0.72 (m, 4H), 0.64-0.51 (m, 2H), 0.47-0.27 (m, 2H). |
| B78 | 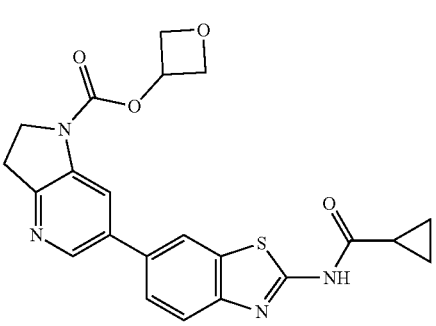 [SMILES: O=C(Nc1nc2ccc(-c3cnc4c(c3)N(C(=O)OC3COC3)CC4)cc2s1)C1CC1] | H, J, K | ¹H NMR (400 MHz, DMSO-$d_6$) δ 12.72 (s, 1H), 8.50-8.40 (m, 1H), 8.29 (s, 1H), 8.14 (s, 1H), 7.82 (d, J = 8.4 Hz, 1H), 7.68 (d, J = 8.4 Hz, 1H), 5.49 (s, 1H), 4.85 (t, J = 7.0 Hz, 2H), 4.62 (s, 2H), 4.25-4.05 (m, 2H), 3.24 (t, J = 8.8 Hz, 4H), 2.06-1.94 (m, 1 H), 1.02-0.88 (m, 4H). |
| B79 | 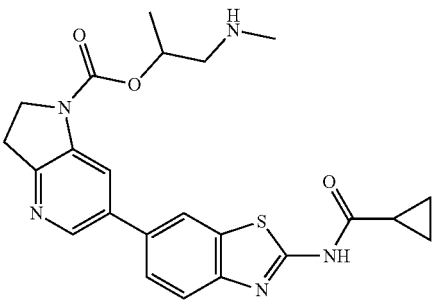 [SMILES: CNCC(C)OC(=O)N1CCc2ncc(-c3ccc4nc(NC(=O)C5CC5)sc4c3)cc21] | H, J, K, M | ¹H NMR (400 MHz, DMSO-$d_6$) δ 12.77 (br s, 1H), 8.87 (br s, 1H), 8.44 (s, 1H), 8.29 (s, 1H), 8.19 (s, 1H), 7.83 (d, J = 8.4 Hz, 1H), 7.75-7.62 (m, 1H), 5.38-5.02 (m, 1H), 4.41-4.22 (m, 1H), 4.15-3.95 (m, 1H), 3.25-3.15 (m, 4H), 2.58 (s, 3H), 2.10-1.97 (m, 1H), 1.43-1.28 (m, 3H), 1.02-0.90 (m, 4H). |
| B80 | 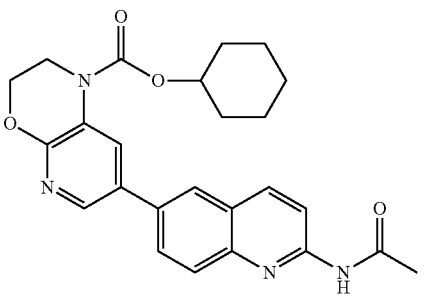 [SMILES: CC(=O)Nc1ccc2cc(-c3cnc4c(c3)N(C(=O)OC3CCCCC3)CCO4)ccc2n1] | O | ¹H NMR (400 MHz, DMSO-$d_6$) δ 10.86 (s, 1H), 8.70 (s, 1H), 8.43-8.36 (m, 1H), 8.35-8.28 (m, 2H), 8.13 (s, 1H), 7.96 (d, J = 8.4 Hz, 1H), 7.87 (d, J = 8.4 Hz, 1H), 8.87-8.69 (m, 1H), 4.42 (s, 2H), 3.93 (s, 2H), 2.16 (s, 3H), 1.95-1.82 (m, 2H), 1.77-1.61 (m, 2H), 1.61-1.26 (m, 6H). |

Biological Activities

The efficacies of Compounds B1-B80 were tested for their inhibition activities in necroptosis assays as follows:

Example 19: Biological In Vitro HT29 Cell Assay of Compound B3

Human colon cancer HT29 cells were used in a necroptosis assay. For this assay, HT29 cells were added to 96-well plates and then were pre-treated with 10 μM of the test compound for one hour. Then the cells were treated with TNF-α (40 ng/mL), Smacmimetic (100 nM) and z-VAD (20 μM) for 48 hours, and the viability of cells was quantified. DMSO pretreatment group was used as negative controls, Nec-1 pretreatment group was used as positive controls. The compounds B3 was taken as an example, and the results are shown in FIG. 1. As shown in FIG. 1, the $IC_{50}$ of Compound B3 in the in Vitro HT29 Cell Assay is 0.5 nM.

Example 20: Biological In Vitro L929 Cell Assay of Compound B3

Figure 2:
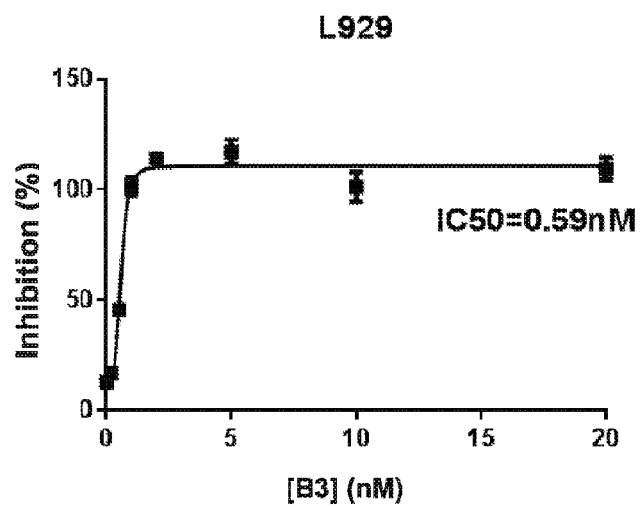
FIG. 2 depicts the inhibition of TNF-α induced-necrosis in L929 cells by compound B3 in Example 20.

Mouse L929 mouse skin fibroblast cells were added to 96-well plates and then were pre-treated with 10 μM of the test compound for one hour. Then the cells were treated with TNF-α (40 ng/mL) and z-VAD (20 μM) for 48 hours, and the viability of cells was quantified by detecting adenosine triphosphate (ATP) levels. DMSO pretreatment group was used as negative controls, Nec-1 pretreatment group was used as positive controls. The compounds B3 was taken as an example, and the results are shown in FIG. 2. As shown in FIG. 2, the $IC_{50}$ of Compound B3 in the in Vitro HT29 Cell Assay is 0.59 nM

TABLE 2

Biological activities of selected compounds

| Compd. Number | HT29 Inhibition % | HT29 $IC_{50}$ (nM) | L929 Inhibition % | L929 $IC_{50}$ (nM) |
|---|---|---|---|---|
| B1 | ND | 11 | ND | 3.6 |
| B2 | ND | 2 | ND | ND |
| B3 | ND | 0.5 | ND | 0.59 |
| B4 | ND | 90 | ND | ND |
| B5 | ND | 42 | ND | ND |
| B6 | ND | 90 | ND | ND |
| B7 | ND | 46 | ND | 20 |
| B8 | ND | 1.0 | ND | 1.5 |
| B9 | ND | 0.5 | ND | 0.2 |
| B10 | ND | 5 | ND | ND |
| B11 | ND | 500 | ND | 8.9 |
| B12 | ND | 11 | ND | ND |
| B13 | ND | 1.3 | ND | 0.7 |
| B14 | 30% (50 nM) | ND | ND | 12.6 |
| B15 | ND | 20 | ND | 8.8 |
| B16 | ND | 4 | ND | 1.5 |
| B17 | ND | 26 | ND | ND |
| B18 | 10% (50 nM) | ND | ND | ND |
| B19 | ND | 20 | ND | 10 |
| B20 | 20% (50 nM) | ND | ND | ND |
| B21 | ND | 50 | ND | 31 |
| B22 | 25% (50 nM) | 114 | ND | 80 |
| B23 | 10% (50 nM) | 147 | ND | 11.5 |
| B24 | ND | 18 | ND | 5 |
| B25 | ND | 17 | ND | 10 |
| B26 | ND | 3.2 | ND | ND |
| B27 | ND | 132 | ND | ND |
| B28 | ND | 39 | ND | ND |
| B29 | ND | 27 | ND | ND |
| B30 | ND | 186 | ND | ND |
| B31 | ND | 8.5 | ND | ND |
| B32 | ND | 0.9 | ND | ND |
| B33 | ND | 15 | ND | ND |
| B34 | ND | 2300 | ND | ND |
| B35 | ND | 36 | ND | 1.0 |
| B36 | ND | 530 | ND | ND |
| B37 | ND | 32 | ND | 30 |
| B38 | ND | 3500 | ND | 15 |
| B39 | ND | 2700 | ND | ND |
| B40 | ND | 24 | ND | ND |
| B41 | ND | 110 | ND | ND |
| B42 | ND | 38 | ND | ND |
| B43 | ND | 13 | ND | ND |
| B44 | ND | 95 | ND | ND |
| B45 | ND | 18 | ND | ND |
| B46 | ND | 70 | ND | ND |
| B47 | ND | 157 | ND | ND |
| B48 | ND | 2.4 | ND | ND |
| B49 | ND | 11.4 | ND | ND |
| B50 | ND | 1.5 | ND | ND |
| B51 | ND | 7.2 | ND | ND |
| B52 | ND | 5 | ND | ND |
| B53 | ND | 4.7 | ND | ND |
| B54 | ND | 2 | ND | ND |
| B55 | ND | 49 | ND | ND |
| B56 | ND | 4.6 | ND | ND |
| B57 | ND | 600 | ND | 90 |
| B58 | ND | 17 | ND | ND |
| B59 | ND | 7.0 | ND | ND |
| B60 | ND | 1.3 | ND | 2.8 |
| B61 | ND | 39 | ND | ND |
| B62 | ND | 1.9 | ND | ND |
| B63 | ND | 25 | ND | 8.5 |
| B64 | ND | 53 | ND | ND |
| B65 | ND | 3.2 | ND | 4.5 |
| B66 | ND | 0.39 | ND | 0.73 |
| B67 | ND | 300 | ND | ND |
| B68 | ND | 30 | ND | 28.3 |
| B69 | ND | 4.8 | ND | 15 |
| B70 | ND | 1.2 | ND | 1.3 |
| B71 | ND | 33.4 | ND | ND |
| B72 | ND | 48.1 | ND | ND |
| B73 | ND | 1.8 | ND | ND |
| B74 | ND | 23 | ND | ND |
| B75 | ND | 19 | ND | ND |
| B76 | ND | 2.4 | ND | ND |
| B77 | ND | 1.7 | ND | ND |
| B78 | ND | 6.7 | ND | ND |
| B79 | ND | 16 | ND | ND |
| B80 | ND | 1000 | ND | ND |

In Table 2, (1) "ND" indicates "not detected;" (2) Explanation for inhibition %: Taking Compound B14 as an example, its inhibition % was 30% (50 nM). It means that the when Compound B14 at a concentration of 50 nM was used in the HT29 Cell Assay, the necrosis of cells were inhibited at 30%.

As shown in FIGS. 1 and 2 and Table 2, the heteroaryl compounds of the present disclosure can be effective inhibitors for necrosis, and can be used in treating or preventing diseases caused by or associate with activated necrotic pathways.

What is claimed is:

1. A compound of Formula I:

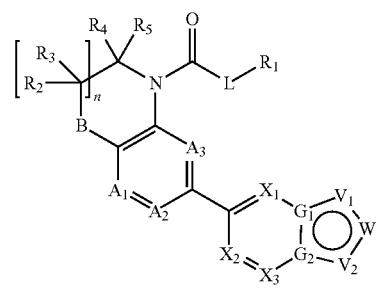

or a pharmaceutically acceptable salt, hydrate, solvate, stereoisomer or a tautomer thereof, wherein n is 0, 1 or 2;

$A_1$, $A_2$ and $A_3$ are independently N or $CR_6$;

B is O, S, S=O, S(=O)$_2$, $NR_7$ or $CR_7R_8$;

$X_1$, $X_2$ and $X_3$ are independently N or $CR_9$;

$G_1$ and $G_2$ are independently N or C;

$V_1$ and $V_2$ are independently N, O, S, $NR_{10}$ or $CR_{10}$;

W is $V_3$, $V_4$—$V_5$, or $V_4$=$V_5$, wherein when W is $V_4$—$V_5$ or $V_4$=$V_5$, $V_4$ bonds with $V_1$, $V_5$ bonds with $V_2$;

wherein $V_4$ is N, O, S, or $CR_{11}$, wherein $V_3$ and $V_5$ is independently C—$NR_{12}R_{13}$;

L is O, S, $NR_{16}$ or $CR_{16}R_{17}$;

$R_1$ is $C_{1-6}$ alkyl, $C_{3-8}$ cycloalkyl, $C_{6-12}$ spirocycle, phenyl, 5-6 membered heteroaryl comprising 1-3 hetero atoms, 3-8 membered heterocycle comprising 1-3 hetero atoms, or 6-12 membered heterospirocycle comprising 1-3 hetero atoms, all of which are unsubstituted or substituted with 1-3 $R_{14}$, wherein each hetero atom is independently N, O or S;

each of $R_2$, $R_3$, $R_4$, $R_5$, $R_7$, and $R_8$ is independently selected from the group consisting of H, deuterium, halide, —CN, —OH, amino, $C_{1-6}$ alkyl, $C_{1-6}$ alkoxy, $C_{1-6}$ alkylamino, $C_{3-6}$ cycloalkyl, —C(=O)$C_{1-6}$ alkyl, —C(=O)O$C_{1-6}$ alkyl, phenyl, 5-6 membered heteroaryl comprising 1-3 hetero atoms, and 3-8 membered heterocycle comprising 1-3 hetero atoms, wherein each hetero atom is independently N, O or S, and wherein each of $C_{1-6}$ alkyl, $C_{1-6}$ alkoxy, $C_{1-6}$ alkyamino, $C_{3-6}$ cycloalkyl, —C(=O)$C_{1-6}$ alkyl, —C(=O)O$C_{1-6}$ alkyl, phenyl, 5-6 membered heteroaryl, and 3-8 membered heterocycle are unsubstituted or substituted with 1-3 groups independently selected from the group consisting of deuterium, halide, $C_{1-3}$ alkyl and $C_{1-3}$ alkoxy;

or $R_2$ and $R_3$ together form a carbonyl bond (=O);

or $R_2$ and $R_3$ together, with atom(s) they attached to, form $C_{3-8}$ cycloalkyl or 3-6 membered heterocycle comprising 1-2 hetero atoms, wherein each hetero atom is independently N, O or S;

or $R_4$ and $R_5$ together form a carbonyl bond (=O);

or $R_4$ and $R_5$ together, with atom(s) they attached to, form $C_{3-8}$ cycloalkyl or 3-6 membered heterocycle comprising 1-2 hetero atoms, wherein each hetero atom is independently N, O or S;

or $R_7$ and $R_8$ together form a carbonyl bond (=O);

or $R_7$ and $R_8$ together, with atom(s) they attached to, form $C_{3-8}$ cycloalkyl or 3-6 membered heterocycle comprising 1-2 hetero atoms, wherein each hetero atom is independently N, O or S;

each of $R_6$, $R_9$, and $R_{10}$ is independently selected from the group consisting of H, deuterium, halide, —CN, —OH, amino, $C_{1-6}$ alkoxy, $C_{1-6}$ alkyamino, $C_{1-6}$ alkythio, $C_{3-6}$ cycloalkyl, $C_{1-6}$ alkyl, 3-8 membered heterocycle comprising 1-3 hetero atoms, phenyl, and 5-6 membered heteroaryl comprising 1-3 hetero atoms, wherein each hetero atom is independently N, O or S, and wherein each of $C_{1-6}$ alkoxy, $C_{1-6}$ alkyamino, $C_{1-6}$ alkythio, $C_{3-6}$ cycloalkyl, $C_{1-6}$ alkyl, 3-8 membered heterocycle, phenyl, and 5-6 membered heteroaryl are unsubstituted or substituted with 1-3 groups independently selected from the group consisting of deuterium, halide, $C_{1-3}$ alkyl and $C_{1-3}$ alkoxy;

$R_{11}$ is H, deuterium, halide, —CN, —OH, $C_{1-6}$ alkoxy, $C_{1-6}$ alkylthio, $C_{1-6}$ alkyl, $C_{3-6}$ cycloalkyl or $NR_{12}R_{13}$;

$R_{12}$ is H, $C_{1-6}$ alkyl or $C_{3-6}$ cycloalkyl;

$R_{13}$ is H, C(=O)$R_{15}$, C(=O)$NR_{15}R_{18}$, C(=O)O$R_{15}$, S(=O)$_2R_{15}$, S(=O)$_2NR_{15}R_{18}$, $C_{1-6}$ alkyl, $C_{3-6}$ cycloalkyl, $C_{2-6}$ alkenyl, phenyl, 3-6 membered heterocycle comprising 1-3 hetero atoms, or 5-6 membered heteroaryl comprising 1-3 hetero atoms, wherein each of $C_{1-6}$ alkyl, $C_{3-6}$ cycloalkyl, phenyl, 3-6 membered heterocycle and 5-6 membered heteroaryl is unsubstituted or substituted with 1-3 groups independently selected from the group consisting of deuterium, halide, —CN, $C_{1-6}$ alkyl, $C_{1-6}$ alkoxy, $C_{3-6}$ cycloalkyl, and 3-6 membered heterocycle comprising 1-3 hetero atoms, each hetero atom is independently N, O or S;

$R_{14}$ is H, deuterium, halide, —OH, oxy, —CN, -amino, $C_{1-6}$ alkylamino, $C_{1-6}$ alkyl, $C_{3-6}$ cycloalkyl, or $C_{1-6}$ alkoxy, wherein each of $C_{1-6}$ alkylamino, $C_{1-6}$ alkyl, $C_{3-6}$ cycloalkyl, and $C_{1-6}$ alkoxy is unsubstituted or substituted with 1-3 groups independently selected from the group consisting of deuterium, halide, and $C_{1-3}$ alkyl;

each of $R_{15}$ and $R_{18}$ is independently selected from the group consisting of H, $C_{1-6}$ alkyl, $C_{2-6}$ alkenyl, $C_{2-6}$ alkynyl, $C_{3-6}$ cycloalkyl, phenyl, 3-6 membered heterocycle comprising 1-3 hetero atoms, and 5-6 membered heteroaryl comprising 1-3 hetero atoms, wherein each hetero atom is independently N, O or S, and wherein each of $C_{1-6}$ alkyl, $C_{2-6}$ alkenyl, $C_{2-6}$ alkynyl, $C_{3-6}$ cycloalkyl, phenyl, 3-6 membered heterocycle and 5-6 membered heteroaryl is unsubstituted or substituted with 1-3 groups independently selected from the group consisting of deuterium, halide, —CN, —OH, —$CF_3$, $C_{1-6}$ alkyl, $C_{1-6}$ alkoxy, $C_{3-6}$ cycloalkyl, and 3-6 membered heterocycle comprising 1-3 hetero atoms, each hetero atom is independently N, O or S;

or $R_{15}$ and $R_{18}$ together, with nitrogen atom they attached to, form a 4-6 membered ring;

or $R_{15}$ and $R_{10}$ together, with adjacent atoms they attached to, form a 5-6 membered ring; and $R_{16}$ and $R_{17}$ are independently H, deuterium, halide, —OH, $C_{1-3}$ alkyl or $C_{1-6}$ alkoxy.

2. The compound of claim 1, wherein $V_1$ and $V_2$ is independently O, S, $NR_{10}$ or $CR_{10}$.

3. The compound of claim 1, wherein n is 0 or 1;

B is O, $NR_7$ or $CR_7R_8$, wherein $R_7$ and $R_8$ as defined in claim 1.

4. The compound of claim 1, wherein $R_{14}$ is H, deuterium, halide, —OH, oxy, —CN, -amino, $C_{1-6}$ alkyl, $C_{3-6}$ cycloalkyl, or $C_{1-6}$ alkoxy, wherein each of $C_{1-6}$ alkyl, $C_{3-6}$ cycloalkyl, and $C_{1-6}$ alkoxy is unsubstituted or substituted with 1-3 groups independently selected from the group consisting of deuterium, halide, and $C_{1-3}$ alkyl.

5. The compound of claim 1, wherein subgroup

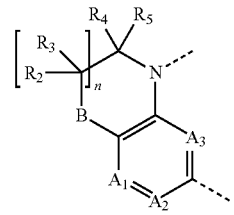

is selected from the group consisting of:

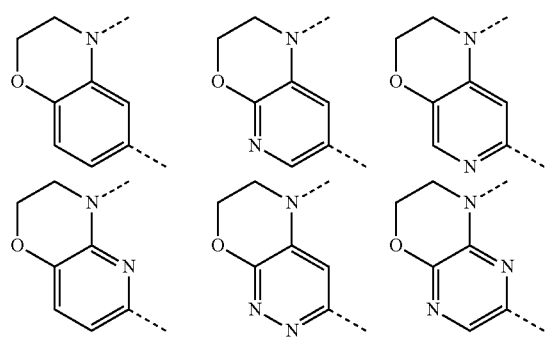

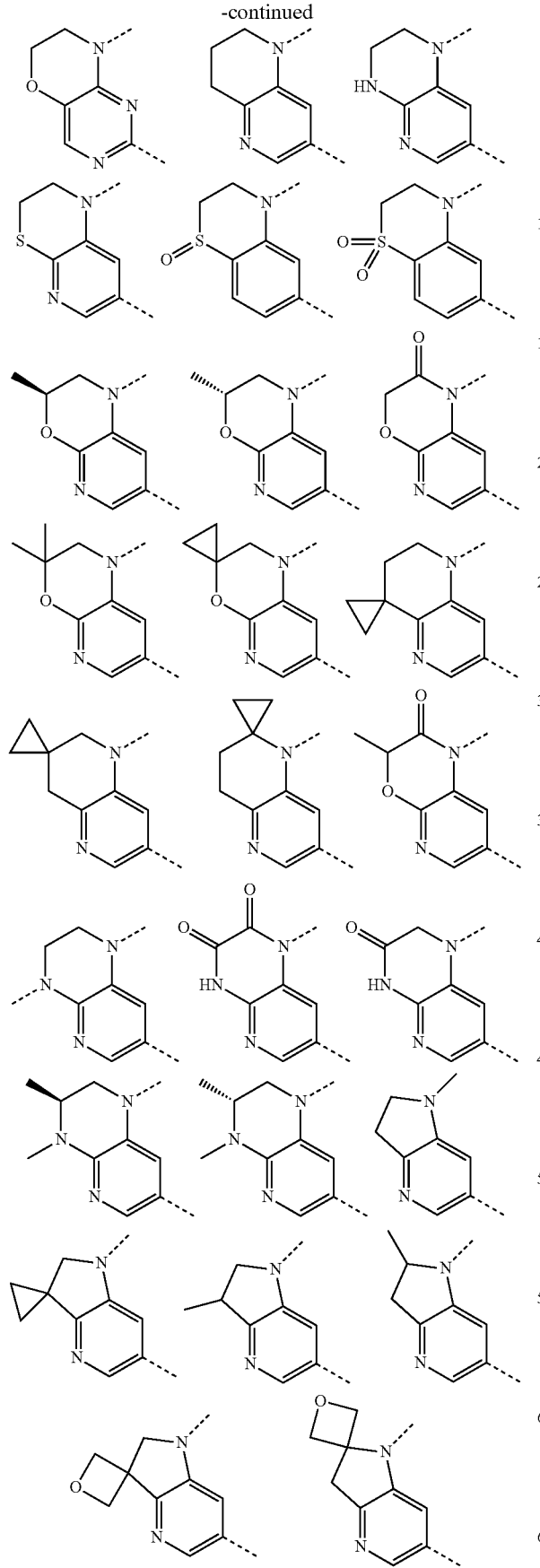
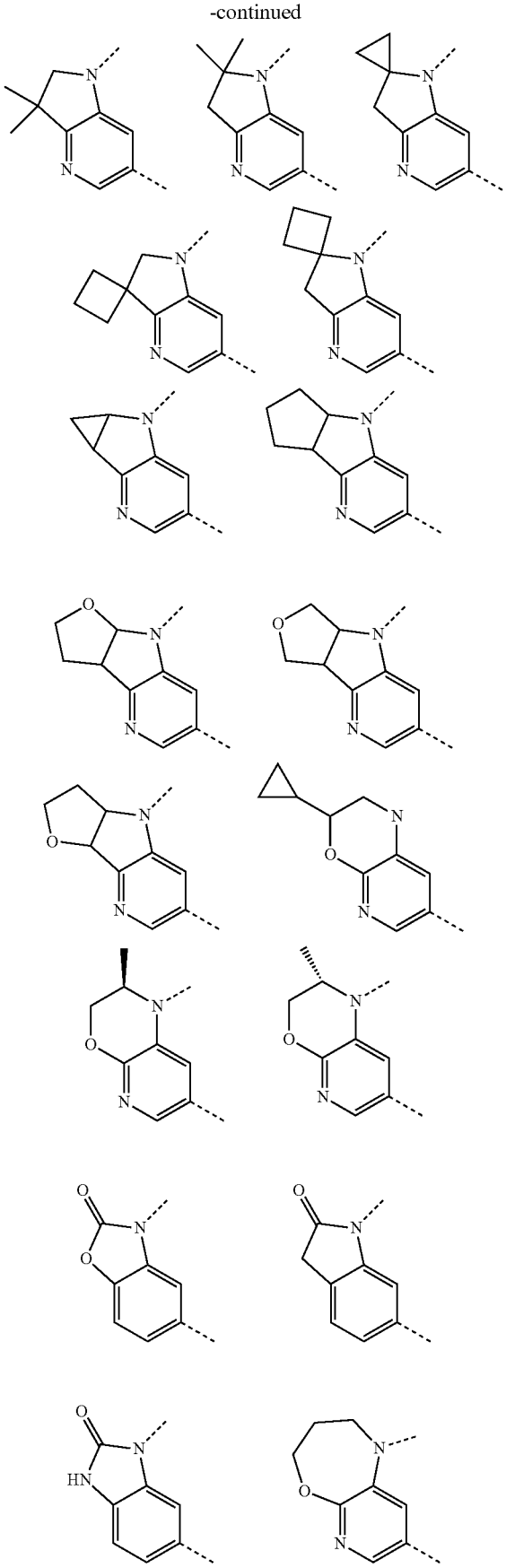

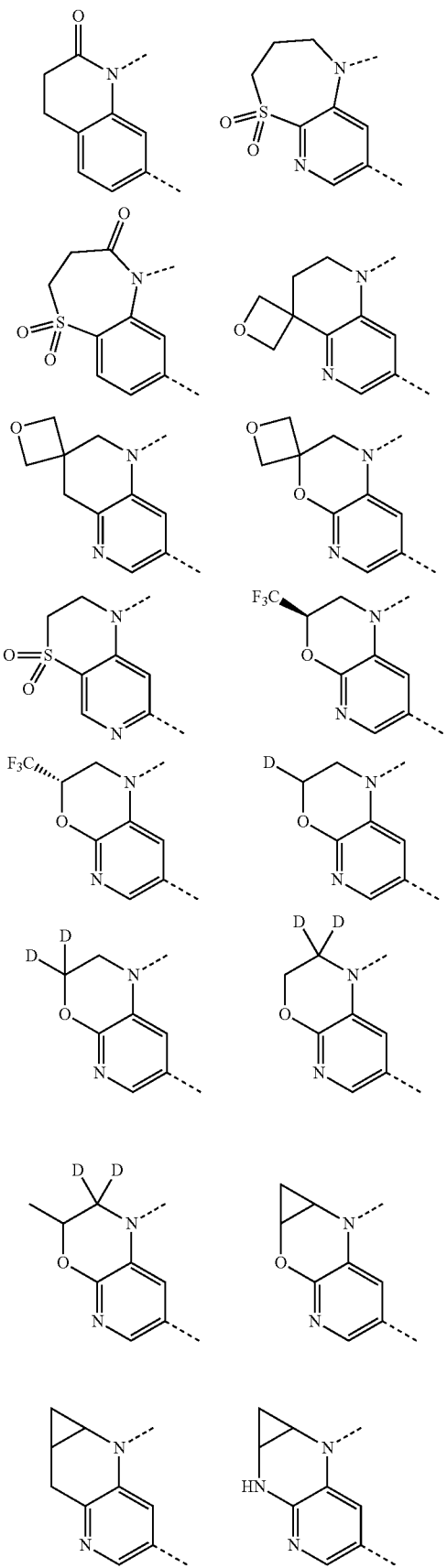
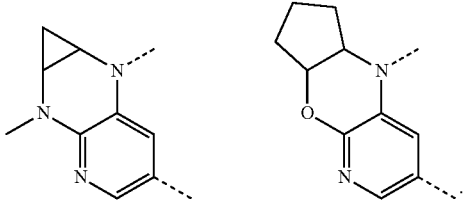
6. The compound of claim 1, wherein subgroup
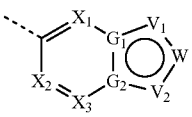
is selected from the group consisting of:
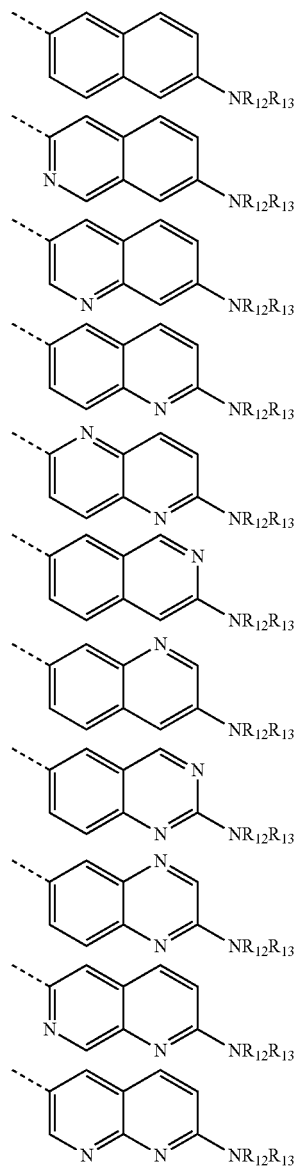

-continued
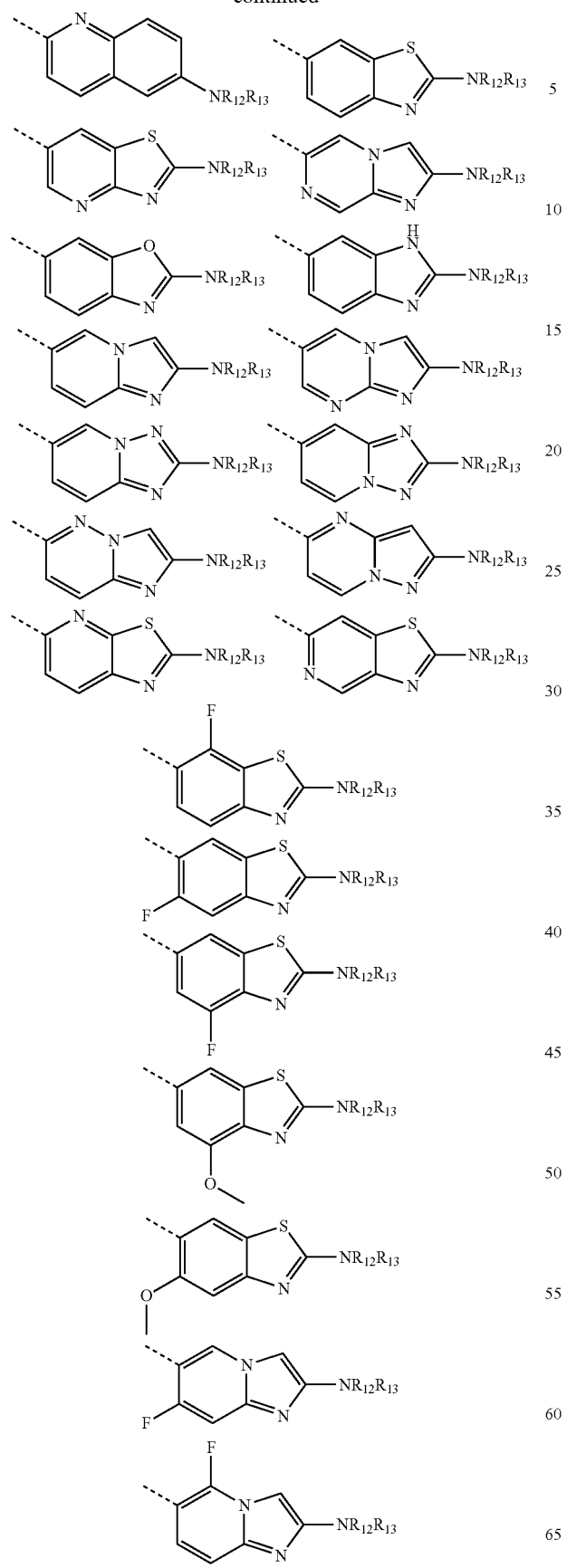
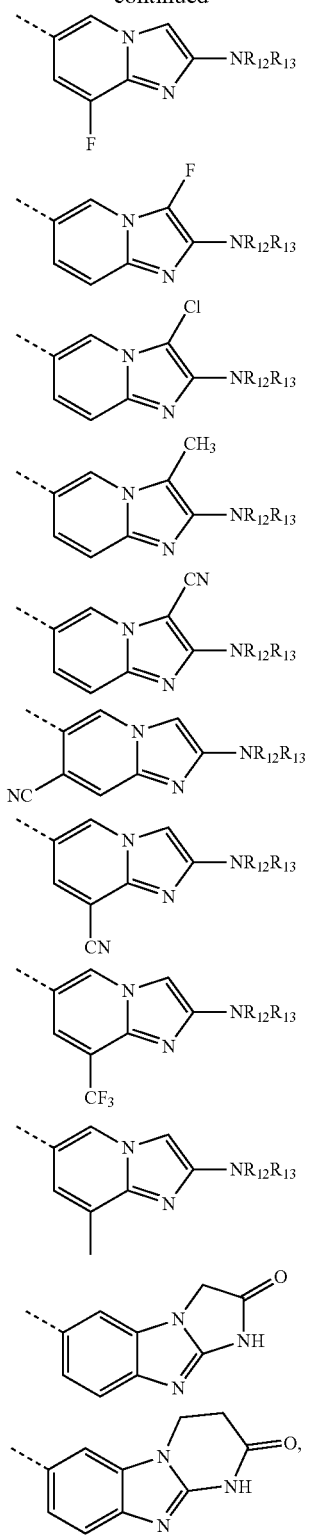
unsubstituted or substituted by 1-3 groups independently selected from the group consisting of H, deuterium, halide, —CN, —OH, amino, $C_{1-6}$ alkoxy, $C_{1-6}$ alkyl-thio, $C_{3-6}$ cycloalkyl and $C_{1-6}$ alkyl.
7. The compound of claim 1, wherein $R_1$ is selected from the group consisting of:

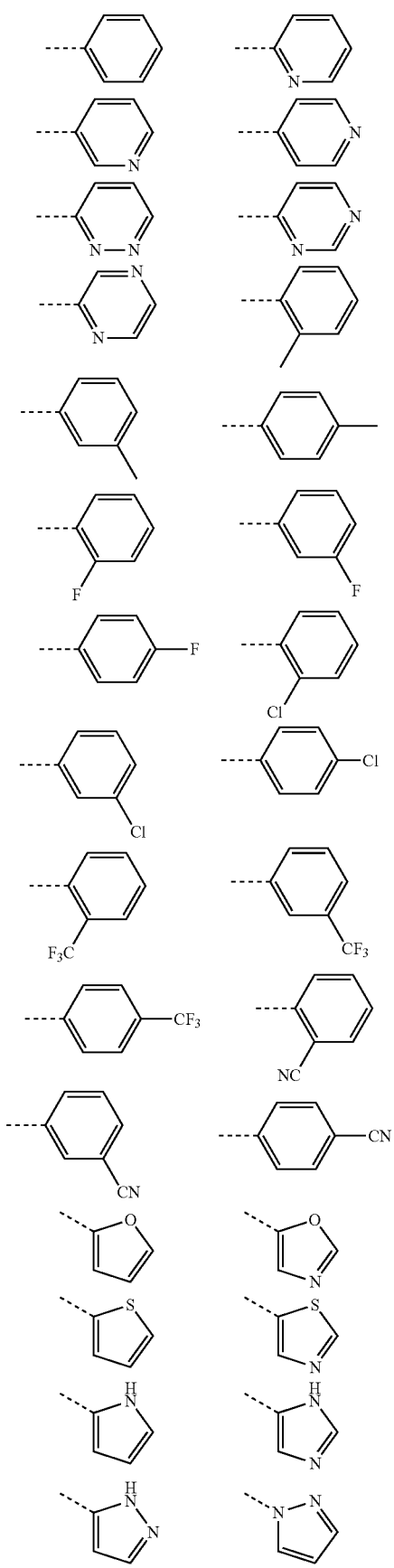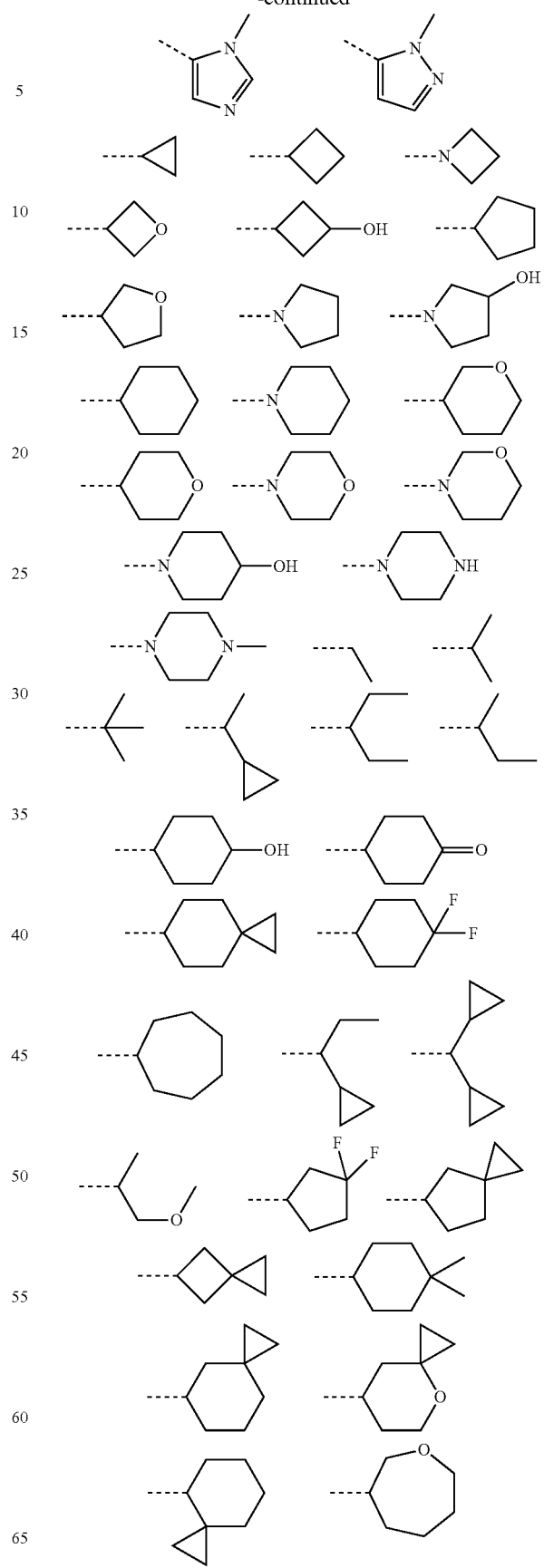

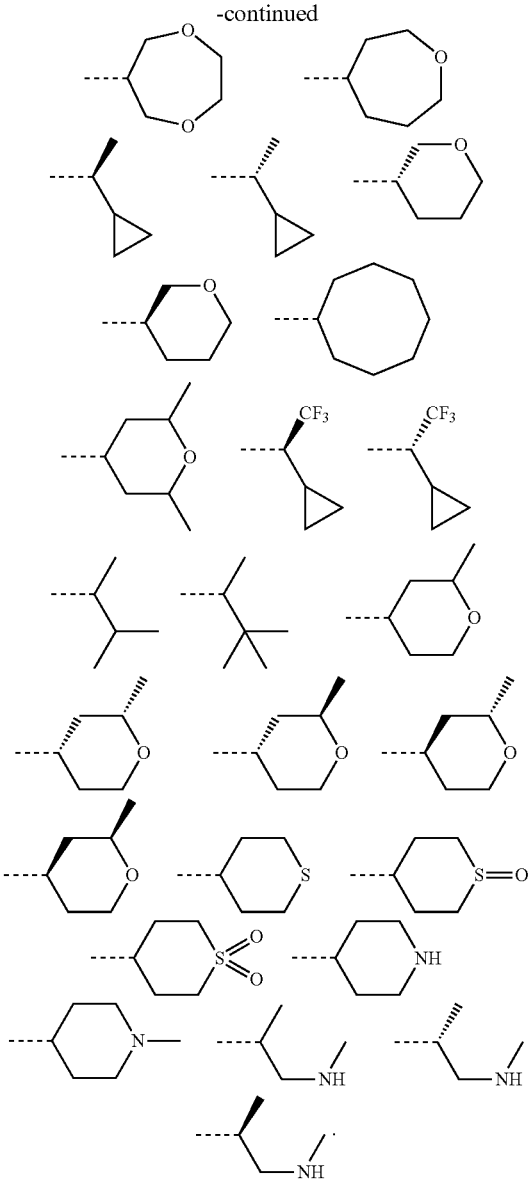
8. The compound of claim 1, wherein $R_{13}$ is selected from the group consisting of:
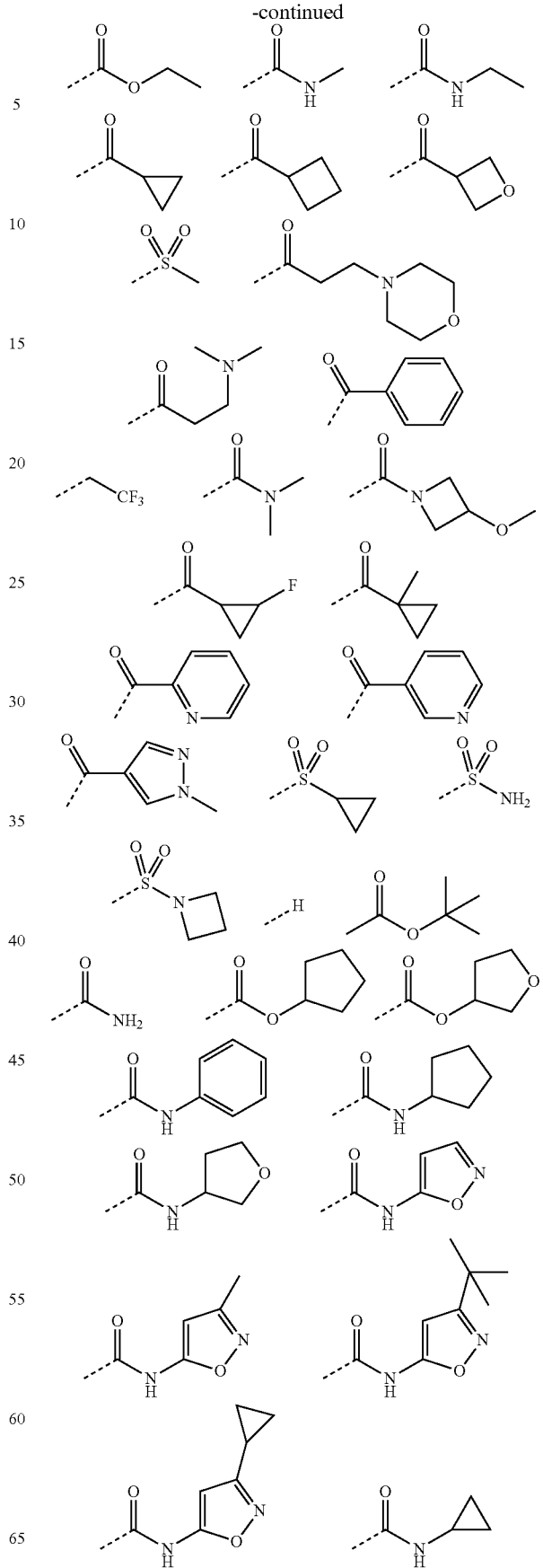

9. The compound of claim 1, wherein L is $CH_2$, O or NH.

10. The compound of claim 9, wherein n is 0 or 1; $A_1$ is N; $A_2$ is CH; and $A_3$ is CH.

11. The compound of claim 10, wherein each of $X_1$, $X_2$ and $X_3$ is independently $CR_9$.

12. The compound of claim 11, wherein $R_9$ is independently H or halide.

13. The compound of claim 12, wherein W is $C-NR_{12}R_{13}$.

14. The compound of claim 13, wherein $G_1$ is C and $G_2$ is C.

15. The compound of claim 14, wherein $V_1$ is S and $V_2$ is N.

16. The compound of claim 15, wherein L is O or $CH_2$.

17. The compound of claim 1, wherein the compound is selected from the group consisting of:

B9
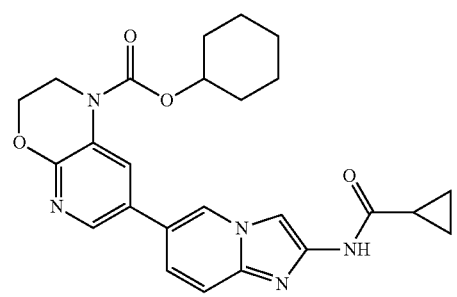
B10
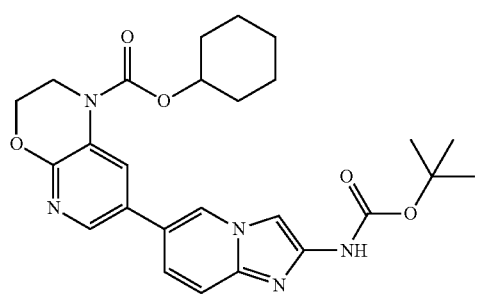
B11
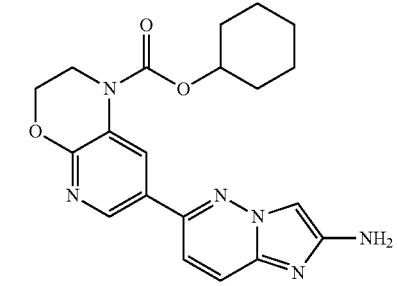
B12
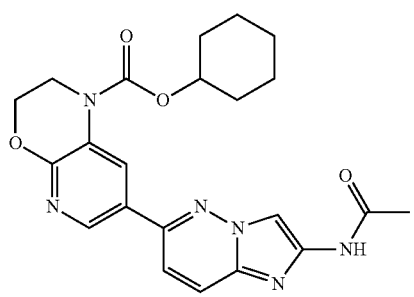
B13
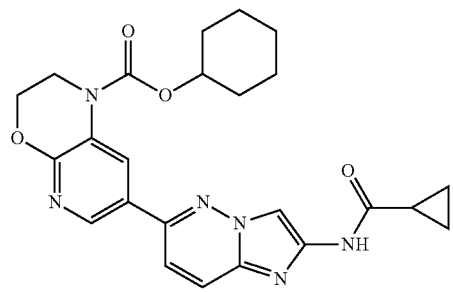
B14
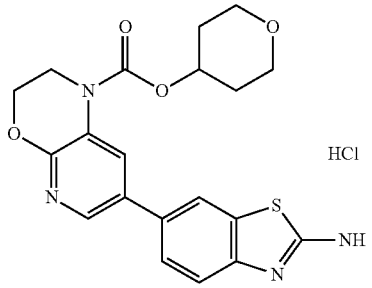
B15
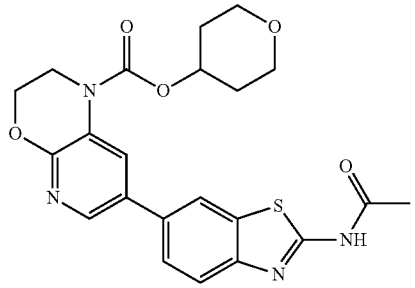
B16
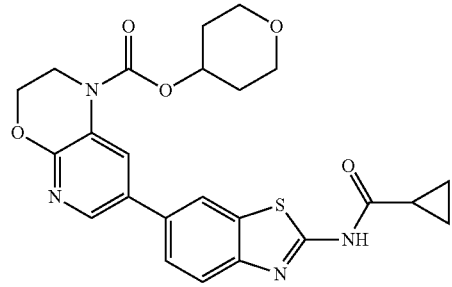
B17
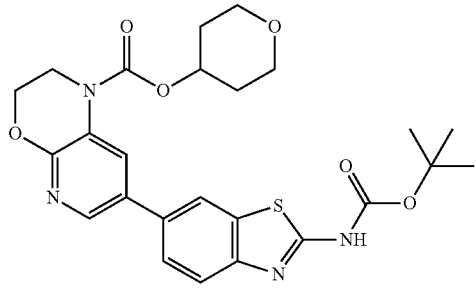
B18
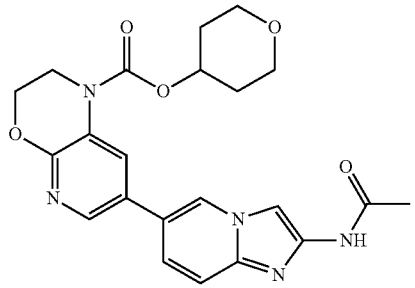

B19
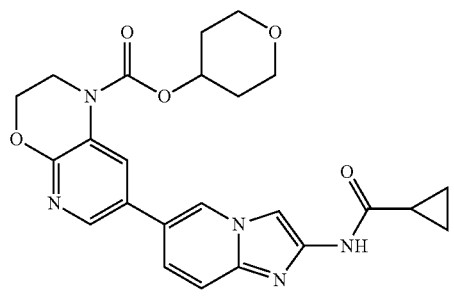
B20
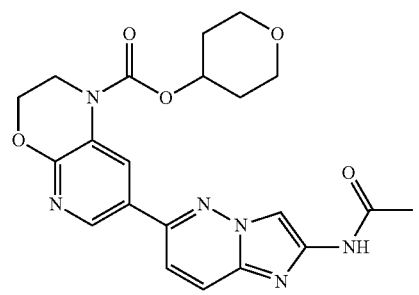
B21
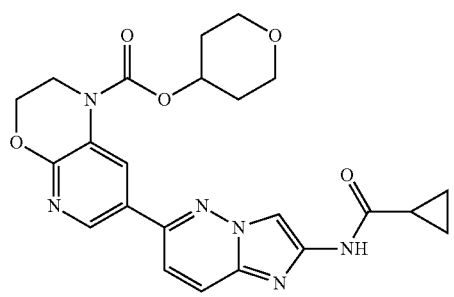
B22
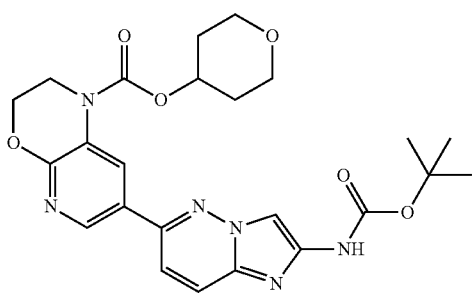
B23
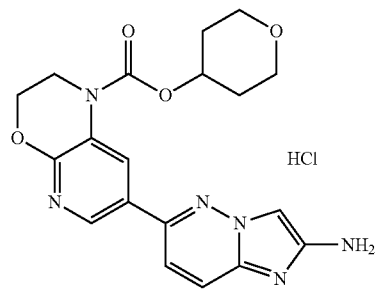
HCl
B24
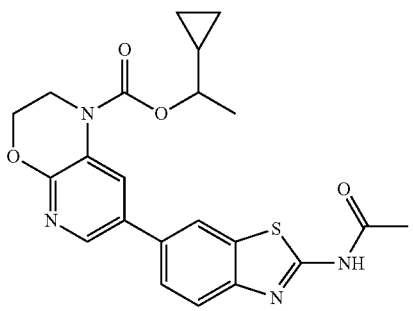
B25
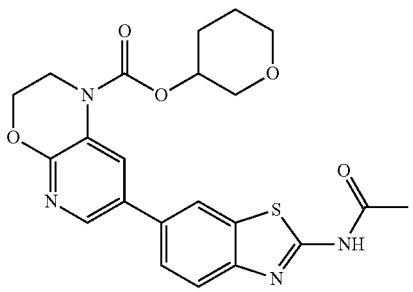
B26
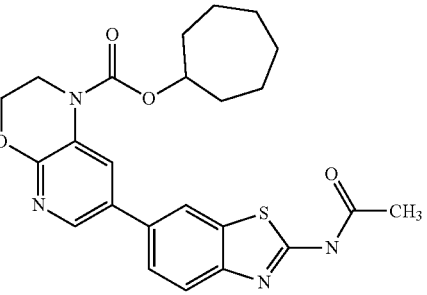
B27
B28
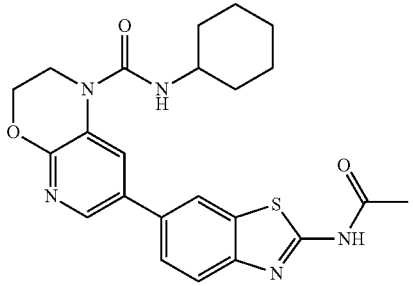

B29
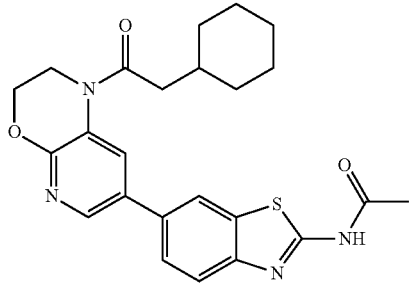
B30
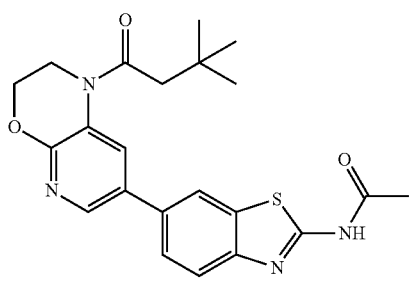
B31
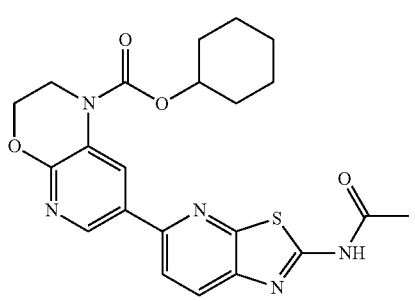
B32
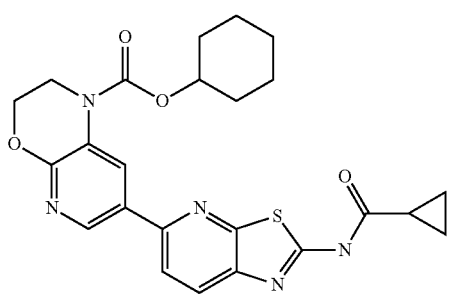
B33
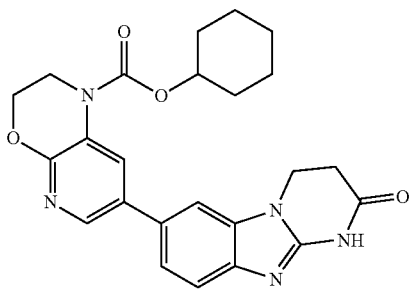
B34
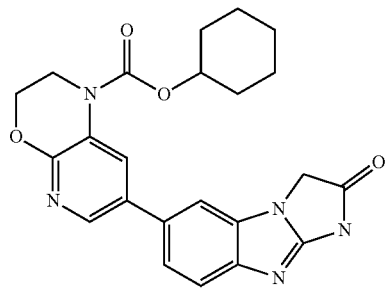
B35
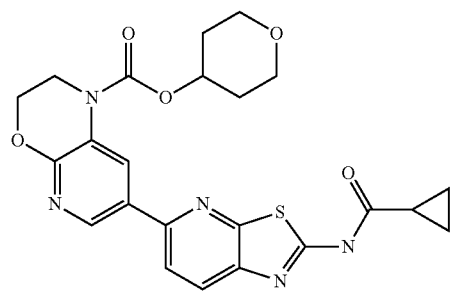
B36
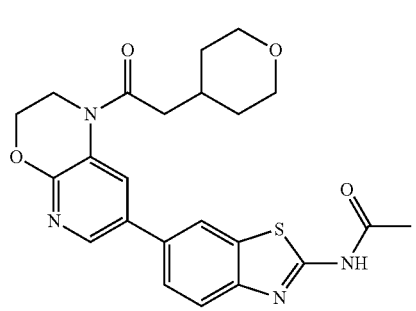
B37
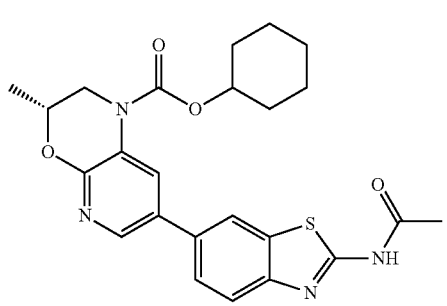
B38
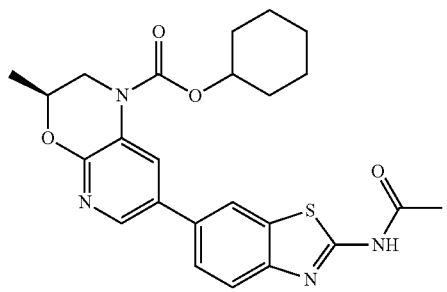

B39 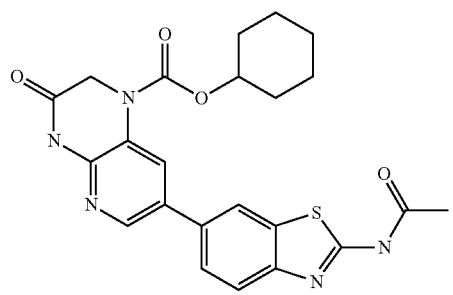
B40 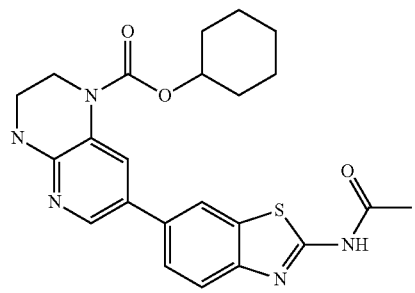
B41 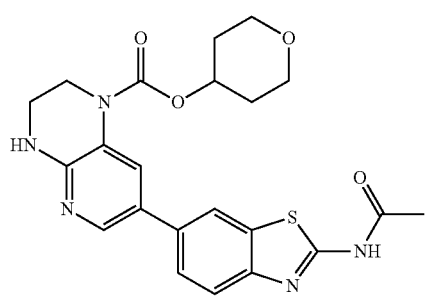
B42 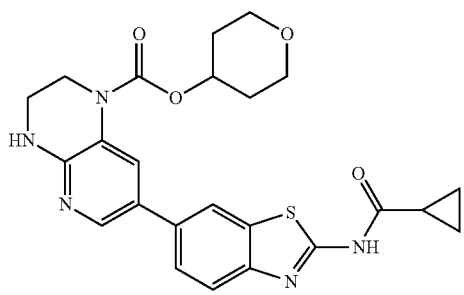
B43 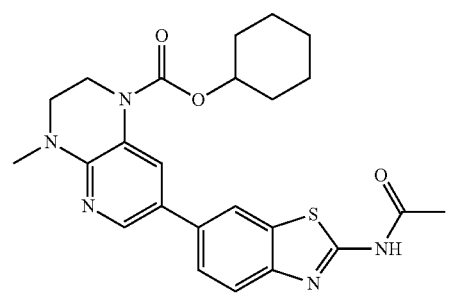
B44 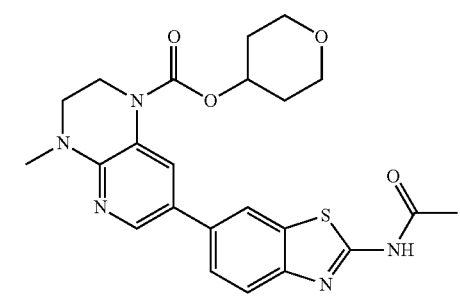
B45 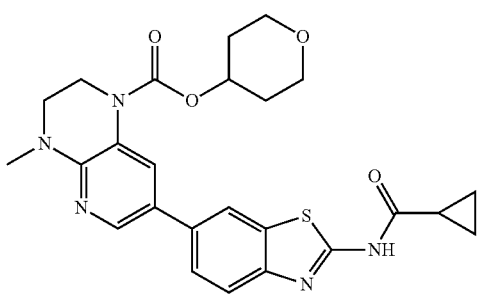
B46 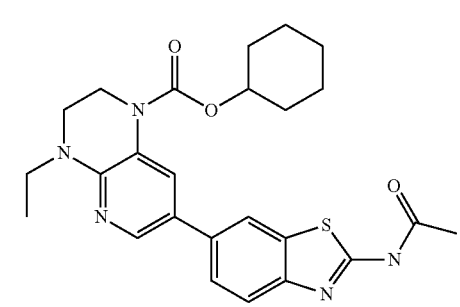
B47 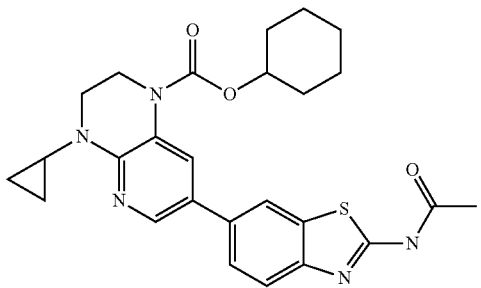
B48 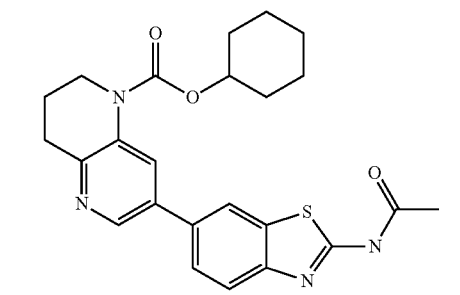

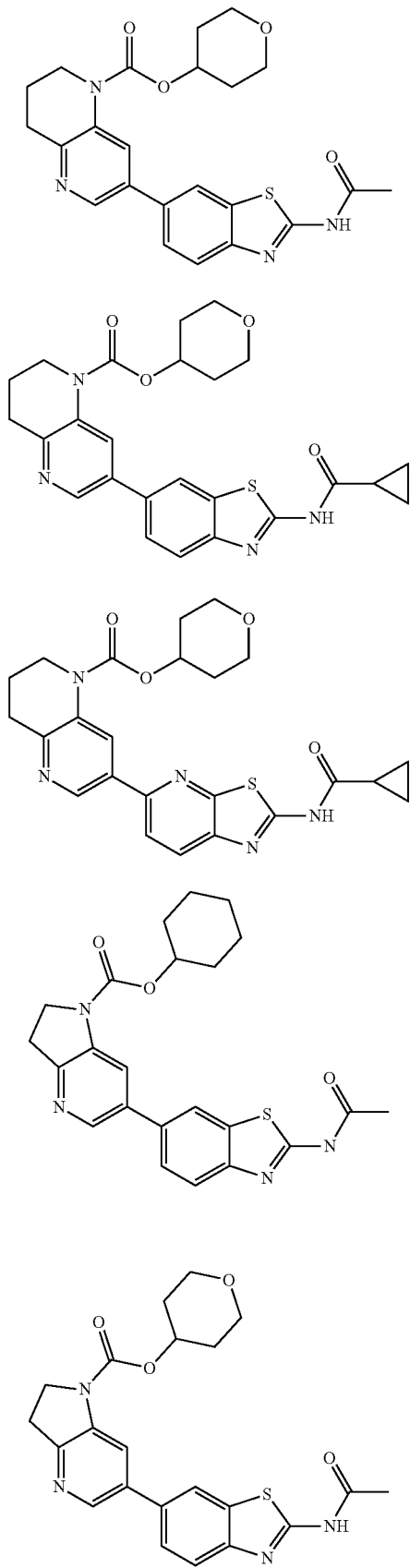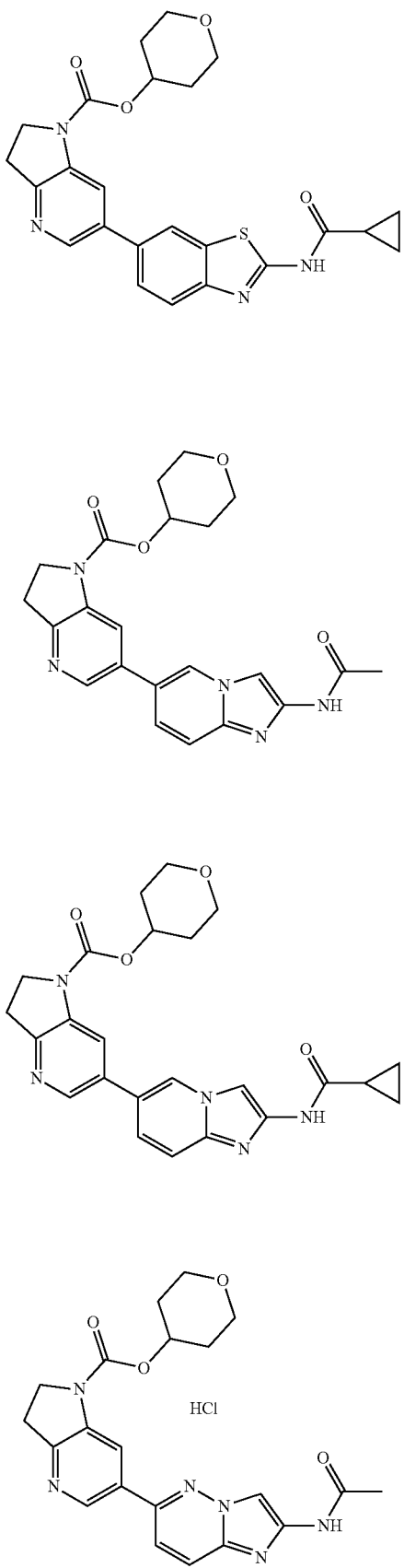

-continued
B58
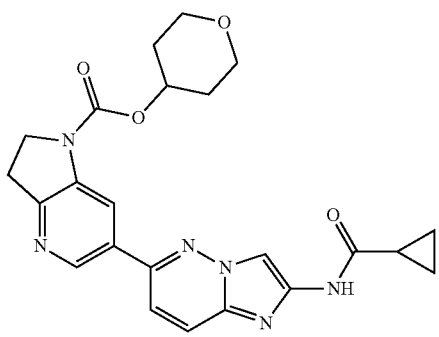
B59
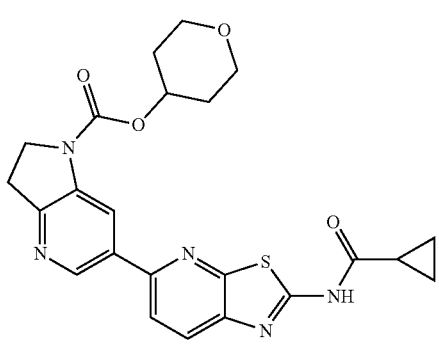
B60
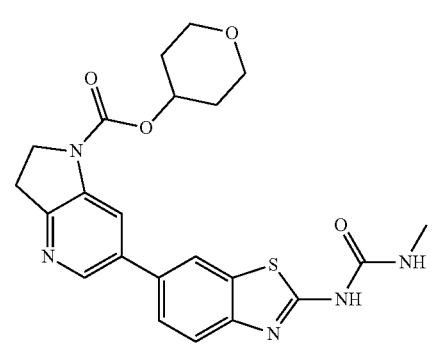
B61
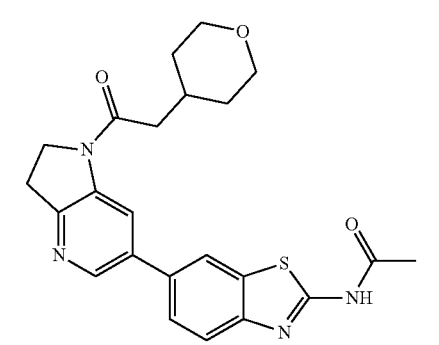
-continued
B62
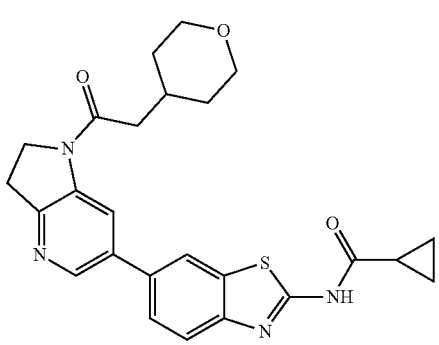
B63
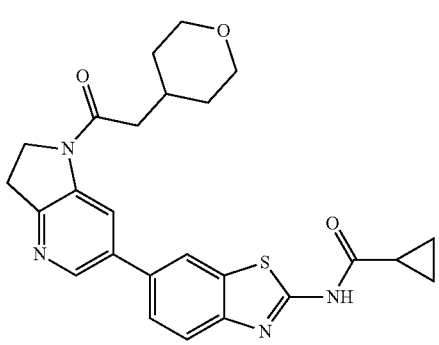
B64
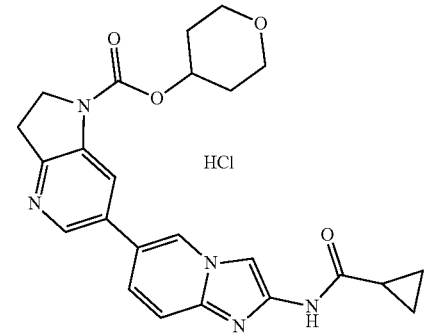
B65
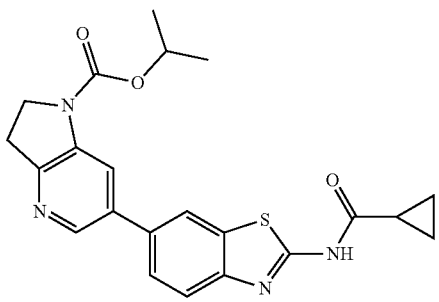
B66
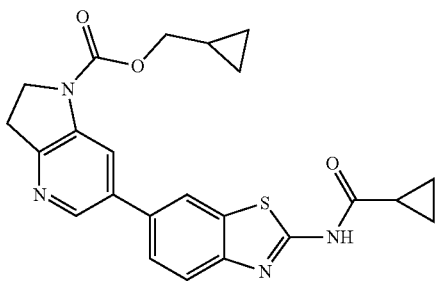

B67
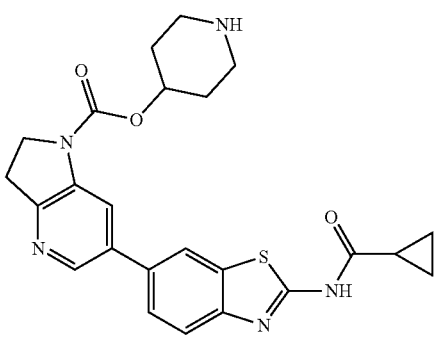
B68
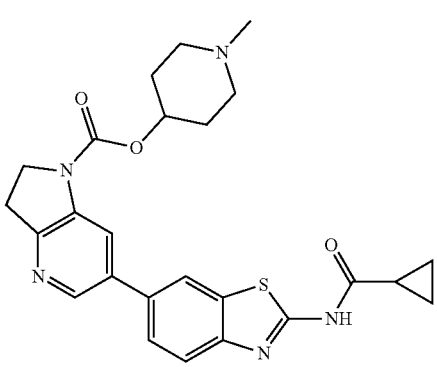
B69
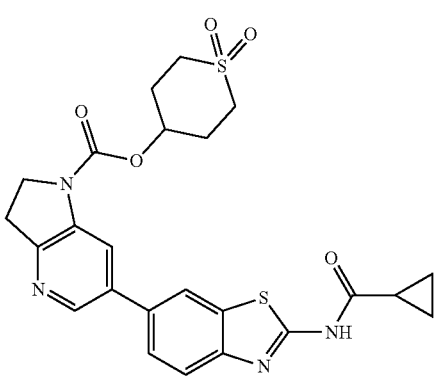
B70
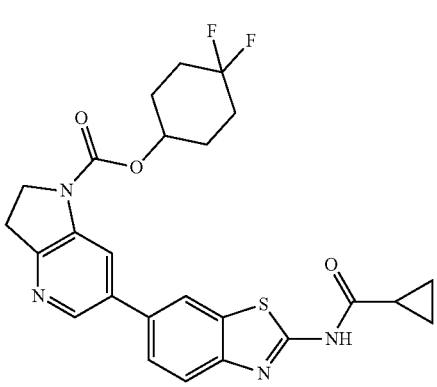
B71
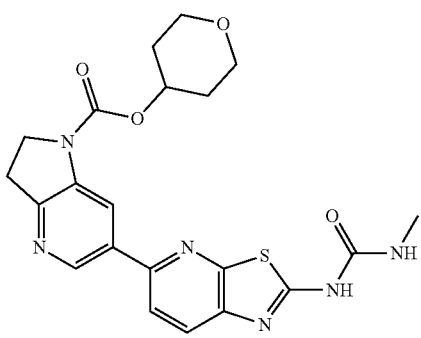
B72
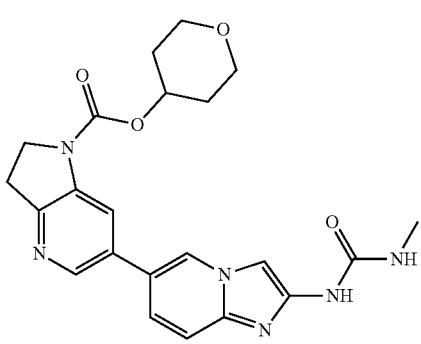
B73
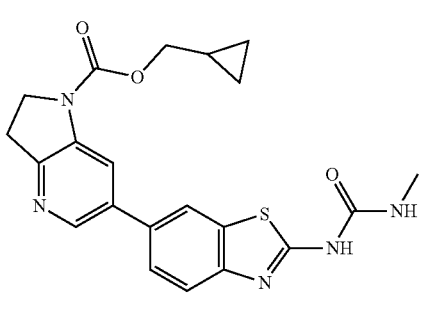
B74
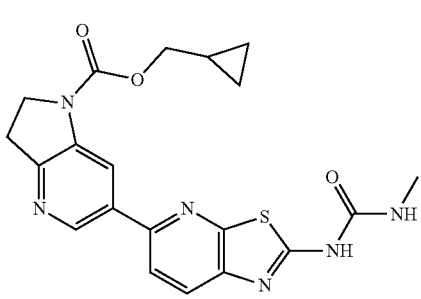
B75
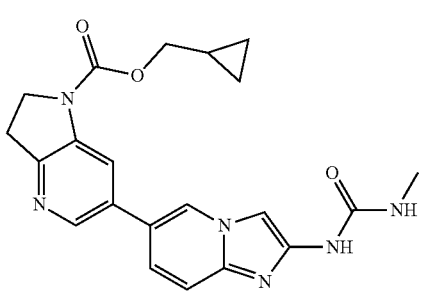

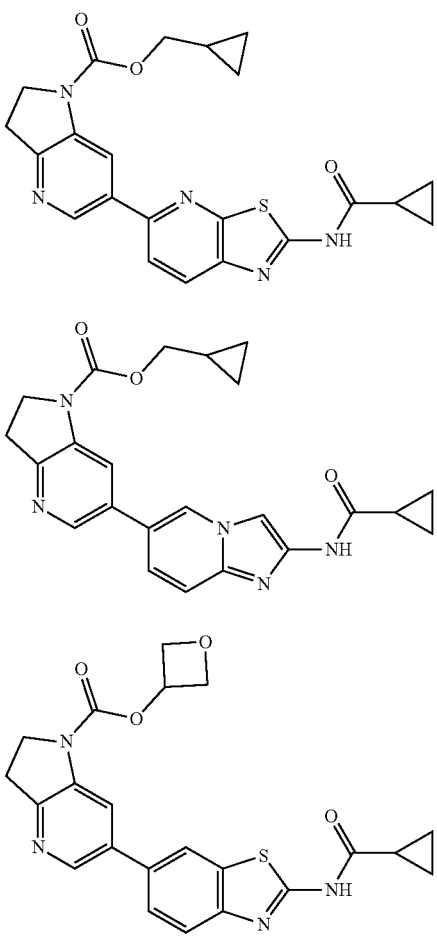

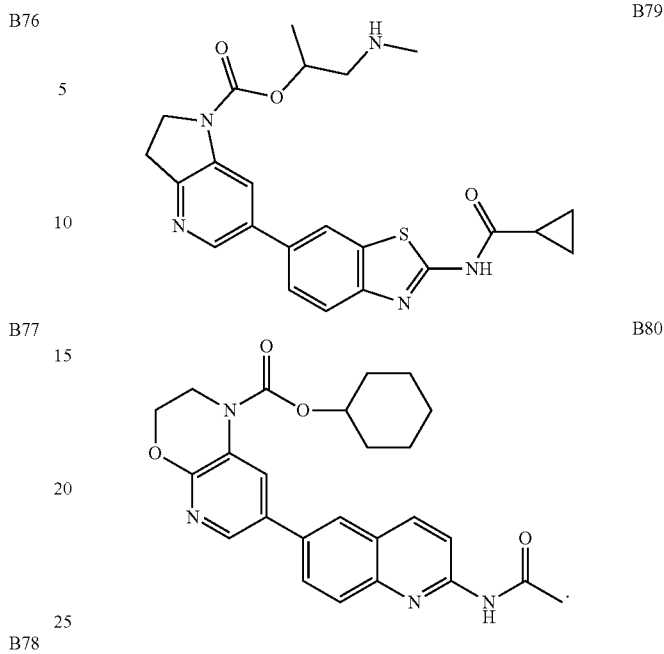

18. A pharmaceutical composition comprising a therapeutically effective amount of a compound of claim 1 and a pharmaceutically acceptable carrier, diluent, adjuvant or excipient.

19. A method for treating a necrosis-related disorder in a mammal suffering therefrom, comprising administering to the mammal a therapeutically effective amount of at least one compound of claim 1, or the pharmaceutical composition of claim 18, wherein the necrosis-related disorder is systemic inflammatory response, metabolic diseases or neurodegenerative diseases, with the proviso that the treating is not curative therapy, prophylactic therapy, or preventative therapy.

* * * * *